United States Patent
Bradley et al.

(10) Patent No.: US 6,797,731 B2
(45) Date of Patent: Sep. 28, 2004

(54) RESORCINOL DERIVATIVES

(75) Inventors: Stuart E. Bradley, Birmingham (GB); Eric W. Collington, Knebworth (GB); Matthew C. Fyfe, Birmingham (GB); William T. Gattrell, Birmingham (GB); Joanna V. Geden, Coventry (GB); Peter J. Murray, Birmingham (GB); Martin J. Procter, Walsall (GB); Robert J. Rowley, Coventry (GB); Jonathan G. Williams, Nuneaton (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/386,878

(22) Filed: Mar. 12, 2003

(65) Prior Publication Data

US 2003/0190298 A1 Oct. 9, 2003

Related U.S. Application Data

(63) Continuation of application No. 09/953,690, filed on Sep. 17, 2001, now Pat. No. 6,541,473.

(60) Provisional application No. 60/234,468, filed on Sep. 21, 2000.

(51) Int. Cl.$^7$ .............................................. A61K 31/17
(52) U.S. Cl. ...................................................... 514/595
(58) Field of Search ........................................ 514/595

(56) References Cited

U.S. PATENT DOCUMENTS

| | | | |
|---|---|---|---|
| 4,645,780 A | 2/1987 | Dressler et al. | |
| 4,959,393 A | 9/1990 | Torihara et al. | |
| 6,132,740 A | 10/2000 | Hu | |
| 6,221,342 B1 * | 4/2001 | Huglin et al. | 424/59 |
| 6,573,284 B1 * | 6/2003 | Riley et al. | 514/346 |

* cited by examiner

*Primary Examiner*—Deborah C. Lambkin
(74) *Attorney, Agent, or Firm*—Rosanne Goodman

(57) ABSTRACT

The present invention relates to certain resorcinol derivatives and their use as skin lightening agents.

6 Claims, No Drawings

RESORCINOL DERIVATIVES

This application is a continuation of U.S. patent application Ser. No. 09/953,690 filed Sep. 17, 2001, which is now U.S. Pat. No. 6,541,473, which claims priority from U.S. provisional application serial No. 60/234,468 filed Sep. 21, 2000.

FIELD OF THE INVENTION

The present invention relates to certain resorcinol derivatives and their use as skin lightening agents.

BACKGROUND OF THE INVENTION

The terms "lightening agent" and "depigmentation agent" are used interchangeably throughout this document.

Skin color in humans arises from a complex series of cellular processes that are carried out within a unique population of cells called melanocytes. Melanocytes are located in the lower part of the epidermis, and their function is to synthesize a pigment, melanin, which protects the body from the damaging effects of ultraviolet radiation.

When skin is exposed to ultraviolet radiation, such as that contained in sunlight, melanocytes increase their synthesis of melanin. Melanin is deposited in melanosomes, which are vesicles found within the cell. The melanosomes are extruded from the cell and carried to the surface of the skin by keratinocytes, which internalize the melanin-containing melanosomes. The end result is that the visible layers of the skin exhibit a brown color typically known as a "tan". The darkness of the color observed in the skin is proportionate to the amount of melanin synthesized by melanocytes and transferred to the keratinocytes.

The mechanism by which skin pigmentation is formed, melanogenesis, is particularly complex and schematically involves the following main steps: Tyrosine→L-Dopa→Dopaquinone→Dopachrome→Melanins. The first two reactions in this series are catalyzed by the enzyme tyrosinase. The activity of tyrosinase is promoted by the action of α-melanocyte stimulating hormone or UV rays. It is well established that a substance has a depigmenting effect if it acts directly on the vitality of the epidermal melanocytes where melanogenesis normally occurs and/or if it interferes with one of the stages in melanin biosynthesis. The active compounds that are employed in the various methods and compositions of this invention inhibit tyrosinase and thus inhibit or decrease melanin biosynthesis.

There is a strong demand for agents that enable acquired deposition sites, such as spots or freckles, to be restored to a normal skin color. For this purpose, a variety of agents and methods have been developed and put on the market. Examples of such methods are (a) a method wherein vitamin C (L-ascorbic acid) having good reducing ability is administered orally in large amounts, (b) a method wherein glutathione is administered parenterally; (c) a method wherein a peroxide, such as hydrogen peroxide, zinc peroxide, sodium peroxide and the like, is administered: and (d) a method wherein vitamin C or cysteine is administered topically in the form of an ointment, cream, lotion or the like. Vitamin C has a problem with respect to stability and becomes so unstable in water-containing systems that they will cause changes in odor and color. Thiol compounds such as glutathione and cysteine do not exhibit a satisfactory depigmental effect since the development of the effect is very slow.

The substances in widest use at the present time as depigmentors are, in particular, hydroquinone and its derivatives, particularly its ethers such as hydroquinone monomethyl ether. These compounds, while effective, are known to produce side effects that can be dangerous. Hydroquinone, use of which is limited to a concentration of 2%, is both irritating and cytotoxic to the melanocyte.

U.S. Pat. No. 4,526,179 refers to certain hydroquinone fatty esters that have good activity and are less irritating and more stable than hydroquinone.

Japanese Patent Application No. 27909/86 refers to other hydroquinone derivatives that do not have the drawbacks of hydroquinone but that have relatively poor efficacy.

U.S. Pat. No. 5,449,518 refers to 2,5-dihydoxyphenyl carboxylic acid derivatives as skin depigmentation agents.

European Patent Application EP 341,664A1 refers to certain resorcinol derivatives as tyrosinase inhibitors and skin depigmentation agents.

PCT International Publication WO 99/15148 refers to certain resorcinol derivatives as tyrosinase inhibitors and skin depigmentation agents.

The use of topical depigmention agents that have good efficacy and are harmless is particularly desirable for treating the following: regional hyperpigmentation caused by melanocytic hyperactivity, such as idiopathic melasma occurring either during pregnancy (mask of pregnancy or chloasma) or secondary to estrogen-progesterone contraception; local hyperpigmentation caused by benign melanocytic hyperactivity and proliferation such as lentigo senilis or liver spots; accidental hyperpigmentation such as post-lesional photosensitization and scarring; and certain forms of leukoderma such as vitiligo where, if the injured skin cannot be repigmented, the residual zones of normal skin are depigmented to impart a homogeneous white color to the entire skin.

SUMMARY OF INVENTION

The resorcinol derivatives of formula I, which are defined below and used in the various methods and compositions of this invention, are useful in the treatment of the foregoing dermatological conditions as well as other dermatological conditions, some of which are referred to later in this document, for which the subject being treated desires, for medicinal or cosmetic purposes, to lighten or reduce the pigmentation of the skin affected by the condition.

The resorcinol derivatives of formula I are also useful for the treatment of inflammatory disorders such as psoriasis, dermatitis and acne, and for the treatment of dandruff.

The invention thus provides a compound of formula I:

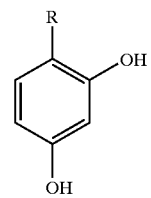

I or a pharmaceutically acceptable salt thereof, wherein:

R is a $(C_3-C_8)$cycloalkyl or $(C_5-C_8)$cycloalkenyl ring substituted by —N(R$^1$)CONR$^2$R$^3$ wherein R$^1$ and R$^2$ are independently selected from hydrogen, $(C_1-C_6)$alkyl, and, aryl$(C_1-C_6)$alkyl and R$^3$ is hydrogen, $(C_1-C_6)$alkyl, aryl$(C_1-C_6)$alkyl, or aryl; —N(R$^4$)COR$^5$ wherein R$^4$ is hydrogen, $(C_1-C_6)$alkyl, aryl$(C_1-C_6)$alkyl-, or OH and R$^5$ is $(C_7-C_{10})$alkyl, aryl, aryl ($C_1$–$C_6$)alkyl-, —O-aryl, $CF_3$, heterocycloalkyl, —($C_1$–$C_6$)alkylheterocycloalkyl, —($C_2$–$C_7$)alkenylheterocycloalkyl, heteroaryl, —($C_1$–$C_6$)alkyl heteroaryl, —($C_2$–$C_7$)alkenylheteroaryl, —($C_2$–$C_7$)alkenylaryl, —($C_2$–$C_7$)alkenylCOaryl, —($C_1$–$C_6$)alkylN($R^4$)CO-aryl, —($C_1$–$C_6$)alkylCO-aryl, —($C_1$–$C_6$)alkylheterocycloalkyl, —($C_1$–$C_6$)alkyl-X-aryl, ($C_2$–$C_7$)alkenyl, benzyhydryl, 5-hydroxyoxoindanyl, or tetrahydronaphthalenyl, wherein X is O, S, SO, $SO_2$ or $NR^1$; —N($R^1$)OCOaryl; =$CHCO_2R^1$; =$CHCONR^1R^2$; =CHCN; =$NNHSO_2R^6$ wherein $R^6$ is aryl; —N(O)=$CHR^6$; —OC(O)$NR^1R^7$ wherein $R^7$ is aryl, aryl($C_1$–$C_6$)alkyl-, —($C_1$–$C_6$)alkyl-$CO_2$($C_1$–$C_6$)alkyl, —$CO_2$($C_1$–$C_6$) alkyl, —$CO_2$aryl, —$CO_2$aryl, or —$CO_2$($C_1$–$C_6$) alkylaryl; amino($C_1$–$C_6$)alkylaryl$CO_2$—; or —OC(O)$OR^8$ wherein $R^8$ is ($C_1$–$C_8$)alkyl, aryl($C_1$–$C_6$)alkyl, or aryl;

with the proviso that the cycloalkenyl ring is not aromatic.

In a preferred embodiment, R is substituted by —N($R^1$)$CONR^2R^3$.

In a further preferred embodiment, R is substituted by —N($R^4$)$COR^5$.

In a further preferred embodiment, R is substituted by —N($R^1$)OCOaryl.

In a further preferred embodiment, R is substituted by =$CHCO_2R^1$.

In a further preferred embodiment, R is substituted by =$CHCONR^1R^2$.

In a further preferred embodiment, R is substituted by =CHCN.

In a further preferred embodiment, R is substituted by =$NNHSO_2R^6$.

In a further preferred embodiment, R is substituted by —N(O)=$CHR^6$.

In a further preferred embodiment, R is substituted by —OC(O)$NR^1R^7$.

In a further preferred embodiment, R is substituted by amino($C_1$–$C_6$)alkylaryl$CO_2$—.

In a further preferred embodiment, R is substituted by —OC(O)$OR^8$.

The invention further provides a compound of formula I wherein R is a ($C_3$–$C_8$)cycloalkyl or ($C_5$–$C_8$)cycloalkenyl ring substituted by =$CH_2$, or a pharmaceutically acceptable salt thereof; with the proviso that the cycloalkenyl ring is not aromatic.

In a preferred embodiment, R is a cycloalkyl ring, and preferably a cyclohexyl or cyclopentyl ring. Where R is a cyclohexyl or cyclohexenyl ring, the ring is preferably substituted at the 3- or 4-position, and more preferably at the 4-position. Where R is a cyclopentyl or cyclopentenyl ring, the ring is preferably substituted at the 3-position.

The invention further provides a compound of formula I wherein R is 3-cyclohexenyl, which is preferably unsubstituted, or a pharmaceutically acceptable salt thereof.

The invention further provides a compound of formula I, wherein R is a ($C_3$–$C_8$)cycloalkyl or ($C_5$–$C_8$)cycloalkenyl ring, wherein one of the carbon atoms of said cycloalkyl or cycloalkenyl rings is substituted by two groups such that the said groups are taken together with the carbon to which they are attached to form a ring of the formula:

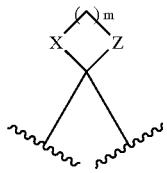

wherein X is O, S, SO, $SO_2$ or $NR^1$, wherein $R^1$ is as defined above; Z is $CH_2$, O, S, SO or $SO_2$; m is 0–3; with the proviso that when m=0, then Z is $CH_2$; and with the proviso that the cycloalkenyl ring is not aromatic; or a pharmaceutically acceptable salt thereof. In a preferred embodiment, m is 0. In a further preferred embodiment, m is 2. In a preferred embodiment, X and Z are both 0. In a further preferred embodiment, X and Z are both S. In a preferred embodiment, where R is a cyclohexyl or cyclohexenyl ring, the carbon of the cyclohexyl or cyclohexenyl ring which is substituted by the two groups is at the 3- or 4-position, and preferably at the 4-position, of the cyclohexyl or cyclohexenyl ring. In a further preferred embodiment, where R is a cyclopentyl or cyclopentenyl ring, the carbon of the cyclopentyl or cyclopentenyl ring which is substituted by the two groups is at the 3-position of the cyclopentyl or cyclopentenyl ring.

The invention further provides a compound of formula I, wherein R is a ($C_3$–$C_8$)cycloalkyl or ($C_1$–$C_8$)cycloalkenyl ring, wherein one of the carbon atoms of said cycloalkyl or cycloalkenyl rings is substituted by two groups such that the said groups are taken together with the carbon to which they are attached to form a ring of the formula:

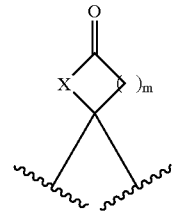

wherein X is O, S, SO, $SO_2$ or $NR^1$, wherein $R^1$ is as defined above; and m is 0–3; and with the proviso that the cycloalkenyl ring is not aromatic; or a pharmaceutically acceptable salt thereof. In a preferred embodiment, m is 2. In a further preferred embodiment, X is O. In a preferred embodiment, where R is a cyclohexyl or cyclohexenyl ring, the carbon of the cyclohexyl or cyclohexenyl ring which is substituted by the two groups is at the 3- or 4-position, and preferably at the 4-position, of the cyclohexyl or cyclohexenyl ring. In a further preferred embodiment, where R is a cyclopentyl or cyclopentenyl ring, the carbon of the cyclopentyl or cyclopentenyl ring which is substituted by the two groups is at the 3-position of the cyclopentyl or cyclopentenyl ring.

The invention further provides a compound selected from the group consisting of:
4-(1,4-Dioxaspiro[4.5]decyl)-1,3-benzenediol;
(±)-{4-[2,4-Dihydroxyphenyl]cyclohexylidene}acetic acid;
(±)-[4-(2,4-Dihydroxyphenyl)cyclohexylidene] acetonitrile;
cis-N-[4-(2,4-Dihydroxyphenyl)cyclohexyl]-N-hydroxybenzamide;
cis-N-[4-(2,4-Dihydroxyphenyl)cyclohexyl]benzamide;
trans-4-{4-[(Z)benzylidene(oxido)amino]cyclohexyl}-1,3-benzenediol;

trans-N-[4-(2,4-Dihydroxyphenyl)cyclohexyl]-N-hydroxybenzamide;

syn-8-(2,4-Dihydroxyphenyl)-1-oxaspiro[4.5]decan-2-one;

cis-N-[4-(2,4-Dihydroxyphenyl)cyclohexyl]-N'-phenylurea;

trans-Phenyl-4-(2,4-dihydroxyphenyl)cyclohexylcarbamate;

cis-N-Benzyl-N-[4-(2,4-dihydroxyphenyl)cyclohexyl]-N'-ethylurea;

cis-N-Benzyl-N[4-(2,4-dihydroxyphenyl)cyclohexyl]propanamide;

trans-4-(2,4-Dihydroxyphenyl)cyclohexylphenylcarbamate;

trans-Ethyl[({[4-(2,4-dihydroxyphenyl)cyclohexyl]oxy}carbonyl)amino]acetate;

trans-4-(2,4-Dihydroxyphenyl)cyclohexyl benzylcarbamate;

trans-4-(2,4-Dihydroxyphenyl)cyclohexyl ethyl carbonate;

trans-Methyl[({[4-(2,4-dihydroxyphenyl)cyclohexyl]oxy}carbonyl)amino]acetate;

trans-4-(2,4-Dihydroxyphenyl)cyclohexyl methyl imidodicarbonate;

cis/trans-4-(1-Oxaspiro[2.5]oct-6-yl)-1,3-benzenediol;

4-(4-Methylenecyclohexyl)-1,3-benzenediol;

4-(3-Cyclohexen-1-yl)-1,3-benzenediol;

trans-4-(2,4-Dihydroxyphenyl)cyclohexyl (2R)-2-amino-3-phenylpropanoate;

Benzyl [4-(2,4-dihydroxyphenyl)cyclohexylidene]acetate;

4-(1,4-Dithiaspiro[4.5]dec-8-yl)-1,3-benzenediol;

N'-[4-(2,4-Dihydroxyphenyl)cyclohexylidene]4-methylbenzenesulfonohydrazide;

trans-N-[4-(2,4-Dihydroxyphenyl)cyclohexyl]-3-nitrobenzamide;

trans-N-[4-(2,4-dihydroxyphenyl)cyclohexyl]-N'-phenylurea;

trans-N-[4-(dihydroxyphenyl)cyclohexyl]-2,2,2-trifluoroacetamide;

cis-3-cyano-N-[4-(2,4-dihydroxyphenyl)cyclohexyl]-N-hydroxybenzamide;

cis-N-[4-(2,4-dihydroxyphenyl)cyclohexyl]-N-hydroxy(trifluoromethyl)benzamide;

cis-N-[4-(2,4-dihydroxyphenyl)cyclohexyl]-N-hydroxymethoxybenzamide;

(±)-Methyl[4-(2,4-dihydroxyphenyl)cyclohexylidene]acetate;

and a pharmaceutically acceptable salt thereof.

The present invention further provides a pharmaceutical composition for lightening skin or reducing the pigmentation of skin in a human, comprising a pharmaceutically acceptable carrier, and a skin-lightening or pigmentation-reducing effective amount of a compound of formula I:

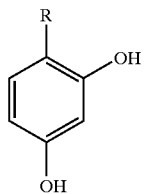

or a pharmaceutically acceptable salt thereof, wherein:
R is a $(C_3-C_8)$cycloalkyl or $(C_5-C_8)$cycloalkenyl ring substituted by —$N(R^1)CONR^2R^3$ wherein $R^1$ and $R^2$ are independently selected from hydrogen, $(C_1-C_6)$alkyl, and aryl$(C_1-C_6)$alkyl and $R^3$ is hydrogen, $(C_1-C_6)$alkyl, aryl$(C_1-C_6)$alkyl, or aryl; —$N(R^4)COR^5$ wherein $R^4$ is hydrogen, $(C_1-C_6)$alkyl, aryl$(C_1-C_6)$alkyl-, or OH and $R^5$ is $(C_7-C_{10})$alkyl, aryl, aryl$(C_1-C_6)$alkyl-, —O-aryl, $CF_3$, heterocycloalkyl, —$(C_1-C_6)$alkylheterocycloalkyl, —$(C_2-C_7)$alkenylheterocycloalkyl, heteroaryl, —$(C_1-C_6)$alkyl heteroaryl, —$(C_2-C_7)$alkenylheteroaryl, —$(C_2-C_7)$alkenylaryl, —$(C_2-C_7)$alkenylCOaryl, —$(C_1-C_6)$alkylN$(R^4)$CO-aryl, —$(C_1-C_6)$alkylCO-aryl, —$(C_1-C_6)$alkylhydroxyaryl, —$(C_1-C_6)$alkyl-X-aryl, $(C_2-C_7)$alkenyl, benzyhydryl, 5-hydroxyoxoindanyl, or tetrahydronaphthalenyl, wherein X is O, S, SO, $SO_2$ or $NR^1$; —$N(R^1)OCOaryl$; =$CHCO_2R^1$; =$CHCONR^1R^2$; =CHCN; =$NNHSO_2R^6$ wherein $R^6$ is aryl; —$N(O)$=$CHR^6$; —$OC(O)NR^1R^7$ wherein $R^7$ is aryl, aryl$(C_1-C_6)$alkyl-, —$(C_1-C_6)$alkyl, $CO_2$ $(C_1-C_6)$alkyl, —$CO_2(C_2$aryl), or —$CO_2(C_1-C_5)$alkylaryl; amino$(C_1-C_5)$alkylarylCO$_2$—; or —OC(O)OR$^8$ wherein $R^1$ is $(C_1-C_6)$alkyl, aryl$(C_1-C_6)$alkyl, or aryl;
with the proviso that the cycloalkenyl ring is not aromatic.

In a preferred embodiment, R is substituted by —$N(R^1)CONR^2R^3$.

In a further preferred embodiment, R is substituted by —$N(R^4)COR^5$.

In a further preferred embodiment, R is substituted by —$N(R^1)OCOaryl$.

In a further preferred embodiment, R is substituted by =$CHCO_2R^1$.

In a further preferred embodiment, R is substituted by =$CHCONR^1R^2$.

In a further preferred embodiment, R is substituted by =CHCN.

In a further preferred embodiment, R is substituted by =$NNHSO_2R^6$.

In a further preferred embodiment, R is substituted by —$N(O)$=$CHR^6$.

In a further preferred embodiment, R is substituted by —$OC(O)NR R^7$.

In a further preferred embodiment, R is substituted by amino$(C_1-C_6)$alkylarylCO$_2$—.

In a further preferred embodiment, R is substituted by —$OC(O)OR^8$.

The invention further provides a pharmaceutical composition for lightening skin or reducing the pigmentation of skin in a human, comprising a pharmaceutically acceptable carrier, and a skin-lightening or pigmentation-reducing effective amount of a compound of formula I wherein R is a $(C_3-C_8)$cycloalkyl or $(C_5-C_8)$cycloalkenyl ring substituted by =$CH_2$, with the proviso that the cycloalkenyl ring is not aromatic, or a pharmaceutically acceptable salt thereof.

In a preferred embodiment, R is a cycloalkyl ring, and preferably a cyclohexyl or cyclopentyl ring. Where R is a cyclohexyl or cyclohexenyl ring, the ring is preferably substituted at the 3- or 4-position, and more preferably at the 4-position. Where R is a cyclopentyl or cyclopentenyl ring, the ring is preferably substituted at the 3-position.

The invention further provides a pharmaceutical composition for lightening skin or reducing the pigmentation of skin in a human, comprising a pharmaceutically acceptable carrier, and a skin-lightening or pigmentation-reducing effective amount of a compound of formula I wherein R is 3-cyclohexenyl, which is preferably unsubstituted, or a pharmaceutically acceptable salt thereof.

The invention further provides a pharmaceutical composition for lightening skin or reducing the pigmentation of skin in a human, comprising a pharmaceutically acceptable carrier, and a skin-lightening or pigmentation-reducing effective amount of a compound of formula I, wherein R is a $(C_3-C_8)$cycloalkyl or $(C_5-C_8)$cycloalkenyl ring, wherein one of the carbon atoms of said cycloalkyl or cycloalkenyl rings is substituted by two groups such that the said groups are taken together with the carbon to which they are attached to form a ring of the formula:

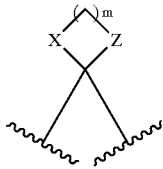

wherein X is O, S, SO, $SO_2$ or $NR^1$, wherein $R^1$ is as defined above; Z is $CH_2$, O, S, SO or $SO_2$; m is 0–3; with the proviso that when m=0, then Z is $CH_2$; and with the proviso that the cycloalkenyl ring is not aromatic; or a pharmaceutically acceptable salt thereof. In a preferred embodiment, m is 0. In a further preferred embodiment, m is 2. In a preferred embodiment, X and Z are both O. In a further preferred embodiment, X and Z are both S.

The invention further provides a pharmaceutical composition for lightening skin or reducing the pigmentation of skin in a human, comprising a pharmaceutically acceptable carrier, and a skin-lightening or pigmentation-reducing effective amount of a compound of formula I, wherein R is a $(C_3-C_8)$cycloalkyl or $(C_5-C_8)$cycloalkenyl ring, wherein one of the carbon atoms of said cycloalkyl or cycloalkenyl rings is substituted by two groups such that the said groups are taken together with the carbon to which they are attached to form a ring of the formula:

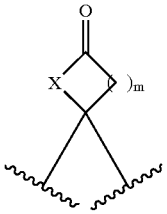

wherein X is O, S, SO, $SO_2$ or $NR^1$, wherein $R^1$ is as defined above; and m is 0–3; and with the proviso that the cycloalkenyl ring is not aromatic; or a pharmaceutically acceptable salt thereof. In a preferred embodiment, m is 2. In a further preferred embodiment, X is O.

In a preferred embodiment, the pharmaceutical composition of the present invention is adapted for topical application.

The invention further provides a pharmaceutical composition comprising a pharmaceutically acceptable carrier, and a skin-lightening or pigmentation-reducing effective amount of a compound selected from the group consisting of:

4-(1,4-Dioxaspiro[4.5]dec-8-yl)-1,3-benzenediol;

(±)-{4-[2,4-Dihydroxyphenyl]cyclohexylidene}acetic acid;

(±)-[4-(2,4-Dihydroxyphenyl)cyclohexylidene] acetonitrile;

cis-N-[4-(2,4-Dihydroxyphenyl)cyclohexyl]-N-hydroxybenzamide;

cis-N-[4-(2,4-Dihydroxyphenyl)cyclohexyl]benzamide;

trans-4-{4-[(Z)benzylidene(oxido)amino]cyclohexyl}-1,3-benzenediol;

trans-N-[4-(2,4-Dihydroxyphenyl)cyclohexyl]-N-hydroxybenzamide;

syn-8-(2,4-Dihydroxyphenyl)-1-oxaspiro[4.5]decan-2-one;

cis-N-[4-(2,4-Dihydroxyphenyl)cyclohexyl]-N'-phenylurea;

trans-Phenyl-4-(2,4-dihydroxyphenyl) cyclohexylcarbamate;

cis-N-Benzyl-N-[4-(2,4-dihydroxyphenyl)cyclohexyl]-N'-ethylurea;

cis-N-Benzyl-N-[4-(2,4-dihydroxyphenyl)cyclohexyl] propanamide;

trans-4-(2,4-Dihydroxyphenyl) cyclohexylphenylcarbamate;

trans-Ethyl[({[4-(2,4-dihydroxyphenyl)cyclohexyl] oxy}carbonyl)amino]acetate;

trans-4-(2,4-Dihydroxyphenyl)cyclohexyl benzylcarbamate;

trans-4-(2,4-Dihydroxyphenyl)cyclohexyl ethyl carbonate;

trans-Methyl[({[4-(2,4-dihydroxyphenyl)cyclohexyl] oxy}carbonyl)amino]acetate;

trans-4-(2,4-Dihydroxyphenyl)cyclohexyl methyl imidodicarbonate;

cis/trans-4-(1-Oxaspiro[2.5]oct-6-yl)-1,3-benzenediol;

4-(4-Methylenecyclohexyl)-1,3-benzenediol;

4-(3-Cyclohexen-1-yl)-1,3-benzenediol;

trans-4-(2,4-Dihydroxyphenyl)cyclohexyl (2R)-2-amino-3-phenylpropanoate;

Benzyl [4-(2,4-dihydroxyphenyl)cyclohexylidene] acetate;

4-(1,4-Dithiaspiro[4.5]dec-8-yl)-1,3-benzenediol;

N'-[4-(2,4-Dihydroxyphenyl)cyclohexylidene]-4-methylbenzenesulfonohydrazide;

trans-N-[4-(2,4-Dihydroxyphenyl)cyclohexyl]-3-nitrobenzamide;

trans-N-[4-(2,4-dihydroxyphenyl)cyclohexyl]-N'-phenylurea;

trans-N-[4-(dihydroxyphenyl)cyclohexyl]-2,2,2-trifluoroacetamide;

cis-3-cyano-N-[4-(2,4-dihydroxyphenyl)cyclohexyl]-N-hydroxybenzamide;

cis-N-[4-(2,4-dihydroxyphenyl)cyclohexyl]-N-hydroxy-4-(trifluoromethyl)benzamide;

cis-N-[4-(2,4-dihydroxyphenyl)cyclohexyl]-N-hydroxy-4-methoxybenzamide;

(±)-Methyl [4-(2,4-dihydroxyphenyl)cyclohexylidene] acetate;

and a pharmaceutically acceptable salt thereof.

The invention further provides a cosmetic composition comprising a cosmetically acceptable topical carrier in combination with any one or more of the compounds of formula I, or a cosmetically acceptable salt thereof.

The present invention further provides a method of lightening skin in a human, comprising administering to said human a skin-lightening or pigmentation-reducing effective amount of a compound of formula I, or a pharmaceutically acceptable salt thereof. In a preferred embodiment, the present invention provides a method of lightening skin in a human in need of said treatment, comprising administering to said human a skin-lightening effective amount of a compound of formula I, or a pharmaceutically acceptable salt thereof.

The present invention further provides a method of inhibiting tyrosinase in a human, comprising administering to said human a tyrosinase-inhibiting effective amount of a compound of formula I, or a pharmaceutically acceptable salt thereof. In a preferred embodiment, the present invention provides a method of inhibiting tyrosinase in a human in need of said treatment, comprising administering to said human a tyrosinase-inhibiting effective amount of a compound of formula I, or a pharmaceutically acceptable salt thereof.

The present invention further provides a topical or transdermal pharmaceutical composition for the treatment of an inflammatory disorder or condition such as psoriasis, dermatitis or acne, or for the treatment of dandruff, in a human in need of said treatment, comprising a pharmaceutically acceptable carrier, and an amount of a compound of formula I, or a pharmaceutically acceptable salt thereof, which amount is effective in treating such disorder or condition.

The present invention further provides a method of treating an inflammatory disorder, such as psoriasis, dermatitis or acne, or a method of treating dandruff, in a human in need of said treatment, comprising administering to said human an amount of a compound of formula I, or a pharmaceutically acceptable salt thereof, which amount is effective in treating such disorder or condition.

The present invention further provides a kit, comprising a container comprising one or more specific compounds or pharmaceutically acceptable salts thereof, or pharmaceutical compositions, of the present invention that lighten skin. The kit may further comprise printed instructions as a label or package insert directing the use of the enclosed compound or composition to lighten skin pigmentation.

As used herein, the terms "treat" and "treating", and the like, refer to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "alkyl", as used herein, unless otherwise indicated, includes saturated monovalent hydrocarbon radicals having straight, branched or cyclic moieties or combinations thereof. Any substituents or functional groups on the alkyl group, as indicated herein, can be substituted anywhere on the alkyl group.

The term "alkenyl", as used herein, unless otherwise indicated, includes unsaturated hydrocarbon radicals having straight, branched or cyclic moieties or combinations thereof, with one or more, and preferably one or two, double bonds. Any substituents or functional groups on the alkyl group, as indicated herein, can be substituted anywhere on the alkenyl group.

The term "aryl", as used herein, refers to a $(C_5-C_{10})$ aryl, preferably phenyl or naphthyl, optionally substituted with one or more substituents, and preferably one or two substituents, independently selected from halogen, OH, $(C_1-C_6)$alkyl, amino, $(C_1-C_6)$alkylamino-, di-$((C_1-C_6)$alkyl))amino-, —$NR^1COR^1$ wherein each $R^1$ is independently selected from the group described above, nitro, cyano, —X—$(C_1-C_6)$alkyl, —X—$(C_1-C_6)$alkylaryl, —X-aryl, where X is defined above, trifluoromethyl, —$OCF_3$, —$CO(C_1-C_6)$alkyl, —COaryl, —$COCF_3$, —$CONR_{12}$, $(C_2-C_7)$alkenyl, aryl, $(C_3-C_9)$heterocycloalkyl, and $(C_5-C_{10})$heteroaryl. Any substituents or functional groups on the aryl group, as indicated herein, can be substituted anywhere on the aryl group.

The term "one or more substituents", as used herein, refers to a number of substituents that equals from one to the maximum number of substituents possible based on the number of available bonding sites.

The term "halogen" as used herein, unless otherwise indicated, refers to chlorine, fluorine, bromine and iodine.

The term "heteroaryl", as used herein, refers to a $(C_2-C_{10})$ heteroaryl, more preferably a $(C_5-C_{10})$heteroaryl, and more preferably a 5- or 6-membered heteroaryl, containing one to five N, O or S atoms. In a preferred embodiment, the heteroaryl is selected from furyl, thienyl, thiazolyl, pyrazolyl, isothiazolyl, oxazolyl, isoxazolyl, pyrrolyl, triazolyl, tetrazolyl, imidazolyl, oxadiazolyl, thiadiazolyl, pyridyl, pyrimidinyl, pyrazinyl, pyridazinyl, triazinyl, pyrazolo[3,4-b]pyridinyl, pyrazolo[1,5-a]pyrimidinyl, cinnolinyl, pteridinyl, purinyl, benzo[b]thiophenyl, 5,6,7,8-tetrahydro-quinolin-3-yl, 6,7-dihydro-5H-[1]pyridinyl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolinyl, quinolinyl, phthalazinyl, quinoxalinyl, quinazolinyl, benzoxazinyl, 4-oxo-1,4-dihydro[1,8]naphthyridin-3-yl, benzo[1,3]dioxol-5-yl, and 4-oxo-6,7-dihydro-5H-benzofuryl. One of ordinary skill in the art will understand that the connection of said $(C_2-C_9)$heteroaryl ring can be through a carbon atom or through a nitrogen heteroatom where possible.

The heteroaryl may be optionally substituted with one or more substituents, preferably one or two substituents, independently selected from halogen, OH, $(C_1-C_6)$alkyl, —$(C_1-C_6)$alkoxy, amino, $(C_1-C_6)$alkylamino-, di-$((C_1-C_6)$alkyl))amino-, —$NR^1COR^1$ wherein each $R^1$ is independently selected from the group described above, nitro, cyano, —X—$(C_1-C_6)$alkyl, —X-aryl, where X is defined above, trifluoromethyl, —$OCF_3$, —$S(O)_p(C_1-C_6)$alkyl where p is 0, 1 or 2, —COaryl, —$COCF_3$, —$CO(C_1-C_6)$alkyl, —$(C_1-C_6)$alkylOH, —$COOR^1$, —$(C_1-C_6)$alkylCOOR$^1$, —$CONR^1_2$, $(C_2-C_7)$alkenyl, —CONH$(CHR^1)_qCO_2R^1$ where q is 1 or 2, —$CONR^1N(R^1)_2$, aryl, —$(C_1-C_6)$alkylaryl, $(C_3-C_9)$heterocycloalkyl, $(C_5-C_{10})$heteroaryl, and —$(C_1-C_6)$alkyl$(C_2-C_9)$heteroaryl. Any substituents or functional groups on the heteroaryl group, as indicated herein, can be substituted anywhere on the heteroaryl group.

The term "heterocycloalkyl", as used herein, refers to a $(C_2-C_{10})$heterocycloalkyl, more preferably a $(C_5-C_{10})$ heterocycloalkyl, and more preferably a 5- or 6-membered heterocycloalkyl, containing from one to five N, O or S atoms. In a preferred embodiment, the heterocycloalkyl group is selected from pyrrolidinyl, dihydropyrrolindinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, oxazolidinyl, isothiazolidinyl, thiazolidinyl, pyrazolidinyl, piperidinyl, thiomorpholinyl, tetrahydrothiazinyl, thiadiazinyl, -tetrahydrothiadiazinyl, morpholinyl, tetrahydrodiazinyl, tetrahydroazepinyl, piperazinyl, chromanyl, oxopyrrolidinyl, 1,3-dioxo-1,3-dihydroisoindolyl, 6-oxo-1,4,5,6,-tetrahydropyridazin-4-yl, 2,3-dihydrobenzo[1,4]dioxin-2-yl, 2-oxo-2H-chromen-5-yl, benzo[1,3]dioxol-5-yl, and 3-oxo-3H-isobenzofuran-1-ylidinemethyl. One of ordinary skill in the art will understand that the connection of said heterocycloalkyl ring can be through a carbon atom or through a nitrogen heteroatom where possible.

The heterocycloalkyl may be optionally substituted with one or more substituents, preferably one or two substituents, independently selected from halogen, OH, —($C_1$-$C_6$)alkyl, —($C_1$-$C_6$)alkoxy, —S(O)$_p$($C_1$-$C_6$)alkyl where p is 0, 1 or 2, amino, =O, ($C_1$-$C_6$)alkylamino, di-(($C_1$-$C_6$)alkyl))amino, $NR^1COR^1$ wherein each $R^1$ is independently selected from the group described above, —$COOR^1$, —($C_1$-$C_6$)alkyl$COOR^1$, —$CONH(CHR^1)_qCO_2R^1$ where q is 1 or 2, —$CONR^1N(R^1)_2$, —($C_1$-$C_6$)alkylOH, —CO($C_1$-$C_6$)alkyl, nitro, cyano, —X—($C_1$-$C_6$)alkyl, —X-aryl, where X is defined above, trifluoromethyl, —$OCF_3$, —COaryl, —$COCF_3$, —CO($C_1$-$C_6$)alkyl, —$CONR^1_2$, ($C_2$-$C_7$) alkenyl, ($C_1$-$C_6$)alkylaryl, aryl, ($C_3$-$C_9$)heterocycloalkyl, ($C_5$-$C_{10}$)heteroaryl, and —$CO_2$($C_1$-$C_6$)alkyl. Any substituents or functional groups on the aryl group, as indicated herein, can be substituted anywhere on the aryl group. In a preferred embodiment, the heterocycloalkyl group is substituted with one or more substituents, preferably one or two substituents, independently selected from halogen, OH, —($C_1$-$C_6$)alkyl, amino, and trifluoromethyl. Any substituents or functional groups on the heterocycloalkyl group, as indicated herein, can be substituted anywhere on the aryl group.

Compounds of formula I may contain chiral centers and therefore may exist in different enantiomeric and diastereomeric forms. This invention relates to all optical isomers, stereoisomers and tautomers of the compounds of formula I, II and III, and mixtures thereof, and to all pharmaceutical compositions and methods of treatment defined above that contain or employ them, respectively.

Formula I, as defined above, also includes compounds identical to those depicted but for the fact that one or more hydrogen, carbon or other atoms are replaced by isotopes thereof. Such compounds may be useful as research and diagnostic tools in metabolism pharmacokinetic studies and in binding assays.

The present invention also relates to the pharmaceutically acceptable acid addition and base salts of any of the aforementioned compounds of formula I. The acids that are used to prepare the pharmaceutically acceptable acid addition salts of the aforementioned base compounds of this invention are those that form non-toxic acid addition salts, i.e., salts containing pharmacologically acceptable anions, such as the hydrochloride, hydrobromide, hydroiodide, nitrate, sulfate, bisulfate, phosphate, acetate, lactate, citrate, tartrate, bitartrate, succinate, maleate, fumarate, gluconate, saccharate, benzoate, methanesulfonate, ethanesulfonate, benzenesulfonate p-toluenesulfonate and pamoate (i.e., 1,1-methylene-bis-(2-hydroxy-3-naphthoate)) salts.

As used herein, a "skin-lightening or pigmentation reducing amount of a compound of formula I", and the like, means an amount or concentration of the compound capable of detectably lightening skin or reducing pigmentation in a human, as determined by any standard assay. The active compound is typically administered in a pharmaceutical composition and for a standard course of treatment that produces the desired result of skin depigmentation.

As used herein, a "tyrosinase-inhibiting effective amount of a compound of formula I", and the like, means an amount or concentration of the compound capable of detectably inhibiting tyrosinase activity in a human, as determined by any standard assay, such as those described below.

As used herein, an "amount of a compound of formula I capable of treating an inflammatory disorder such as psoriasis, dermatitis or acne, or treating dandruff", and the like, means an amount or concentration of the compound capable of detectably ameliorating, reducing, eliminating, slowing, or preventing the progression of, any symptom or condition associated with or caused by such disorder or condition, in a human, as determined by any standard assay.

DETAILED DESCRIPTION OF THE INVENTION

The compounds of formula I may be prepared as described in the following reaction schemes and discussion. Unless otherwise indicated m, $R^6$, X, Z and structural formula I in the reaction schemes and discussion that follow are as defined above, and n=0–5.

Scheme 1

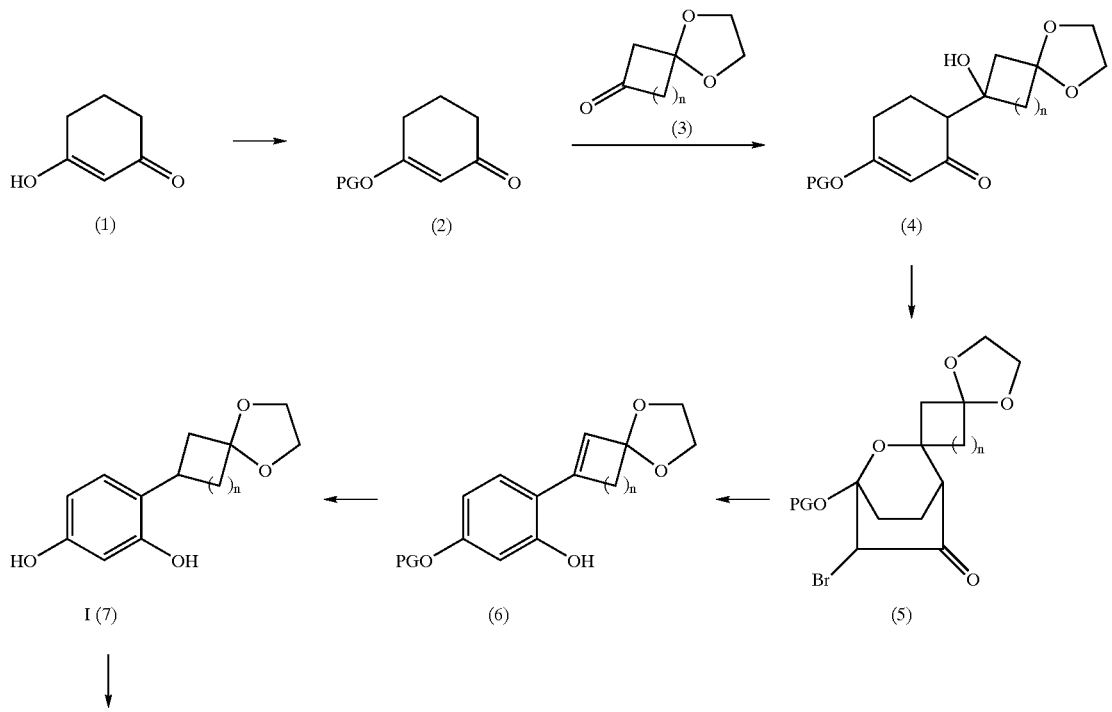

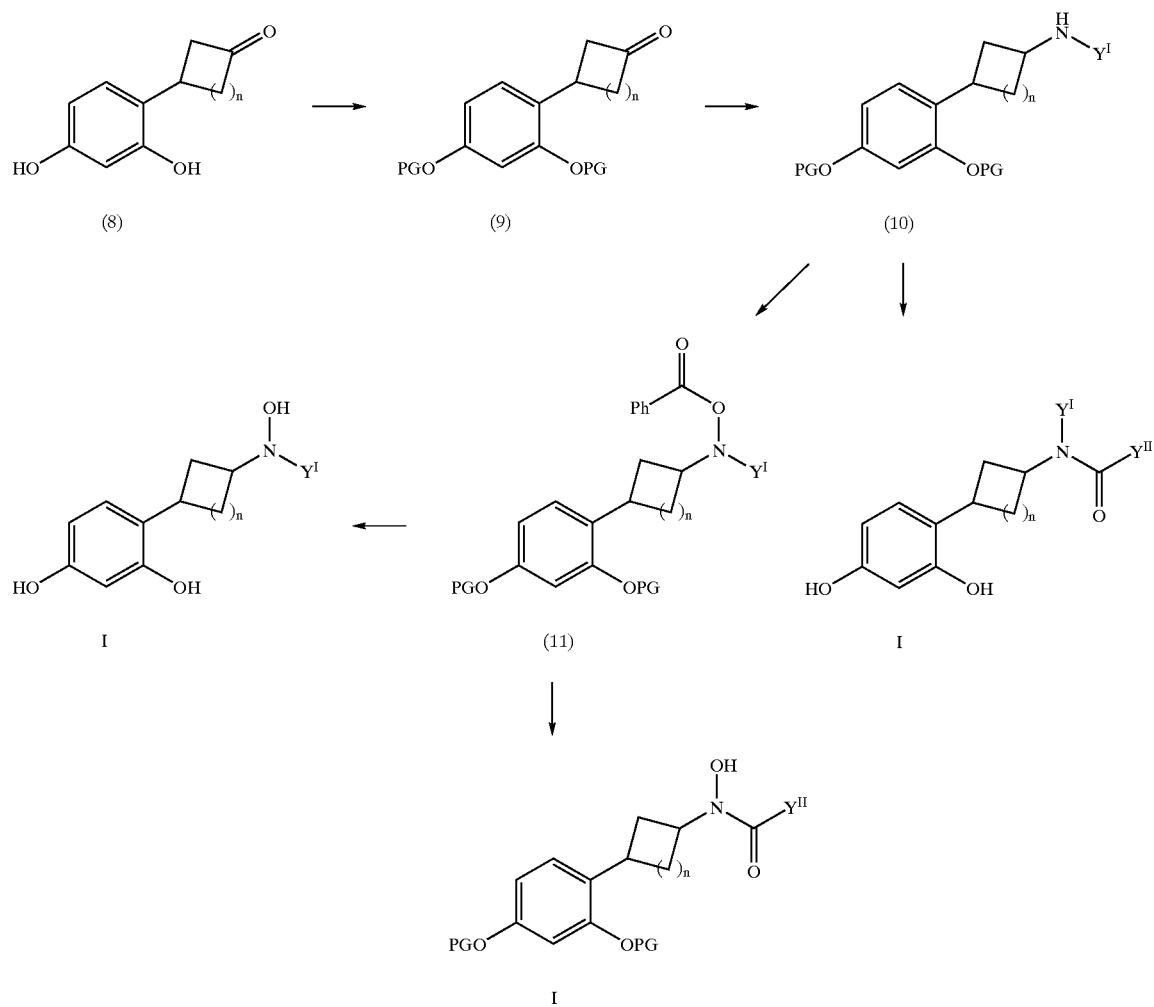
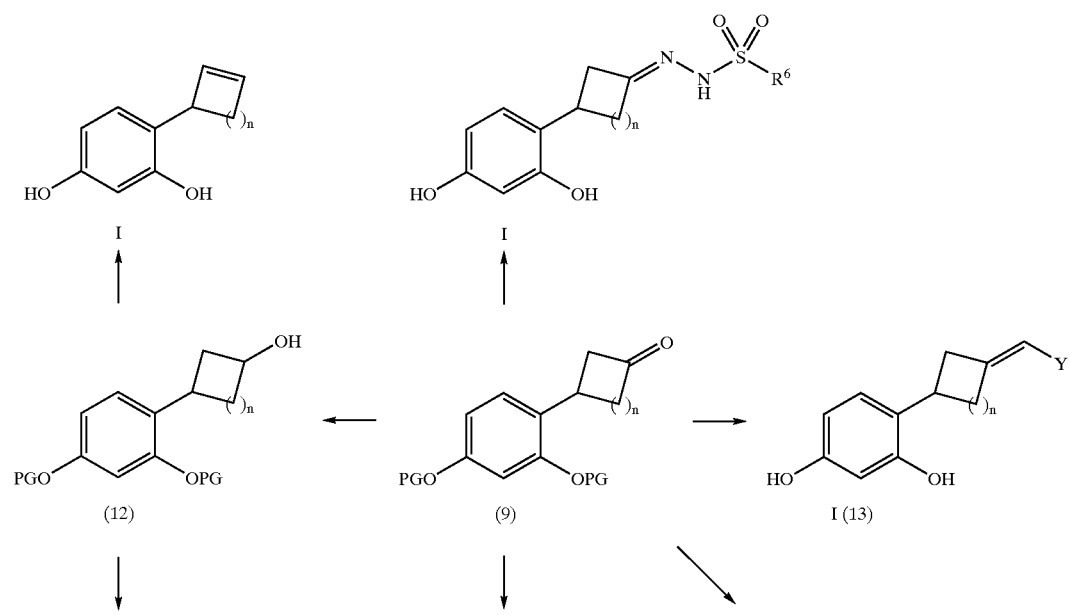
Scheme 2

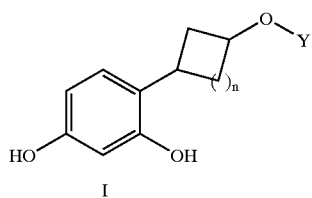
I

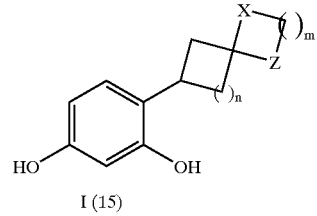
I (15)

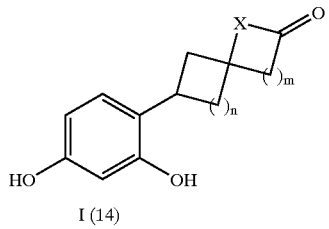
I (14)

Scheme 3

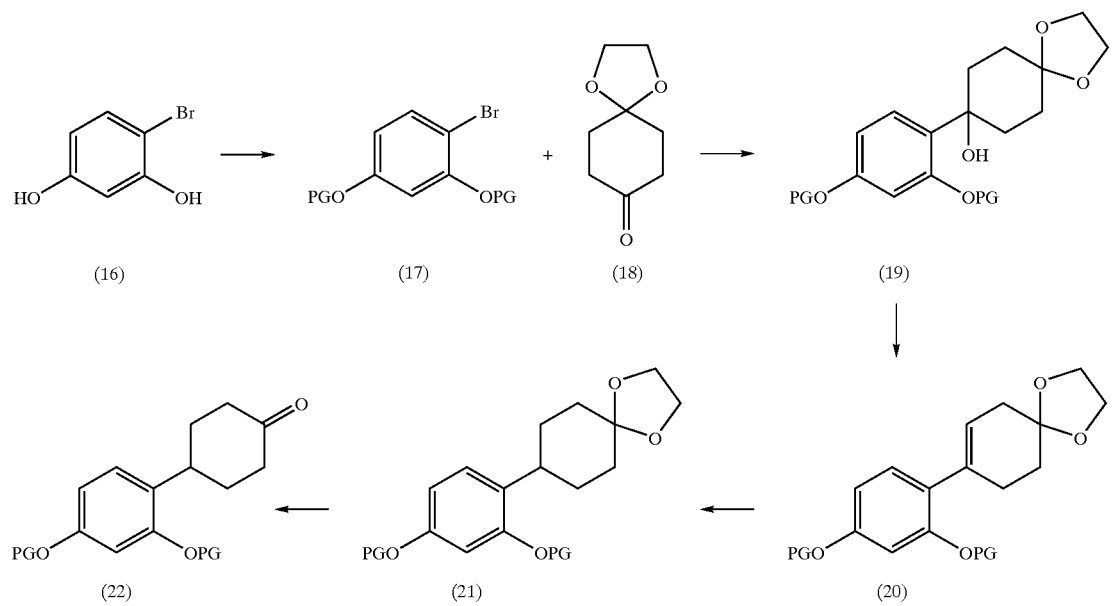

Y, Y$^I$, Y$^{II}$ shown in the schemes above each independently represents any of the components of the various substituents on R as defined above, or hydrogen as appropriate.

Referring to Scheme 1, compounds of formula (2) can be prepared starting with compound (1), which is commercially available (Aldrich, Milwaukee, Wis., USA). Conversion into compounds of formula (2) can occur under standard conditions, for example, where the protecting group is benzyl, condensation can occur between compound (1) and benzyl alcohol with the removal of water using a Dean-Stark apparatus in conjunction with well-known methodology. Condensation of compounds of formula (2) with compounds of formula (3) can occur using standard techniques, for example, treatment of compounds of formula (2) with a base such as lithium diisopropylamide in an ethereal solvent followed by the addition of a compound of formula (3) at low temperature would give compounds of formula (4). Compound (3) where n=3 is commercially available (Aldrich, Milwaukee, Wis., USA). Treatment of compounds of formula (4) with a suitable halogenating reagent such as N-bromosuccinimide in a chlorinated solvent at about room temperature can give compounds of formula (5). Compounds of formula (6) can then be generated from compounds of formula (5) under suitable conditions. Such conditions can involve treating compounds of formula (5) with a base such as 1,8-diazobicyclo[5.4.0]undec-7-ene in a suitable solvent such as N,N-dimethylformamide at about 140° C. Treatment of compounds of formula (6) to standard hydrogenation conditions, e.g., hydrogen gas and palladium on charcoal in ethanol, yields compounds of the general formula 1 (7) when the protecting group is benzyl. Compounds of formula (8) can then be obtained by treating compounds of formula (7) to acidic conditions.

Conversion of compounds of formula (8) into compounds of formula I may involve the need to use protecting groups that will be obvious to those of skill in the art. Compounds of formula (9), where PG is a suitable protecting group, can be manipulated through several steps to give compounds of formula I where R is substituted with an amide, urea, hydroxylamine or hydroxamic acid. An example of a suitable protecting group is tert-butyldimethylsilyl. Treatment of compounds of formula (8) with tert-butyldimethylsilyl chloride in a suitable solvent, e.g., DMF, in the presence of a suitable base such as imidazole, at about room temperature, will give compounds of formula (9). Treatment of compounds of formula (9) with benzylamine under reductive amination conditions, e.g., sodium triacetoxyborohydride in a suitable solvent, e.g., dichloroethane, will give compounds of formula (10). For compounds of formula I where Y$^I$=H, hydrogenolysis under standard conditions, e.g., palladium on charcoal, hydrogen gas, ethanol, followed by amide bond formation, e.g., using an acid chloride in the presence of a suitable base such as triethylamine, provides compounds of formula I after suitable deprotection. When PG is tert-butyldimethylsilyl, suitable deprotection may involve the use of tetrabutylammonium fluoride in a suitable solvent such as THF, at about room temperature. Alternatively, amides can be prepared from compounds of formula (10) using an acid and a suitable coupling reagent, which are well known to those with skill in the art. One such suitable coupling reagent is O-(7-azabenzotriazol-1-yl)-N,N,N',N'-tetramethyluronium hexafluorophosphate used in the presence of a base such as diisopropylamine at about room temperature. Compounds where R is substituted with a urea may be formed from compounds of formula (10) using standard conditions, e.g., an isocyanate and a base such as diisopropylamine in DCM at about 40° C. Compounds where R is substituted with a hydroxylamine or hydroxamic acid, can be synthesised from compounds of formula (10) by treatment with benzoylperoxide in a suitable solvent such as DCM, at about room temperature, to give compounds of formula (11). Treatment of compounds of formula (11), where $Y'$=H, with an acid chloride in the presence of a base, such as triethylamine, in a chlorinated solvent, after suitable deprotection and treatment with a base such as 2M NaOH at about room temperature, would give compounds of formula I where R is substituted with a hydroxamic acid. Treatment of compounds of formula (11) to suitable deprotection followed by treatment with a base such as 2M NaOH at about room temperature, would give compounds of formula I where R is substituted with a hydroxylamine.

Referring to scheme 2, compounds of formula (9) can be derivatised to yield compounds of formula I (13) using standard Wittig or Wadworths-Emmons chemistry known to those of skill in the art. For example, when Y=CN, treating diethylcyanomethyl-phosphonate with a suitable base, e.g., sodium hydride, in a suitable solvent, e.g., dimethoxyethane, followed by a compound of formula (9), would give, after suitable deprotection, compounds of formula 1 (13). Compounds of formula (9) may also be reduced under standard conditions, e.g., sodium borohydride in ethanol at about room temperature, to give compounds of formula (12). Compounds of formula (12) may then be further derivatised to give compounds of formula I where Y is an amino acid using conventional coupling methods. Such methods may involve the use of an acid chloride, and base such as triethylamine in a suitable solvent such as dichloromethane. Treatment of compounds of formula (12) with sodium hydride and a suitable chloroformate reagent would give compounds of formula I where R is substituted with a carbonate. Treatment of compounds of formula (12) with an isocyanate and base, e.g., diisoproylamine, in a suitable solvent, e.g., DMF, at about 50° C., after deprotection, would give compounds of formula I where R is substituted with a carbamate. Compounds of formula I where R=cyclohexenyl may be produced from compounds of formula (12) under dehydrating conditions. Such conditions may involve treating a compound of formula (12) with (diethylamino)sulfur trifluoride in a solvent such as DCM, at about room temperature.

Compounds of formula I (14), where X=O and m=2, may be prepared from compounds of formula (9). Treatment of compounds of formula (14) with samarium diiodide and ethylacrylate in a suitable solvent such as THF gives, after suitable deprotection, compounds of formula 1 (14). Where R is substituted with =NNHSO$_2$R$^6$, heating compounds of formula (9) with the appropriate sulfonyl hydrazide in a solvent such as ethanol gives, after suitable deprotection, compounds of formula 1. Compounds of formula I (15) may be synthesised from compounds of formula (9) under standard conditions, for example, where X and Z are S, and m is 2, treating compounds of formula (9) with propanedithiol and an acid, e.g., para-toluene sulfonic acid, under dehydrating conditions, followed by suitable deprotection.

Referring to Scheme 3, compounds of formula (17) can be formed by protecting commercially available 4-bromoresorcinol (16) (Aldrich Chemical Company). A suitable protecting group such as methoxymethyl (MOM) can be introduced by conventional methods that are well known to those skilled in the art. For example, alkylation of 4-bromoresorcinol can occur with two equivalents of methoxymethyl chloride in the presence of diisopropylamine in a halogenated solvent at about 0° C. to room temperature. The compound of the formula (18) is commercially available (Aldrich Chemical Company). Compounds of formula (19) can be obtained from the reaction of compounds of formula (17) with n-butyllithium in the presence of N,N,N',N'-tetramethylethylenediamine in an ethereal solvent, followed by the addition of a compound of formula (18). Dehydration of compounds of formula (19) under standard conditions, e.g., heating compounds of formula (19) at about 110° C. in a Dean-Stark apparatus in the presence of camphor sulfonic acid in a suitable solvent (e.g., toluene), yields compounds of formula (20). Hydrogenation under standard conditions, e.g., using hydrogen gas and palladium on charcoal in ethanol, yields compounds of the general formula (21) and hydrolysis, e.g., aqueous hydrochloric acid at about room temperature, yields compounds of formula (22).

It will be appreciated by those of skill in the art that in the processes described above, the functional groups of intermediate compounds may need to be protected by protecting groups. The use of protecting groups is well-known in the art, and is fully described, among other places, in: *Protecting Groups in Organic Chemistry*, J. W. F. McOmie, (ed.), 1973, Plenum Press; and in: *Protecting Groups in Organic Synthesis*, 2$^{nd}$ edition, T. W. Greene & P. G. M. Wutz, 1991, Wiley-Interscience, which are incorporated by reference in their entirety.

The compounds of formula I that are basic in nature are capable of forming a wide variety of different salts with various inorganic and organic acids. Although such salts must be pharmaceutically acceptable for administration to animals, it is often desirable in practice to initially isolate a compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of formula I that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of this invention are those that form non-toxic base salts with the acidic compounds of formula I. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness, as described above. In either case, stoichiometric quantities of reagents are preferably employed in order to ensure completeness of reaction and maximum yields of the desired final products.

Compounds of formula I and their pharmaceutically acceptable salts (hereinafter "the active compounds used in this invention") are useful in the treatment of disorders of human pigmentation, including solar and simple lentigines (including age/liver spots), melasma/chloasma and postinflammatory hyperpigmentation. The active compounds used in this invention reduce skin melanin levels by inhibiting the production of melanin, whether the latter is produced constitutively or in response to UV irradiation (such as sun exposure). Thus, the active compounds used in this invention can be used to reduce skin melanin content in nonpathological states so as to induce a lighter skin tone, as desired by the user, or to prevent melanin accumulation in skin that has been exposed to UV irradiation. Thus, the active compounds used in this invention can be used simply to lighten skin where no pathological or disease condition exists. The active compounds used in this invention can also be used for cosmetic purposes. As used herein to refer to the depigmentation aspect of the invention, the term "a human in need of said treatment" refers to a human who, for any reason, whether medical or cosmetic, desires to reduce the melanin content of their skin or to prevent the melanization of their skin on any portion of their body.

The compounds of this invention can be prepared as cosmetics, quasi-drugs (where applicable), or pharmaceutical drugs. As cosmetics, the compounds of the present invention are useful in improving overall skin tone and texture.

The compounds of this invention can appropriately be combined with other components. Examples of such components include oily components such as hydrocarbons, fats and oils such as liquid paraffin, squalene, vaseline, cetyl alcohol, isostearyl alcohol, cetyl-2-ethylhexanoate, 2-octyldodecyl alcohol, glycerin triiostearate, nut oils, and lanolin, as well as wax, silicone, surfactants, thickeners, neutralizers, antiseptics, germicides, anti-oxidants, powder components, pigments, perfumes, ultraviolet light absorbents, drugs, metallic sealant, and pH modifiers. Thus, cosmetics, quasi-drugs (where applicable), and pharmaceutical drugs of the present invention can be prepared using dermatologically, cosmetically or pharmaceutically acceptable carriers as appropriate, and as known in the art.

Occurrences in the skin or hair of noticeable but undesired pigmentation as a result of melanin production, overproduction or underproduction can be treated using the methods of the present invention. Cosmetic applications for methods of the present invention include the topical application of compositions containing one or more of the compounds of the present invention to enhance or otherwise alter the visual appearance of skin or hair. The cosmetic compositions of the present invention are also useful to provide a smoother or softer skin appearance or texture.

The active compounds used in this invention can also be used in combination with skin peeling agents (including glycolic acid or trichloroacetic acid face peels) to lighten skin tone and prevent repigmentation. The appropriate dose regimen, the amount of each dose administered, and specific intervals between doses of the active compound will depend upon the particular active compound employed, the condition of the patient being treated, and the nature and severity of the disorder or condition being treated. Preferably, the active compound is administered in an amount and at an interval that results in the desired treatment of or improvement in the disorder or condition being treated.

An active compound used in this invention can also be used in combination with sun screens (UVA or UVB blockers) to prevent repigmentation, to protect against sun or UV-induced skin darkening or to enhance their ability to reduce skin melanin and their skin bleaching action. An active compound used in this invention can also be used in combination with retinoic acid or its derivatives or any compounds that interact with retinoic acid receptors and accelerate or enhance the invention's ability to reduce skin melanin and skin bleaching action, or enhance the invention's ability to prevent the accumulation of skin melanin. An active compound used in this invention can also be used in combination with 4-hydroxyanisole.

An active compound used in this invention can also be used in combination with ascorbic acid, its derivatives and ascorbic-acid based products (such as magnesium ascorbate) or other products with an anti-oxidant mechanism (such as resveratrol) which accelerate or enhance their ability to reduce skin melanin and their skin bleaching action.

As one skilled in the art would know in view of this disclosure, an active compound used in the methods of the present invention may be used alone or in combination with other compounds known in the art to affect melanin synthesis, particularly other melanin synthesis inhibitors, including tyrosinase inhibitors. Such inhibitors include those currently known in the art and those to be developed in the future. Known inhibitors include various resorcinol derivatives, kojic acid derivatives, hydroquinone, melamine, and various types of plant extracts, among others. For example, any of the compounds used according to a skin-lightening method of the present invention may be used in combination with a tyrosinase inhibitor or other skin-whitening agent, including any one or more of those agents, including compounds or extracts, described in the following patent publications: U.S. Pat. No. 4,278,656 to Nagai et al, issued Jul. 14, 1981, describing the use of kojic acid and its derivatives; U.S. Pat. No. 4,369,174 to Nagai et al., issued Jan. 18, 1983, describing the use of kojic acid and its derivatives; U.S. Pat. No. 4,959,393 to Torihara et al., issued Sep. 25, 1990, describing the use of 4-n-butylresorcinol, 4-isoamyl resorcinol and other resorcinol derivatives; U.S. Pat. No. 5,580,549 to Fukuda et al., issued Dec. 3, 1996, describing the use of various hydroxybenzoic acid derivatives; U.S. Pat. No. 6,123,959 to Jones et al., issued Sep. 26, 2000, describing the use of liposomes containing combinations of competitive inhibitors, such as arbutin, and non-competitive inhibitors, such as aloesin, of melanin synthesis; U.S. Pat. No. 6,132,740 to Hu, issued Oct. 17, 2000, describing the use of various resorcinol derivatives; U.S. Pat. No. 6,159,482 to Tuloup et al., issued Dec. 12, 2000, describing the use of various hydroxyphenyl oxamate derivatives; WO 99/32077 by L'Oreal, published Jul. 1, 1999, describing the use of various phenolic amides; WO 99/64025 by Fytokem Prod. Inc., published Dec. 16, 1999, describing the use of various dicotyledonous plant extracts; WO 00/56702 by Pfizer Inc., published Sep. 28, 2000 describing various resorcinol derivatives; WO 00/76473 by Shiseido Co. Ltd., published Dec. 12, 2000, describing the use of Withania plant extracts; EP 997140 by L'Oreal SA, published May 3, 2000, describing the use of combinations of mulberry and skullcap extracts with salicylic acid derivatives; JP 5221846 by Kunimasa Tomoji, published Aug. 31, 1993, describing the use of kojic acid derivatives; JP 7242687 by Shiseido Co. Ltd., published Sep. 19, 1995, describing the use of Trichoderma extracts; JP 7324023 by Itogawa H, published Dec. 12, 1995, describing, the use of *Pseudostellariae radix* extracts; JP 8012552 by Shiseido Co. Ltd., published Jan. 16, 1996, describing the use of Amor seco extracts; JP 8012554 by Shiseido Co. Ltd., published Jan. 16, 1996, describing the use of Jabonciilo extracts; JP 8012557 by Shiseido Co. Ltd., published Jan. 16, 1996, describing the use of Huaca extracts; JP 8012560 by Shiseido Co. Ltd., published Jan. 16, 1996, describing the use of Copaiba extracts; JP 8012561 by Shiseido Co. Ltd., published Jan. 16, 1996, describing the use of Arnica extracts; JP 8134090 by Fujisawa, published May 28, 1996, describing the use of galactosyl-kojic acid derivatives; JP,8168378 by Kirinjo KK, published Jul. 2, 1996, describing the use of lees from rice wine production; JP 8277225 by Kansai Koso KK, published Oct. 22, 1996, describing the use of *Autocarpus incisus* extracts; JP 9002967 by Sanki Shoji KK, published Jan. 7, 1997, describing the use of *Prunus domesticus* extracts; JP 9295927 by Yagi Akira, published Nov. 18, 1997, describing the use of *Aloe vera* extracts; JP 10072330 by Kansai Kouso, published Mar. 17, 1998, describing the use of oxydesberatrdl derivatives; JP 10081626 by Kamiyama KK, published Mar. 31, 1998, describing the use of 4-substituted benzoic acids; JP 10101543 by Kansai Kouso KK, published Apr. 21, 1998, describing the use of flavonoids; JP 11071231 by Maruzen Pharm., published Mar. 16, 1999, describing the use of bakuchiol; JP 11079934 by Kyodo Nyugyo, published Mar. 23, 1999, describing the use of low molecular weight thiol from sake lees; JP 11246347 by Shiseido Co. Ltd., published Sep. 14, 1999, describing the use of *Achillea millefolium* extracts; JP 11246344 by Shiseido Co. Ltd., published Sep. 14, 1999, describing the use of Gliricidia extracts; JP 2000–080023 by Kanebo Ltd., published Mar. 21, 2000, describing the use of metallothionine inducers; JP 2000–095663 by Kose KK, published Apr. 4, 2000, describing the use of various plant extracts; JP 2000–159681 by Hai Tai Confectionary Co. Ltd., published Jun. 13, 2000, describing the use of grape seed extract; JP-7206753 by Nikken Food KK, published Aug. 8, 1995, describing the use of dihydroxycurcumin derivatives; JP-5320025 by Kunimasa T, published Dec. 3, 1993, describing the use of kojic acid derivatives; and JP-59157009 by Yakurigaku Chuou K E, published Sep. 6, 1984, describing the use of β-thujaplicin, hydroquinone or a pyrone compound in combination with a melanin adsorbent; among others; which patent publications are incorporated herein by reference in their entireties.

This invention relates both to methods of lightening or reducing the pigmentation of skin in which an active compound used in this invention, and one or more of the other active ingredients, such as those referred to above, are administered together as part of the same pharmaceutical composition, as well as methods in which they are administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and the nature and severity of the disorder or condition being treated. Such additional active ingredients will generally be administered in amounts less than or equal to those for which they are effective as single topical therapeutic agents. The FDA approved dosages for such active agents that have received FDA approval for administration to humans are publicly available.

An active compound of this invention will generally be administered in the form of a pharmaceutical composition comprising at least one compound of formula (I), together with a pharmaceutically acceptable vehicle or diluent. Alternatively, an active compound of this invention can be administered in the form of a cosmetic composition comprising at least one compound of formula (1), together with a cosmetically acceptable vehicle or diluent. Such a composition is generally formulated in a conventional manner utilizing solid or liquid vehicles or diluents as appropriate for topical administration, in the form of solutions, gels, creams, jellies, pastes, lotions, ointments, salves, aerosols and the like.

Examples of vehicles for application of the active compounds of this invention include an aqueous or water-alcohol solution, an emulsion of the oil-in-water or water-in-oil type, an emulsified gel, or a two-phase system. Preferably, the compositions according to the invention are in the form of lotions, creams, milks, gels, masks, microspheres or nanospheres, or vesicular dispersions. In the case of vesicular dispersions, the lipids of which the vesicles are made can be of the ionic or nonionic type, or a mixture thereof. Such vehicles can include suitable viscosity enhancing agents, pH adjusting agents, stabilizers, fragrances, etc., as known in the art of topical formulations.

An effective dosage and treatment protocol can be determined by conventional means, starting with a low dose in laboratory animals and then increasing the dosage while monitoring the effects, and systematically varying the dosage regimen as well. Animal studies, preferably mammalian studies, are commonly used to determine the maximal tolerable dose, or MTD, of a bioactive agent per kilogram weight. Those skilled in the art can extrapolate doses for efficacy and avoidance of toxicity to other species, including humans.

Before human studies of efficacy are undertaken, Phase I clinical studies in normal subjects can help establish safe doses. Numerous factors can be taken into consideration by a clinician when determining an optimal dosage for a given subject. Primary among these is the toxicity and half-life of the chosen compound. Additional factors include the size of the patient, the age of the patient, the general condition of the patient, the particular disease, condition, or disorder being treated, the severity of the disease, condition, or disorder being treated, the presence of other drugs in the patient, the effect desired, and the like. The trial dosages would be chosen after consideration of the results of animal studies and the clinical literature.

One of ordinary skill in the art will appreciate that the endpoint of treatment chosen in a particular case will vary according to the disease, condition, or disorder being treated, the outcome desired by the patient, subject, or treating physician, and other factors. Where the composition is being used to lighten skin color such as, for example, to reverse hyperpigmentation caused by, for example, inflammation or diseases such as melasma, or to lighten hair color, any one of a number of endpoints can be chosen. For example, endpoints can be defined subjectively such as, for example, when the subject is simply "satisfied" with the results of the treatment. For pharmacological compositions, the endpoint can be determined by the patient's, or the treating physician's, satisfaction with the results of the treatment Alternatively, endpoints can be defined objectively. For example, the patient's or subject's skin or hair in the treated area can be compared to a color chart. Treatment is terminated when the color of the skin or hair in the treated area is similar in appearance to a color on the chart. Alternatively, the reflectance of the treated skin or hair can be measured, and treatment can be terminated when the treated skin or hair attains a specified reflectance. Alternatively, the melanin content of the treated hair or skin can be measured. Treatment can be terminated when the melanin content of the treated hair or skin reaches a specified value. Melanin content can be determined in any way known to the art, including by histological methods, with or without enhancement by stains for melanin.

In the depigmenting compositions according to the present invention, the concentration of the active compound of the invention is generally between 0.01 and 10%, preferably between 0.1 and 10%, relative to the total weight of the composition.

The compositions of this invention can optionally also contain a moistener, a surfactant, keratolytic, an anti-inflammatory agent, a complexing agent, an antioxidant, a preservative, a colorant, a fragrance, or a sunscreen.

The compositions of the present invention can be applied directly to the skin. Alternatively, they can be delivered by various transdermal drug delivery systems, such as transdermal patches as known in the art. For example, for topical administration, the active ingredient can be formulated in a solution, gel, lotion, ointment, cream, suspension, paste, liniment, powder, tincture, aerosol, patch, or the like in a pharmaceutically or cosmetically acceptable form by methods well known in the art. The composition can be any of a variety of forms common in the pharmaceutical or cosmetic arts for topical application to animals or humans, including solutions, lotions, sprays, creams, ointments, salves, gels, etc., as described below. Preferred agents are those that are viscous enough to remain on the treated area, those that do not readily evaporate, and/or those that are easily removed by rinsing with water, optionally with the aid of soaps, cleansers and/or shampoos. Actual methods for preparing topical formulations are known or apparent to those skilled in the art, and are described in detail in *Remington's Pharmaceutical Sciences*, 1990 (supra); and *Pharmaceutical Dosage Forms and Drug Delivery Systems*, 6th ed., Williams & Wilkins (1995).

In order to enhance the percutaneous absorption of the active ingredients, one or more of a number of agents can be added in the topical formulations including, but not limited to, dimethylsulfoxide, dimethylacetamide, dimethylformamide, surfactants, azone, alcohol, acetone, propylene glycol and polyethylene glycol. In addition, physical methods can also be used to enhance transdermal penetration such as, e.g., by iontophoresis or sonophoresis. Alternatively, or in addition, liposomes may be employed.

A topically applied composition of the invention contains a pharmaceutically effective agent that lightens skin as described herein, and those ingredients as are necessary for use as a carrier, such as an emulsion, a cream, an ointment, an aqueous solution, a lotion or an aerosol. Non-limiting examples of such carriers are described in more detail below and may be found in International Patent Publication WO 00/62742, published Oct. 26, 2000; U.S. Pat. No. 5,691,380 to Mason et al., issued Nov. 25, 1997; U.S. Pat. No. 5,968,528 to Deckner et al., issued Oct. 19, 1999; U.S. Pat. No. 4,139,619 to Chidsey, III, issued Feb. 13, 1979; and U.S. Pat. No. 4,684,635 to Orentreich et al., issued Aug. 4, 1987; which are incorporated herein by reference. Suitable pharmaceutical carriers are further described in *Remington's Pharmaceutical Sciences,* 17th ed., Mack Publishing Company, Easton, Pa. (1990), which is a standard reference text in this field.

The pharmaceutical compositions of the invention may optionally include components suitable for application to keratinous tissue, that is, when incorporated into the composition, they are suitable for use in contact with human keratinous tissue without undue toxicity, incompatibility, instability, allergic response, and the like within the scope of sound medical judgment. In addition, such optional components are useful provided that they do not unacceptably alter the benefits of the active compounds of the invention. The *CTFA Cosmetic Ingredient Handbook*, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin and bisabolol and dipotassium glycyrrhizinate), skin treating agents, thickeners, and vitamins and derivatives thereof.

In addition to the pharmaceutically effective amount of an agent disclosed herein, the topical compositions of the present invention also comprise a dermatologically acceptable carrier. The phrase "dermatologically acceptable carrier", as used herein, means that the carrier is suitable for topical application to the skin, i.e., keratinous tissue, has good aesthetic properties, is compatible with the active agents of the present invention and any other components, and will not cause any safety or toxicity concerns. A safe and effective amount of carrier is from about 50% to about 99.99%, preferably from about 80% to about 99.9%, more preferably from about 90% to about 98%, and most preferably from about 90% to about 95% of the composition.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560 to Dickert et al., issued Aug. 28, 1973; U.S. Pat. No. 4,421,769 to Dixon, et al., issued Dec. 20, 1983; and McCutcheon's Detergents and Emulsifiers, North American Edition, pages 317–324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present-invention comprise from about 10% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of anagent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less than about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100 degrees Celsius. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g. mineral oil, vegetable oils, synthetic oils, semisynthetic oils, etc.

Useful topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Non-limiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase by weight of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner et al., issued Dec. 17, 1991; and U.S. Pat. No. 5,073,372, to Turner et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See McCutcheon's. *Detergents and Emulsifiers* (1986), supra; U.S. Pat. No. 5,011,681 to Ciotti et al., issued Apr. 30, 1991; U.S. Pat. No. 4,421,769 to Dixon et al. issued Dec. 20, 1983; and U.S. Pat. No. 3,755,560 to Dickert et al., issued Aug. 28, 1973. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued Sep. 29, 1992; U.S. Pat. No. 5,151,210 to Steuri et al. issued Sep. 29, 1992; U.S. Pat. No. 5,120,532 to Wells et al, issued Jun. 9, 1992; U.S. Pat. No. 4,387,090 to Bolich Jr., issued Jun. 7, 1983; U.S. Pat. No. 3,155,591 to Hilfer, issued Nov. 3, 1964; U.S. Pat. No. 3,929,678 to Laughlin et al, issued Dec. 30, 1975; U.S. Pat. No. 3,959,461 to Bailey et al., May 25, 1976; *McCutcheon's, Detergents & Emulsifiers* (North American edition 1979) M. C. Publishing Co.; and Schwartz, et al., *Surface Active Agents, Their Chemistry and Technology*, New York: Interscience Publishers, 1949.

Alternatively, other useful cationic emulsifiers include amino-amides. Non-limiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water-insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, *Cosmetics, Science and Technology*, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

Ointments of the present invention may comprise a simple carrier base of animal or vegetable oils or semi-solid hydrocarbons (oleaginous); absorption ointment bases, which absorb water to form emulsions; or water soluble carriers, e.g., a water soluble solution carrier. Ointments may further comprise a thickening agent, such as described in Sagarin, Cosmetics, Science and Technology, 2nd Edition, Vol. 1, pp. 72–73 (1972), incorporated herein by reference, and/or an emollient. For example, an ointment may comprise from about 2% to about 10% of an emollient; from about 0.1% to about 2% of a thickening agent; and a pharmaceutically effective amount of an agent described herein.

By way of non-limiting example, 1000 g of topical cream is prepared from the following types and amounts of ingredients: a pharmaceutically effective amount of an agent disclosed herein, tegacid regular (150 g) (a self-emulsifying glyceryl monostearate from Goldschmidt Chemical Corporation, New York, N.Y.), polysorbate 80 (50 g), spermaceti (100 g), propylene glycol (50 g), methylparaben (1 g), and deionized water in sufficient quantity to reach 1000 gm. The tegacid and spermaceti are melted together at a temperature of 70–80° C. The methylparaben is dissolved in about 500 g. of water and the propylene glycol, polysorbate 80, and active compound are added in turn, maintaining a temperature of 75–80° C. The methylparaben mixture is added slowly to the tegacid and spermaceti melt, with constant stirring. The addition is continued for at least 30 minutes with additional stirring until the temperature has dropped to 40–45° C. Finally, sufficient water is added to bring the final weight to 1000 g. and the preparation stirred to maintain homogeneity until cooled and congealed.

By way of non-limiting example, 1000 g of a topical ointment is prepared from the following types and amounts of ingredients: a pharmaceutically effective amount of an agent disclosed herein, zinc oxide (50 g), calamine (50 g), liquid petrolatum (heavy) (250 g), wool fat (200 g), and enough white petrolatum to reach 1000 g. Briefly, the white petrolatum and wool fat are melted and 100 g of liquid petrolatum added thereto. The pharmaceutically effective amount of an agent disclosed herein, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

By way of non-limiting example, 1000 g of an ointment containing a pharmaceutically effective amount of an agent disclosed herein is prepared from the following types and amounts of ingredients: a pharmaceutically effective amount of an agent disclosed herein, light liquid petrolatum (250 g), wool fat (200 g), and enough white petrolatum to reach 1000 g. Briefly, the pharmaceutically effective amount of an agent disclosed herein is finely divided and added to the light liquid petrolatum. The wool fat and white petrolatum are melted together, strained, and the temperature adjusted to 45–50° C. The liquid petrolatum slurry is added, and the ointment stirred until congealed.

By way of non-limiting example, 1000 ml of an aqueous solution containing a pharmaceutically effective amount of an agent disclosed herein is prepared from the following types and amounts of ingredients: a pharmaceutically effective amount of an agent disclosed herein, polyethylene glycol 4000 (120 g) myristyl-gamma-picolinium chloride (0.2 g), polyvinylpyrrolidone (1 g), and enough deionized water to reach 1000 milliliters. Briefly, the ingredients are dissolved in the water and the resulting solution is sterilized by filtration.

By way of non-limiting example, 1000 g of lotion containing a pharmaceutically effective amount of an agent disclosed herein is prepared from the following types and amounts of ingredients: a pharmaceutically effective amount of an agent disclosed herein, N-methylpyrrolidone (40 g), and enough propylene glycol to reach 1000 g.

By way of non-limiting example, an aerosol containing a pharmaceutically effective amount of an agent disclosed herein is prepared from the following types and amounts of materials: a pharmaceutically effective amount of an agent disclosed herein, absolute alcohol (4.37 g), dichlorodifluoroethane (1.43 g) and dichlorotetrafluoroethane (5.70 g). Briefly, the pharmaceutically effective amount of an agent disclosed herein is dissolved in the absolute alcohol and the resulting solution filtered to remove particles and lint. This solution is chilled to about minus 30° C. Then, to this is added the chilled mixture of dichlorodifluoromethane and dichlorotetrafluoroethane.

For oral administration, gelatin capsules or liquid-filled soft gelatin capsules can contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective, targeted disintegration in the gastrointestinal tract. Liquid dosage forms for oral administration can contain coloring and/or flavoring to increase patient acceptance.

In general, sterile water, oil, saline, aqueous dextrose (glucose), polysorbate and related sugar solutions and glycols such as propylene glycol or polyethylene glycols, are suitable carriers for parenteral solutions. Solutions or emulsions for parenteral administration preferably contain about 5–15% polysorbate 80 or lecithin, suitable stabilizing agents and, if necessary, buffer substances. Anti-oxidizing agents such as, but not limited to, sodium bisulfite, sodium sulfite, or ascorbic acid, either alone or combined, are suitable stabilizing agents. Also useful are citric acid and its salts, and sodium EDTA. In addition, parenteral solutions can contain preservatives including, but not limited to, benzalkonium chloride, methyl- or propyl-paraben, and chlorobutanol.

Additional examples of particular formulations comprising an active compound of the present invention are provided below.

An example of the preparation of a topical gel follows.

TABLE 1

Topical Gel:

| Ingredient | Percent by Weight |
|---|---|
| Active compound | 0.50 |
| Propylene glycol | 20.00 |
| Ethanol | 20.00 |
| Carboxyvinyl polymer [Carbomer 940 ™] | 1.00 |
| Hydroxyethyl cellulose | 0.40 |
| Benzyl alcohol | 1.00 |
| Sodium hydroxide 1N | to pH 6 |
| Distilled water | Balance |

The components other than sodium hydroxide are combined to yield a homogeneous dispersion. Addition of sodium hydroxide causes the mixture to gel yielding a ready-to-use semisolid.

An example of the preparation of a topical cream follows.

TABLE 2

Topical Cream:

| Ingredient | Percent by Weight |
|---|---|
| Active compound | 0.50 |
| Stearic acid | 7.00 |
| Stearyl alcohol | 5.00 |
| Cetyl alcohol | 2.00 |
| Glycerin | 10.00 |
| Sodium laurylsulfate | 1.00 |
| Propylparaben | 0.05 |

TABLE 2-continued

Topical Cream:

| Ingredient | Percent by Weight |
|---|---|
| Methylparaben | 0.25 |
| Disodium edetate | 0.05 |
| Distilled water | Balance |

The first four ingredients are heated to approximately 70° C. to produce a uniform melt. The remaining ingredients are combined, heated to approximately 75° C., and added with mixing to the previously prepared melt. The emulsion thus formed is subsequently homogenized and cooled to yield a smooth white cream.

An example of the preparation of a topical lotion follows.

TABLE 3

Topical Lotion:

| Ingredient | Percent by Weight |
|---|---|
| Active compound | 0.50 |
| Glyceryl monostearate | 1.00 |
| Isopropyl palmitate | 4.00 |
| Polyethylene glycol 400 distearate | 2.00 |
| Glycerin | 10.00 |
| Methylparaben | 0.10 |
| Sodium cetylsulfate | 5.00 |
| Distilled water | Balance |

The first four ingredients are combined and heated to approximately 70° C., then added with agitation to a mixture of the remaining ingredients, also at about 70° C. The emulsion is appropriately homogenized and cooled to produce a smooth, white, pourable lotion.

An example of the preparation of a topical solution follows.

TABLE 4

Topical Solution:

| Ingredient | Percent by Weight |
|---|---|
| Active compound | 0.50 |
| Propylene glycol | 20.00 |
| Ethanol | 50.00 |
| Benzyl alcohol | 1.00 |
| Disodium edetate | 0.01 |
| Propyl gallate | 0.10 |
| Citric acid | 0.20 |
| Sodium hydroxide 1N | to pH 6 |
| Distilled water | Balance |

All ingredients except sodium hydroxide are combined with agitation, and the pH of the resultant solution is adjusted with 1N sodium hydroxide, to pH 6, to yield a free-flowing, quick-drying topical solution.

The topical formulations presented herein are examples of typical gel, cream, lotion, or solution dosage forms of active compounds for use in lightening skin. Other optional components can be added or excipient ratios can be adjusted to enhance cosmetic acceptability of the formulations. Additionally, these alterations can be made to customize the composition toward a particular active compound, for example, to ensure solubilization or to enhance chemical or physical stability. Optional components would include viscosity adjusters such as celluloses, emollient oils such as mineral oil or glycerides, humectants such as polyols, cosolvents such as isopropyl alcohol or acetone, emulsifying agents of the anionic, cationic and non-ionic types, preservatives, antioxidants, opacifiers, colorants and perfumes.

An example of the preparation of an oral tablet formulation follows.

TABLE 5

Tablet Formulation:

| Ingredient | Amount (mg) |
|---|---|
| Active Compound | 25 |
| Lactose | 50 |
| Cornstarch (for mix) | 10 |
| Cornstarch (paste) | 10 |
| Magnesium stearate (1%) | 5 |
| Total | 100 |

The active compound, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet.

An example of the preparation of an oral solution follows.

TABLE 6

Oral Solution:

| Ingredient | Percent by Weight |
|---|---|
| Active Compound | 2.0 |
| Ethyl alcohol | 10.0 |
| Benzyl alcohol | 1.0 |
| Peppermint flavor | 0.2 |
| Vanillin | 0.2 |
| Polysorbate 40 | 0.1 |
| Sucrose | 50.0 |
| Purified water | Balance |

The ingredients are combined and mixed to form a uniform solution.

As will be understood by those in the art, the compositions and pharmaceutical compositions of the invention may be provided as part of a kit. Kits of the present invention comprise a container comprising one or more specific compounds and/or pharmaceutical compositions of the present invention that lighten skin. The container is designed to prevent contamination, minimize evaporation or drying of the composition, etc. Optionally, the kit further comprises printed instructions as a label or package insert directing the use of the enclosed compound or composition to lighten skin pigmentation. The compound or composition may or may not be provided in a preset unit dose or usage amount.

The ability of compounds of formula I to inhibit tyrosinase may be determined using any of the following procedures.

1. Tyrosinase (DOPA Oxidase) Assay Using Cell Lysate:

Human melanoma cell line, SKMEL 188 (licensed from Memorial Sloan-Kettering), is used in the cell lysate assay and the screen. In the assay, compounds and L-dihydroxyphenylalanine (L-DOPA) (100 $\mu$g/ml) are incubated with the cell lysates containing human tyrosinase for 8 hrs before the plates are read at 405 nm. Most of the compounds of formula I that were tested in this assay exhibited an $IC_{50}$ of 10 $\mu$M or less. For example, the compound of Example 22 below, i.e., trans-4-(2,4-Dihydroxyphenyl)cyclohexyl (2R)-2-amino-3-phenylpropanoate, had an $IC_{50}$ in this assay of about 2 μm.

2. Melanin Assay in Human Primary Melanocytes:

Compounds are incubated with human primary melanocytes in the presence of α-melanocyte stimulating hormone (α-MSH) for 2–3 days. Cells are then lysed with sodium hydroxide and sodium dodecyl sulfate (SDS) and melanin signals are read at 405 nm. Alternatively, $^{14}$C-DOPA is added to the cells in combination with tyrosinase inhibitors and acid-insoluble $^{14}$C-melanin is quantitated by a scintillation counter. $IC_{50}$'s reflect the inhibitory potency of the compounds in the new melanin synthesis that was stimulated by α-MSH.

3. Tyrosine Kinase Assay (TK):

TK assays can be performed using purified tyrosine kinase domains of c-met, erb-B2, or IGF-r. A specific antibody against phosphorylated tyrosine residue is used in the assay. Colorimetric signals are generated by horseradish peroxidase, which is conjugated to the antibody.

4. Human Skin Equivalent Model:

A mixture of human melanocytes and keratinocytes is grown in an air-liquid interphase. This tissue culture forms a three-dimensional structure that histologically and microscopically resembles the human skin epidermis. Test compounds are added on top of the cells to mimic topical drug application. After incubation with the compounds (10 μM) for 3 days, the cells are washed extensively and lysed for DOPA oxidase assay.

5. IL-1 Assay (Interleukin-1 Assay):

An IL-1α ELISA assay (R&D system) can be used to evaluate the effect of compounds on IL-1 secretion in a human skin equivalent model. IL-1α is a pro-inflammatory cytokine and plays a role in UV-induced skin inflammation.

6. In Vivo Study:

Black or dark brown guinea pigs with homogeneous skin color can be used in this study. A solution of the test compound of formula I (5% in ethanol:propylene glycol, 70:30) and the vehicle control are applied to the animals twice daily, 5 days per week for 4–8 weeks. Using this assay, depigmentation can be determined by subtracting the light reflectance of untreated skin from the light reflectance of treated skin.

The present invention is illustrated by the following examples. It will be understood, however, that the invention is not limited to the specific details of these examples. Melting points are uncorrected. Proton nuclear magnetic resonance spectra (400 MHz $^1$H NMR) were measured for solutions in $d_6$-DMSO, $CDCl_3$, or $d_4$-MeOH, and peak positions are expressed in parts per million (ppm) downfield from tetramethylsilane (TMS). The peak shapes are denoted as follows: s, singlet; d, doublet; t, triplet; q, quartet, m, multiplet, b, broad.

Flash column chromatography (FCC) was carried out on $SiO_2$. RP-HPLC refers to preparative reverse-phase high-performance liquid chromatography. Mass spectra were obtained using an electrospray ionisation. LCMS analysis was performed using a Waters 2700 autosampler, attached to a Waters 2690 HPLC, using the conditions described below. Mass spectra were obtained on a Micromass Platform LC mass spectrometer, using positive and negative electrospray ionisation. Samples were dissolved in DMSO.

| | |
|---|---|
| Column: | Waters Symmetry C18, 3.5 μm, 2.1 × 30 mm |
| Mobile Phase A: | 95% Water, 5% Acetonitrile, 0.1% Formic acid |
| Mobile Phase B: | Acetonitrile, 0.1% Formic acid |
| Gradient: | 0.0 min 0% B |
| | 0.2 min 0% B |
| | 3.0 min 90% B |
| | 3.5 min 90% B |
| | 3.6 min 0% B |
| | 4.5 min 0% B |
| Flow: | 1.0 ml/min |
| Injection: | 10 μl |
| DAD: | 210–230 nm |

The following examples are illustrative only, and are not intended to limit the scope of the present invention.

EXAMPLES

Preparation 1

3-Benzyloxy-2-cyclohexen-1-one

To a round bottomed flask equipped with Dean-Stark apparatus was added 1,3-cyclohexanedione (60.0 g), toluene (450 ml), p-toluenesulfonic acid monohydrate (1.35 g) and benzyl alcohol (52.6 g, 487). The resulting solution was heated to reflux temperature for 12 hr. The reaction mixture was cooled to room temperature and then washed with saturated aqueous sodium carbonate solution (2×100 ml). The organic layer was then washed with brine (100 ml), dried over magnesium sulfate, filtered and concentrated in vacuo, affording a brown oil (94.9 g) which crystallised upon standing for 17 hr. The crude crystalline material was slurried in isopropyl ether (20 ml). The mixture was filtered and the crystalline material was washed with ice cold isopropyl ether (3×30 ml), then with cold petroleum ether (2×20 ml). The resulting peach-colored crystalline solid was dried overnight under reduced pressure, furnishing the title compound (74.4 g, 76%). m/z ($ES^+$) 203 ($M+H^+$).

Preparation 2

(±)-3-Benzyloxy-6-(8-hydroxy-1,4-dioxaspiro[4.5]dec-8-yl)-2-cyclohexen-1-one

To a round-bottomed flask was added anhydrous tetrahydrofuran (600 ml) and diisopropylamine (38.1 ml). The stirred solution was cooled to −78° C. and nbutyl lithium (113.4 ml, 2.4 M in cyclohexanes) was added dropwise via syringe in 20 ml portions. The resulting yellow solution was stirred for 35 min at −78° C., then 3-benzyloxy-2-cyclohexen-1-one (50.0 g) was added as a solution in anhydrous tetrahydrofuran (100 ml). The solution was stirred for 1 hr prior to the addition of cyclohexane-1,4-dione monoethylene ketal (38.7 g) as a solution in anhydrous tetrahydrofuran (100 ml). The solution was stirred for 2 hr at −78° C., then allowed to warm slowly to room temperature over 1 hr. Saturated aqueous ammonium chloride (80 ml) was added, followed by dichloromethane (700 ml), and the mixture was stirred until no solids remained. The layers were separated and the aqueous phase extracted with dichloromethane (2×100 ml). The combined organic layers were washed with brine (50 ml), dried over magnesium sulfate, then concentrated in vacuo. Trituration of the resulting solid with methanol afforded the title compound (78.4 g, 88%). m/z ($ES^+$) 359 ($M+H^+$).

Preparation 3

(±)-1-Benzyloxy-6-bromo-3-(1.4-dioxaspiro[4,5]dec-8-yl)-2-oxabicyclo[2.2.2]octan-5-one A round bottomed flask was charged with (±)-3-benzyloxy-6-(8-hydroxy-1,4-dioxaspiro[4.5]de-8cyl)-2- cyclohexen-1-one (78.4 g) and dichloromethane (600 ml). To the stirred solution was added N-bromosuccinimide (40.9 g) in one portion, followed by aqueous hydrobromic acid (3 drops, 48% solution) when no more solid remained. The resulting solution was stirred at room temperature for 2 hr then poured into a separating funnel containing aqueous sodium metabisulfite solution (150 ml) and dichloromethane (200 ml), then the funnel was shaken vigorously. The layers were separated and the organic layer was washed with brine (200 ml), dried over magnesium sulfate, filtered, then concentrated in vacuo to give a solid. Trituration with methanol (500 ml) afforded the title compound (82.8 g, 86%) as a white solid. m/z (ES$^+$) 437 and 439 [(1:1), M+H$^+$].

Preparation 4

5-Benzyloxy-2-(1,4-dioxaspiro[4.5]dec-7-en-8-yl)phenol

A round bottomed flask was charged with (±)-1-benzyloxy-6-bromo-3-(1,4-dioxaspiro[4.5]de-8-cyl)2-oxabicyclo[2.2.2]octan-5-one (13.8 g) and anhydrous N,N-dimethylformamide (140 ml). To the stirred solution was added 1,8-diazabicyclo[5.4.0]undec-7-ene (9.92 ml) in one portion. The solution turned dark brown in colour immediately and was then heated to 140° C. for 12 hr with vigorous stirring. The reaction mixture was allowed to cool to room temperature and most of the solvent was removed under reduced pressure. The remaining oil was partitioned between ethyl acetate (200 ml) and water (100 ml), then the layers were separated and the aqueous phase was extracted with ethyl acetate (3×50 ml). The combined organic layers were back-extracted with water (3×30 ml) to remove any residual N,N-dimethylformamide. The organic phase was washed with brine (20 ml), dried over magnesium sulfate, filtered and concentrated in vacuo to afford a brown oily solid, which was adsorbed onto silica gel. Purification via flash column chromatography (SiO$_2$, ethyl acetate/petroleum ether, 1:1, v/v) furnished the title compound (7.1 g, 66%) as a white solid. m/z (ES$^+$) 339 (M+H$^+$).

Preparation 5

4-(2,4-Dihydroxyphenyl)cyclohexanone

A round bottomed flask was charged with 4-(1,4-dioxaspiro[4.5]decyl)-1,3-benzenediol (11.3 g), acetone (250 ml) and water (50 ml). To the stirred solution was added pyridinium p-toluenesulfonate (1.14 g) in one portion and the reaction mixture was then heated to reflux, temperature for 8 hr. After allowing the reaction mixture to cool to room temperature, most of the acetone was removed in vacuo and the remaining mixture was partitioned between ethyl acetate (200 ml) and water (50 ml). The aqueous layer was extracted with ethyl acetate (3×50 ml) and the combined organic layers were washed with brine (30 ml), dried over magnesium sulfate, filtered and concentrated under reduced pressure to afford an off white powder. After washing the powder with dichloromethane (100 ml) and removing excess solvent under reduced pressure, the title compound (9.30 g, 100%) was obtained as an off-white powder. m/z (ES$^+$) 207 (M+H$^+$).

Preparation 6

4-(2,4-Bis{[tert-butyl(dimethyl)silyl]oxy}phenyl)cyclohexanone 4-(2,4-Dihydroxyphenyl)cyclohexanone (400 mg) was dissolved in dimethyl formamide (3 ml) with stirring. tert-Butyldimethylsilyl chloride (704 mg), imidazole (660 mg) and 4-dimethylaminopyridine (3 mg) were added sequentially. After 4 hr, the solvent was removed in vacuo and the residue partitioned between ethyl acetate (20 ml) and water (5 ml). The aqueous phase was extracted with ethyl acetate (2×10 ml), and the combined organic phases were washed with brine (10 ml), dried over anhydrous magnesium sulfate, and concentrated under reduced pressure to give a brown oil. Purification via flash column chromatography (SiO$_2$ eluting with ethyl acetate/petroleum ether, 1:9 v/v) furnished the title compound as white flakes (750 mg, 89%). m/z (ES$^+$) 435 (M+1)$^+$.

Preparation 7 cis-N-Benzyl-N-[4-(2,4-bis{[tert-butyl(dimethyl)silyl]oxy}phenyl)cyclohexyl]amine To a round bottomed flask was charged 4-(2,4-bis{[tert-butyl(dimethyl)silyl]oxy}phenyl) cyclohexanone (3.20 g), 1,2-dichloroethane (85 ml), and to the stirred solution was added benzylamine (0.97 ml) as a solution in 1,2-dichloroethane (20 ml) followed by activated powdered 4 Å molecular sieves (5.80 g) and the reaction mixture stirred for 2.5 hr. Tetramethylammoniumtriacetoxyborohydride (2.90 g) was added in one portion and the reaction mixture stirred for 64 hr at room temperature. Aqueous sodium hydroxide solution (30 ml, 0.4M) was added and vigorous stirring was continued for 0.5 hr. The reaction mixture was filtered through celite, washing with dichloromethane (100 ml). The layers were separated and the aqueous layer was extracted with dichloromethane (2×50 ml). The combined organic phases were washed with brine (100 ml), dried over magnesium sulfate, filtered and concentrated in vacuo affording the-crude product. Purification via flash column chromatography (SiO$_2$, ethyl acetate/petroleum ether, gradient elution using 1:9, 1:4, then 3:7 v/v) furnished the title compound (2.69 g, 70%) as a pale yellow oil. $\delta_H$(CDCl$_3$) 0.01 (6H, s), 0.05 (6H, s), 0.77 (9H, s), 0.83 (9H, s), 1.31 (1H, br), 1.39 (4H, m), 1.52 (2H, m), 1.70 (2H, m), 2.69 (1H, m), 2.75 (1H, m), 6.10 (1H, d), 6.23 (1H, dd), 6.84 (1H, d), 7.15 (5H, m).

Preparation 8

N-Benzyl-N-[4-(2,4-bis{[tert-butyl(dimethyl)silyl]oxy}phenyl)cyclohexylidene]amine To a round bottomed flask was added 4-(2,4-bis{[tert-butyl(dimethyl)silyl]oxy}phenyl) cyclohexanone (817 mg). Dichloromethane (50 ml) was added followed by benzylamine (0.82 ml, 7.52 mmol) and activated 4 Å molecular sieves (10.0 g). The reaction mixture was stirred vigorously for 15 hr, then dichloromethane (50 ml) was added and the reaction mixture filtered through celite, washing with dichloromethane (50 ml). The filtrate was concentrated in vacuo affording the title compound (1.00 g, 86%) as a yellow oil. $\delta_H$(CDCl$_3$) 0.19 (6H, s), 0.26 (6H, s), 0.98 (9H, s), 1.03 (9H, s), 1.51 (1H, m), 1.72 (1H, m), 2.03 (2H, m), 2.45 (1H, m), 2.60 (1H, m), 3.04 (1H, m), 3.22 (1H, m), 4.55 (1H, d), 4.60 (1H, d), 6.31 (1H, d), 6.41 (1H, dd), 6.93 (1H, d), 7.33 (5H, m).

Preparation 9 trans-N-Benzyl-N-[4(2,4-bis{[tert-butyl(dimethyl)silyl]oxy}phenyl) cyclohexyl]amine To a round bottomed flask was added N-benzyl-N-[4-(2,4-bis{[tert-butyl (dimethyl)silyl]oxy}phenyl)

cyclohexylidene]amine (4.00 g) and tetrahydrofuran (480 ml) followed by methanol (120 ml). To the solution was added sodium borohydride (1.16 g) and the reaction mixture stirred for 17 hr. The reaction mixture was then diluted with diethyl ether (600 ml) and aqueous sodium hydroxide (400 ml, 0.4M) added. After stirring for 10 min, the layers were separated and the aqueous layer extracted with dichloromethane (3×100 ml). The combined organic phases were washed with brine (50 ml), dried over magnesium sulfate and concentrated in vacuo to give a yellow oil. Purification via flash column chromatography (SiO$_2$, ethyl acetate/petroleum ether, gradient elution using 1:9, 1:4, then 3:7, v/v) furnished the title compound (2.09 g, 54%) as a cream solid. $\delta_H$(CDCl$_3$) 0.01 (6H, s), 0.05 (6H, s), 0.80 (9H, s), 0.85 (9H, s), 1.18 (4H, m), 1.66 (2H, m), 1.87 (2H, m), 2.19 (1H, m), 2.68 (1H, M), 6.12 (1H, d), 6.23 (1H, dd), 6.77 (1H, d), 7.17 (5H, m).

Preparation 10 trans-4-(2,4-Bis{[tert-butyl(dimethyl)silyl]oxy}phenyl)cyclohexylamine

To a round bottom flask was added trans-N-benzyl-N-[4-(2,4-bis{[tert-butyl(dimethyl)silyl]oxy}phenyl) cyclohexyl] amine (500 mg, 0.95 mmol) and ethanol (20 ml). To the stirred solution was added palladium (10% w/w on activated carbon, 200 mg, 0.19 mmol) as a slurry in ethanol (5 ml). The reaction vessel was evacuated, then placed under hydrogen (10 cycles). The reaction mixture was stirred vigorously under an atmosphere of hydrogen for 18 hr, then filtered through a celite plug, washing with methanol (100 ml). The solvent was removed in vacuo affording the title compound (402 mg, 97%) as a colourless oil. $\delta_H$(CDCl$_3$) 0.01 (6H, s), 0.05 (6H, s), 0.78 (9H, s), 0.82 (9H, s), 1.08 (2H, m), 1.21 (2H, m), 1.62 (2H, m), 1.78 (2H, m), 2.59 (1H, m), 6.11 (1H, d), 6.22 (1H, dd), 6.78 (1H, d).

Preparation 11 cis-4-(2,4-bis{[tert-butyl(dimethyl)silyl]oxy}phenyl)cyclohexylamine

To a round bottom flask equipped with magnetic stirrer was added cis-N-benzyl-N-[4-(2,4-bis{[tert-butyl(dimethyl)silyl]oxy}phenyl)cyclohexyl]amine (700 mg) and ethanol (30 ml). To the stirred solution was added palladium (10% w/w on activated carbon, 283 mg) as a slurry in ethanol (5 ml). The reaction vessel was evacuated then placed under hydrogen (10 cycles). The reaction mixture was stirred vigorously under an atmosphere of hydrogen for 18 hr then filtered through a celite plug, washing with methanol (100 ml). The solvent was removed in vacuo affording the title compound (561 mg, 97%) as a colourless oil. $\delta_H$(CDCl$_3$) 0.01 (6H, s), 0.04 (6H, s), 0.78 (9H, s), 0.83 (9H, s), 1.21–1.55 (10H, m), 2.64 (1H, m), 3.05 (1H, m), 6.11 (1H, d), 6.22 (1H, dd), 6.84 (1H, d).

Preparation 12

1-Bromo-2,4-bis(methoxymethoxy)benzene

A round bottomed flask was loaded with 4-bromoresorcinol (9.45 g) and CH$_2$Cl$_2$ (50 ml). The stirred suspension was cooled to 0° C. and diisopropylamine (19.1 ml) was added in one portion. Stirring of the solution was continued for a further 10 min before methyl chloromethyl ether (10.7 ml) was added. The resulting yellow solution was then allowed to warm to room temperature overnight. Ammonium hydroxide solution (50 mL, 50%) was poured into the reaction vessel and stirring was continued for 1 hr. The mixture was poured into a separating funnel and the phases separated. The aqueous phase was then extracted with CH$_2$Cl$_2$ (3×30 ml) and the combined organics washed with brine (20 ml), dried over anhydrous magnesium sulfate, filtered and concentrated in vacuo affording an orange oil. Purification was achieved by flash column chromatography, (SiO$_2$, ethyl acetate/petroleum ether, 1:1, v/v), furnishing the title product (10.7 g, 77%) as a pale yellow oil. $\delta_H$(CDCl$_3$) 7.42 (1H, d), 6.88 (1H, d), 6.64 (1H, dd), 5.24 (2H, s), 5.15 (2H, s), 3.53 (3H, s), 3.48 (3H, s).

Preparation 13

8-[2,4-Bis(methoxymethoxy)phenyl]-1,4-dioxaspiro[4.5]decan-8-ol

A round bottomed flask was loaded with 1-bromo-2,4-bis(methoxymethoxy)benzene (2.00 g) and THF (50 mL). N,N,N',N'-Tetramethylethylene diamine (2.3 ml) was added and the solution was cooled to −78° C. n-Butyl lithium (9.5 ml, 1.6M in hexane) was added. The resulting solution was stirred for 1 hr at −78° C. and 1,4-cyclohexanedione mono-ethylene ketal (1.35 g) was added as a solution in THF (25 ml). The resulting solution was stirred at −78° C. for 1 hr and then allowed to warm to room temperature overnight. Hydrochloric acid (20 ml, 2M) was added and the reaction mixture stirred vigorously for 15 min. Ethyl acetate (100 ml) was added and the mixture poured into a separating funnel. The phases were separated and the aqueous phase was extracted with ethyl acetate (3×20 ml). The combined organic phases were washed with brine (20 ml), dried over anhydrous magnesium sulfate, filtered and concentrated affording an orange oil, which was purified by flash column chromatography (SiO$_2$, ethyl acetate/petroleum ether, 45:55, v/v). The title product (1.42 g, 56%) was isolated as a colourless oil. m/z (ES$^+$) 337 (M−H$_2$O+H$^+$); $\delta_H$ (CDCl$_3$) 1.61–1.64(2H, m), 2.00–2.18(6H, m), 3.44(3H, s), 3.48(3H, s), 3.90–3.97(4H, m), 5.11(2H, s), 5.24(2H, s), 6.64(1H, dd), 6.82(1H, d), 7.20(1H, d).

Preparation 14

8-[2,4-Bis(methoxymethoxy)phenyl]-1,4-dioxaspiro[4.5]dec-7-ene

8-[2,4-Bis(methoxymethoxy)phenyl]-1,4-dioxaspiro[4.5]decan-8-ol (1.40 g) was placed in a round bottomed flask fitted with Dean-Stark apparatus. Toluene (30 ml) was added, followed by camphor sulphonic acid (10 mg). The stirred solution was then heated under reflux for 1 hr, cooled, and saturated aqueous sodium bicarbonate solution (10 ml) added. The mixture was poured into a separating funnel and the phases separated. The aqueous phase was extracted with ethyl acetate (2×15 ml) and the combined organics were washed with brine (15 ml), dried over anhydrous magnesium sulphate, filtered and then concentrated in vacuo yielding an orange oil, which was purified by flash column chromatography (SiO$_2$, ethyl acetate/petroleum ether, 45:55, v/v) to afford the title product (0.94 g) as a colourless oil. $\delta_H$ (CDCl$_3$) 1.84 (2H, t), 2.41–2.43 (2H, m), 2.56–2.62 (2H, m), 3.47 (6H, s), 3.98–4.02 (4H, m), 5.13 (4H, s), 5.58–5.63 (1H, m), 6.64 (1H, dd), 6.78 (1H, d), 7.08 (1H, d).

Preparation 15

8-[2,4-Bis(methoxymethoxy)phenyl]-1,4-dioxaspiro[4.5]decane

8-[2,4-Bis(methoxymethoxy)phenyl]-1,4-dioxaspiro[4.5] dec-7-ene (0.950 g) and palladium (200 mg, 10% on carbon)

were stirred under an atmosphere of hydrogen for 15 hr. The mixture was then filtered through a plug of Celite, washing with ethyl acetate. The filtrate was then evaporated to dryness, affording the desired product (0.955 g, 100%) as a colourless oil. $\delta_H$ (CDCl$_3$) 1.67–1.87 (8H, m), 2.90–2.99 (1H, m), 3.46 (3H, s), 3.48 (3H, s), 3.97 (4H, s), 5.12 (2H, s), 5.18 (2H, s), 6.65 (1H, dd), 6.78 (1H, d), 7.12 (1H, d).

Preparation 16

4-[2,4-Bis(methoxymethoxy)phenyl]cyclohexanone

A round bottomed flask was charged with 8-[2,4-bis(methoxymethoxy)phenyl]-1,4-dioxaspiro[4.5]decane (3.20 g) and methanol (50 ml). Over a 20 min period, aqueous hydrochloric acid (50 ml, 1 M) was added to the stirred solution, at room temperature and the reaction mixture stirred for 1.5 hr. Solid sodium bicarbonate was added until the reaction mixture was neutralised and the solvent was removed under reduced pressure. The residue was partitioned between ethyl acetate (30 ml) and water (10 ml), and the aqueous layer was extracted with ethyl acetate (3×20 ml). The combined organic layers were washed with brine (10 ml), dried over magnesium sulfate, filtered and concentrated in vacuo. The crude product was purified via flash column chromatography (SiO$_2$, ethyl acetate/petroleum ether, 1:4, v/v), affording the title compound (2.20 g, 60%) as a white powder. $\delta_H$(CDCl$_3$) 1.85–1.96 (2H, m), 2.14–2.22 (2H, m), 2.46–2.59 (4H, m), 3.39 (1H, tt), 3.49 (3H, s), 3.52 (3H, s), 5.16 (2H, s), 5.23 (2H, s), 6.67–6.71 (1H, m), 6.85 (1H, m), 7.08 (1H, d).

Preparation 17

(±)-{4-[2,4-Bis(methoxymethoxy)phenyl]cyclohexylidene}Acetic Acid

To a round bottomed flask was added trimethylsilyldiethylphosphonoacetate (1.08 ml) and tetrahydrofuran (25 ml). The solution was cooled to 0° C. and n-butyl lithium (1.80 ml, 2.2M in cyclohexanes) was added dropwise and the reaction mixture allowed to warm to room temperature and stirred for 17 hr. 4-[(2,4-Bis(methoxymethoxy)phenyl)]cyclohexanone (750 mg) was added as a solution in tetrahydrofuran (25 ml). After 2 hr at room temperature, the mixture was poured into a separating funnel containing aqueous sodium hydroxide solution (10 ml, 10% w/v). After extracting with diethyl ether (10 ml), the aqueous layer was acidified by adding concentrated hydrochloric acid (10 ml), and extracted with diethyl ether (3×20 ml). The combined organic layers were washed with water (10 ml), dried over magnesium sulfate, filtered and concentrated in vacuo affording the title compound (422 mg, 52%) as an oil. $\delta_H$(CDCl$_3$) 1.86 (2H, m), 2.00–2.13 (4H, m), 2.42 (2H, m), 3.19 (1H, m), 3.48 (3H, s), 3.51 (3H, s), 5.14 (2H, s), 5.21 (2H, s), 5.71 (1H, s), 6.67 (1H, dd), 6.81 (1H, d), 7.05 (1H, d).

Preparation 18

(±)-{4-[2,4-Bis(methoxymethoxy)phenyl]cyclohexylidene}acetonitrile

To a round bottomed flask was added sodium hydride (40 mg, 60% dispersion in mineral oil) and 1,2-dimethoxyethane (10 ml). Diethyl cyanomethylphosphonate (102 μl, 0.95 mmol) was added and the reaction mixture allowed to warm to room temperature. 4-[(2,4-Bis(methoxymethoxy)phenyl)]cyclohexanone (200 mg) was added as a solution in 1,2-dimethoxyethane (10 ml) and the reaction mixture stirred for 17 hr at room temperature. The reaction mixture was poured into a separating funnel containing water (50 ml) and diethyl ether (50 ml). The layers were separated and the aqueous phase extracted with diethyl ether (2×20 ml). The combined organic layers were washed with brine (20 ml), dried over magnesium sulfate, filtered and concentrated in vacuo, to give an oil. Purification via flash column chromatography (SiO$_2$-ethyl acetate/petroleum ether, 1:2, v/v) afforded the title compound (141 mg, 66%) as a pale yellow oil. $\delta_H$(CD$_3$OD) 1.57–1.70 (2H, m), 2.02–2.25 (2H, m), 2.34–2.49 (2H, m), 2.60 (1H, m), 3.03 (1H, m), 3.24 (1H, m), 3.47 (3H, s), 3.52 (3H, s), 5.17 (2H, s), 5.23(2H, s), 5.33 (1H, s), 6.68 (1H, dd), 6.83 (1H, d), 7.09 (1H, d).

Preparations 19 and 20 trans-4-(2,4-Bis{[tert-butyl(dimethyl)silyl]oxy}phenyl)cyclohexanol;

cis-4-(2,4-Bis{[tert-butyl(dimethyl)silyl]oxy}phenyl)cyclohexanol

Sodium borohydride (164 mg) was added to a stirred solution of 4-(2,4-bis{[tert-butyl(dimethyl)silyl]oxy}phenyl)cyclohexanone (1.57 g) in ethanol (50 ml) at 0° C. After 18 hr at room temperature, the mixture was partitioned between 2M HCl (20 ml), water (40 ml) and ethyl acetate (50 ml) and the aqueous layer was re-extracted with ethyl acetate (2×50 ml). The combined organic extracts were washed with brine (40 ml), dried over magnesium sulfate and evaporated in vacuo. The residue was purified using flash column chromatography (SiO$_2$, ethyl acetate/petrol, 3:17 v/v) to give the trans-title compound as a white solid (546 mg, 35%), and the cis-title compound as a white solid (83 mg, 5%).

trans—$\delta_H$ (CDCl$_3$) 0.18 (6H, s), 0.22 (6H, s), 0.98 (9H, s), 1.02 (9H, s), 1.18–1.22 (4H, m), 1.80–1.84 (3H, m), 2.00–2.05 (2H, m), 2.78–2.86 (1H, m), 3.60–3.70 (1H, m), 6.28 (1H, d), 6.39 (1H, dd), 6.94 (1H, d).

cis—oil. $\delta_H$ (CDCl$_3$) 0.18 (6H, s), 0.22 (6H, s), 0.98 (9H, s), 1.02 (9H, s), 1.58–1.78 (6H, m), 1.84–1.92 (2H, m), 2.70–2.80 (1H, m), 4.12 (1H, bs), 6.28 (1H, d), 6.40 (1H, dd), 7.02 (1H, d).

Preparations 21 and 22 cis-O-Benzoyl-N-[4–2,4 bis{[tert-butyl(dimethyl)silyl]oxy}phenyl)cyclohexyl]hydroxylamine;

cis-N-[2,4-bis{[tert-butyl(dimethyl)silyl]oxy}phenyl)cyclohexyl]benzamide

A round bottomed flask was charged with cis-4-(2,4-bis{[tert-butyl(dimethyl)silyl]oxy}phenyl)cyclohexylamine (1.0 g), dichloromethane (15 ml) and buffer (pH 10.5, 0.05M NaHCO$_3$/0.1 NaOH) (20 ml). Dibenzoyl peroxide (1.19 g) in dichloromethane (5 ml) was added dropwise and the resulting mixture stirred for 17 hr. The mixture was diluted with dichloromethane (20 ml) and the organic layer separated, washed with brine (10 ml), dried over magnesium sulfate, filtered and concentrated in vacuo. Purification via flash chromatography (SiO$_2$, ethyl acetate/petroleum ether, 1:7, v/v) afforded preparation 19 (1.26 g, 53%) as a colourless solid. $\delta_H$ (CDCl$_3$) 0.21 (6H, s), 0.24 (6H, s), 1.10 (9H, s), 1.13 (9H, s), 1.62–1.90 (8H, m), 2.98 (1H, m), 3.48 (1H, m), 6.35 (1H, d), 6.43 (1H, dd), 7.10 (1H, d), 7.48 (2H, m), 7.60 (1H, m), 8.02 (1H, d) and 8.05 (1H, d). Further elution (ethyl acetate/petroleum ether, 1:2, v/v) afforded preparation 20 (0.47 g, 35%) as a colourless solid. $\delta_H$ (CDCl$_3$) 0.21 (6H, s), 0.26 (6H, s), 1.09 (9H, s), 1.13 (9H, s), 1.45–1.60 (2H, m), 1.73–1.88 (4H, m), 2.00–2.11 (2H, m), 2.98 (11H, m), 4.40 (1H, m), 6.32 (1H, d), 6.37 (1H, d), 6.44 (1H, dd), 7.00 (1H, d), 7.43–7.55 (4H, m) and 7.80 (1H, d).

Preparation 23 cis-O-Benzoyl-N-benzyl-N-[4–2,4-bis{[tert-butyl (dimethyl)silyl]oxy}phenyl)cyclohexyl] hydroxylamine A round bottomed flask was charged with cis-N-Benzyl-N-[42,4-bis{[tert-butyl(dimethyl)silyl]oxy}phenyl) cyclohexyl]amine (0.115 g), dichloromethane (2 ml) and buffer (pH 10.5, 0.05M NaHCO$_3$/0.1 NaOH) (3 ml). Dibenzoyl peroxide (0.106 g) in dichloromethane (1 ml) was added dropwise and the resulting mixture stirred rapidly for 17 hr. The mixture was diluted with dichloromethane (10 ml) and the organic layer separated, washed with brine (5 ml), dried over magnesium sulfate, filtered and concentrated in vacuo. Purification via flash chromatography (SiO$_2$, ethyl acetate/petroleum ether, 1:7, v/v) afforded the title compound (0.083 g, 59%) as a gum. $\delta_H$ (CDCl$_3$) 0.21 (6H, s), 0.24 (6H, s), 1.00 (9H, s), 1.04 (9H, s), 1.50–1.78 (4H, m), 2.00–2.12 (4H, m), 3.00 (1H, m), 3.20 (1H, m), 4.29 (2H, s), 6.28 (1H, d), 6.44 (1H, dd), 7.20–7.57 (9H, m) and 7.95 (2H, d).

Preparation 24 trans-O-Benzoyl-benzyl-N-[4–2,4-bis{[tert-butyl (dimethyl) silyl]oxy}phenyl)cyclohexyl] hydroxylamine A round bottomed flask equipped was charged with trans-Nbenzyl-N-[4-(2,4-bis{[tert-butyl(dimethyl)silyl] oxy}phenyl)cyclohexyl]amine (0.25 g), dichloromethane (4 ml) and buffer (pH 10.5) (6 ml). Dibenzoyl peroxide (0.23 g) in dichloromethane (2 ml) was added and the resulting mixture stirred for 72 hr. The mixture was diluted with dichloromethane (15 ml) and the organic layer separated, washed with brine (5 ml), dried over magnesium sulfate, filtered and concentrated in vacuo. Purification via flash chromatography (SiO$_2$, ethyl acetate/petroleum ether, 1:7, v/v) afforded the title compound (0.166 g, 54%) as a colourless gum. $\delta_H$ (CDCl$_3$) 0.12 (6H, s), 0.19 (6H, s), 1.00 (9H, s), 1.04 (9H, s), 1.18–1.36 (2H, m), 1.50–1.65 (2H, m), 1.85 (2H, m), 2.10 (2H, m), 2.68 (1H, m), 2.94 (1H, m), 4.19 (2H, s), 6.21 (1H, d), 6.32 (1H, dd), 6.97 (1H, d), 7.12–7.24 (3H, m) 7.29–7.37 (4H, m), 7.45 (1H, m) and 7.83 (2H, m).

Preparation 25 trans-O-Benzoyl-N[4–2,4-bis{[tert-butyl(dimethyl) silyl]oxy}phenyl)cyclohexyl]hydroxylamine A round bottomed flask was charged with trans(2,4-bis{[tert-butyl(dimethyl)silyl]oxy}phenyl)cyclohexylamine (0.156 g), dichloromethane (2 ml) and buffer (pH 10.5, 0.05M NaHCO$_3$/0.1 NaOH) (3 ml). Dibenzoyl peroxide (0.186 g) in dichloromethane (1 ml),was added and the resulting mixture-stirred for 4 hr. The mixture was diluted with dichloromethane (10 ml) and the organic layer separated, washed with brine (5 ml), dried over magnesium sulfate, filtered and concentrated in vacuo. Purification via flash chromatography (SiO$_2$, ethyl acetate/petroleum ether, 1:7, v/v) afforded the title compound (0.116 g, 54%) as a colourless oil. $\delta_H$ (CDCl$_3$) 0.21 (6H, s), 0.24 (6H, s), 0.98 (9H, s), 1.03 (9H, s), 1.27–1.40 (4H, m), 1.86 (2H, m), 2.08 (2H, m), 2.79 (1H, m), 3.08 (1H, m), 6.18 (1H, d), 6.32 (1H, dd), 6.86 (1H, d) and 7.33–7.88 (5H, m).

Preparation 26 syn-8-(2,4-bis{[tert-Butyl(dimethylsilyl)] oxy}phenyl)-1-oxaspiro[4.5]decan-2-one A round bottomed flask was charged with 4-(2,4-Bis{ [tert-butyl(dimethyl) silyl]oxy}phenyl)cyclohexanone (0.15 g, 0.34 mmol), ethyl acrylate (0.05 ml), methanol (2 ml) and THF (4 ml) and samarium diiodide in THF (0.1 M, 25 ml) added. After stirring for 17 hr, the reaction mixture was concentrated to approximately 25% of the original volume in vacuo. The mixture was diluted with a mixture of water (10 ml) and saturated aqueous sodium thiosulfate (10 ml) and extracted with diethyl ether (3×10 ml). The combined organic extracts were washed with brine (10 ml), dried over magnesium sulfate, filtered and concentrated in vacuo. Purification via flash chromatography (SiO$_2$, ethyl acetate/ petroleum ether, 1:3, v/v) afforded the title compound (0.04 g, 24%) as a colourless gum. oil. $\delta_H$ (CDCl$_3$) 0.22 (6H, s), 0.27 (6H, s), 0.96 (9H, s), 1.03 (9H, s), 1.40–1.53 (2H, m), 1.82–1.94 (6H, m), 2.18 (2H, t), 2.62 (2H, t), 2.90 (1H, m), m), 6.33 (1H, d), 6.42 (1H, dd) and 6.96 (1H, d).

Preparation 27 trans-4-(2,4-Bis{[tert-butyl(dimethyl)silyl] oxy}phenyl)cyclohexyl Phenylcarbamate N,N-Diisopropylethylamine (100 μl) and phenylisocyanate (55 μl) were added to a stirred solution of trans-4-(2,4-bis{[tert-butyl(dimethyl)silyl]oxy}phenyl)cyclohexanol (50 mg) in anhydrous dichloromethane (2 ml). After 96 hr at 40° C., the reaction mixture was partitioned between ethyl acetate (50 ml) and water (50 ml). The aqueous layer was extracted with ethyl acetate (2×50 ml). The combined organic extracts were washed with brine (50 ml); dried over magnesium sulfate and evaporated in vacuo. The residue was purified using flash column chromatography (SiO$_2$, ethyl acetate/petrol, 1:2 v/v) to give the title compound (50 mg, 79%) as a pale yellow gum. $\delta_H$(CDCl$_3$) 0.00 (6H, s), 0.06 (6H, s), 0.80 (9H, s), 0.83 (9H, s), 1.30–1.40 (4H, m), 1.70–1.75 (2H, m), 2.00–2.05 (2H, m), 2.60–2.70 (1H, m), 4.55–4.65 (1H, m), 6.10 (1H, d), 6.23 (1H, dd), 6.40 (1H, s), 6.76–7.20 (5H, m).

Preparation 28 tert-Butyl[5-{[tert-butyl(dimethyl)silyl]oxy}-2-(4-methylenecyclohexyl)phenoxy] Dimethylsilane To a round bottomed flask was added methyltriphenylphosphonium bromide (0.99 g) and tetrahydrofuran (30 ml). The resulting suspension was cooled to 0° C. and potassium tert-butoxide (0.31 g) was added in one portion. The resulting solution was stirred at 0° C. for 0.5 hr, then 4-(2,4-bis{[tert-butyl(dimethyl)silyl]oxy}phenyl) cyclohexanone (0.60 g) added as a solution in tetrahydrofuran (10 ml). The solution was stirred for 1 hr at 0° C., then allowed to warm to room temperature and stirred for 15 hr. The reaction mixture was partitioned between ethyl acetate (20 ml) and saturated ammonium chloride solution (20 ml). The layers were separated and the aqueous layer extracted with ethyl acetate (2×20 ml). The combined organic phases were washed with brine (20 ml), dried over magnesium sulfate, filtered and concentrated in vacuo. Purification via flash chromatography (SiO$_2$, ethyl acetate/petroleum ether, 1:9 v/v) furnished the title compound (0.56 g, 93%) as a colourless oil. $\delta_H$ (CDCl$_3$): 0.17 (6H, s), 0.24 (6H, s), 0.97 (9H, s), 1.03 (9H, s), 1.34–1.47 (2H, m), 1.86–1.94 (2H, m), 2.10–2.20 (2H, m), 2.35–2.43 (2H, m), 3.00 (1H, ft), 4.64 (2H, m), 6.29 (1H, d), 6.39 (1H, dd), 6.94 (1H, d).

Preparation 29 trans-4-(2,4-Bis{[tert-butyl(dimethyl)silyl]oxy}phenyl)cyclohexyl (2R)-2-[(tert-butoxycarbonyl)amino]-3-phenylpropanoate To a round bottomed flask was added N-(tert-butoxycarbonyl)-L-phenylalanine (109 mg) and dichloromethane (10 ml). To the solution was added diisopropylcarbodiimide (64 μl), trans-4-(2,4-bis{[tert-butyl(dimethyl)silyl]oxy}phenyl)cyclohexanol (150 mg) and 4-dimethyl aminopyridine (catalytic). The solution was stirred at room temperature for 15 hr. The reaction mixture was partitioned between water (20 ml) and dichloromethane (30 ml), the layers were separated and the aqueous phase was extracted with dichloromethane (2×30 ml). The combined organic phases were washed with brine (20 ml), dried over magnesium sulfate, filtered and concentrated in vacuo. Purification via flash chromatography (SiO$_2$, ethyl acetate/petroleum ether, 1:19 v/v) furnished the title compound (236 mg, 100%) as a yellow oil. $\delta_H$ (CDCl$_3$): 0.18 (6H, s), 0.23 (6H, s), 0.97 (9H, s), 1.03 (9H, s), 1.35–1.47 (13H, m), 1.80–1.90 (2H, m), 1.95–2.07 (2H, m), 2.77–2.86 (1H, m), 3.05–3.12 (2H, m), 4.49–4.58 (1H, m), 4.73–4.82 (1H, m), 4.93–5.00 (1H, m), 6.28 (1H, d), 6.40 (1H, dd), 6.93 (1H, d), 7.15 (2H, d), 7.19–7.31 (3H, m).

Preparation 30

Benzyl [4-(2,4-bis{[tert-butyl(dimethyl)silyl]oxy}phenyl)cyclohexylidene]acetate To a round bottomed flask was added 4-(2,4-bis{[tert-butyl(dimethyl)silyl]oxy}phenyl) cyclohexanone (1.09 g), xylene (65 ml) and benzyl (triphenylphosphoranylidene)acetate (4.20 g) and the reaction mixture was heated under reflux for 13 hr. The solvent was removed in vacuo and the residue triturated with petroleum ether (3×150 ml), and the combined organic phases were concentrated in vacuo. Purification via flash chromatography (SiO$_2$, petroleum ether/ethyl acetate, gradient elution using 100, 99:1, 70:1 then 50:1, v/v) furnished the title compound (0.76 g, 54%) as a white solid. m/z (ES$^+$) 467 (M+H$^+$).

Preparation 31

N'-[4-(2,4-Bis{[tert-butyl(dimethyl)silyl]oxy}phenyl)cyclohexylidene]-4-methylbenzenesulfonohydrazide To a round bottomed flask was added 4-(2,4-bis{[tert-butyl(dimethyl)silyl]oxy}phenyl) cyclohexanone (0.5 g) and ethanol (10 ml), and the solution heated to allow dissolution. The stirred solution was cooled to 30° C., p-toluenesulfonyl hydrazide (0.24 g) was added, and the reaction mixture stirred at room temperature for 1.5 hr. The reaction mixture was filtered, and the filtrate was concentrated in vacuo. Purification via flash chromatography (SiO$_2$, ethyl acetate/petroleum ether 3:7 v/v) furnished the title compound (0.60 g, 87%) as a white solid. oil. $\delta_H$ (CDCl$_3$): 0.18 (6H, s), 0.22 (6H, s), 0.95 (9H, s), 0.99 (9H, s), 1.37–1.49 (1H, m), 1.49–1.62 (1H, m), 1.84–2.02 (3H, m), 2.17–2.27 (1H, m), 2.43 (3H, s), 2.53–2.61 (1H, m), 2.74–2.82 (1H, m), 3.07 (1H, tt), 6.28 (1H, d), 6.38 (1H, dd), 6.86 (1H, d), 7.13 (1H, br s), 7.31 (2H, d), 7.86 (2H, d).

Preparation 32 trans-N-[4(2,4-Bis{[tert-butyl(dimethyl)silyl]oxy}phenyl)cyclohexyl]-3-nitrobenzamide To a round bottomed flask was added trans-4-(2,4-bis{[tert-butyl(dimethyl)silyl]oxy}phenyl)cyclohexylamine (80 mg) and dichloroethane (7 ml), and the reaction mixture heated to 40° C. To the stirred solution was added triethylamine (100 μl), a solution of 3-nitrobenzoyl chloride (101 mg) in tetrahydrofuran/dichloromethane (6 ml, 1:1 v/v) and 4-dimethylamino pyridine (catalytic). The reaction mixture was heated at 40° C. for 24 hr, and then room temperature for 24 hr. The reaction mixture was diluted with dichloromethane (20 ml) and aqueous sodium hydroxide (16 ml, 0.5M) was added. After stirring for 0.2 hr, the layers were separated and the aqueous layer extracted with dichloromethane (2×10 ml). The combined organic phases were washed with saturated sodium hydrogen carbonate solution (15 ml) and brine (16 ml), dried over magnesium sulfate, filtered and concentrated in vacuo. Purification via flash chromatography (SiO$_2$, ethyl acetate/petroleum ether, gradient elution using 1:10, 1:8, 1:5, then 1:4, v/v) furnished the title compound (52 mg, 49%) as a colourless gum. $\delta^6$H (CDCl$_3$): 0.18 (6H, s), 0.24 (6H, s), 0.97 (9H, s), 1.03 (9H, s), 1.34–1.61 (4H, m), 1.87–1.96 (2H, m), 2.17–2.27 (2H, m), 2.88 (1H, tt), 4.01–4.13 (1H, m), 6.08 (1H, d), 6.29 (1H, d), 6.43 (1H, dd), 6.97 (1H, d), 7.65 (1H, t), 8.18 (1H, d), 8.35 (1H, d), 8.57 (1H, s).

Preparation 33 cis-N-Benzoyloxy-N[2,4-bis{[tert-butyl(dimethyl)silyl]oxy}phenyl)cyclohexyl]-3-cyanobenzamide General Procedure A A round bottomed flask was charged with cis-O-benzoyl-N[4–2,4-bis{[tert-butyl(dimethyl)silyl]oxy}phenyl)cyclohexyl]hydroxylamine (0.05 g), dichloromethane (2 ml), triethylamine (0.1 ml) and 3-cyanobenzoyl chloride (0.044 g). After stirring for 1 hr, the mixture was diluted with dichloromethane (10 ml) and washed with 2M HCl (5 ml). The organic layer was separated, washed with saturated aqueous sodium hydrogen carbonate (5 ml), brine (5 ml), dried over magnesium sulfate, filtered and concentrated in vacuo. Purification via flash chromatography (SiO$_2$, ethyl acetate/petroleum ether, 1:3, v/v) afforded the title compound (20 mg, 32%) as a colourless oil. $\delta_H$(COCl$_3$) 0.19 (6H, s), 0.26 (6H, s), 0.94 (9H, s), 1.03 (9H, s), 1.68–1.88 (8H, m), 3.00 (1H, m), 4.73 (1H, m), 6.29 (1H, d), 6.37 (1H, dd), 6.93 (1H, d), 7.40–7.49 (3H, m); 7.63 (2H, m) and 7.88–7.97 (4H, m).

Preparation 34 cis-N-Benzoyloxy-N[2,4-bis{[tert-butyl(dimethyl)silyl]oxy}phenyl)cyclohexyl]-4-(triflurormethyl)benzamide Preparation 34 was prepared according to General Procedure A above from cis-O-benzoyl-N-[4–2,4-bis{[tert-butyl(dimethy)silyl]oxy}phenyl)cyclohexyl]hydroxylamine (0.075 g) and 4-(trifluoromethyl)benzoyl chloride (0.04 ml) to give the title compound as a colourless oil (58 mg, 59%).

$\delta_H$(CDCl$_3$) 0.17 (6H, s), 0.22 (6H, s), 0.94 (9H, s), 1.00 (9H, s), 1.70–1.88 (8H, m), 2.97 (1H, m), 4.69 (1H, m), 6.30 (2H, m), 6.88 (1H, d), 7.46 (2H, m), 7.62 (3H, m), 7.78 (2H, d) and 7.92 (2H, d).

Preparation 35 cis-N-Benzoyloxy-N[2,4-bis{[tert-butyl(dimethyl) silyl]oxy}phenyl)cyclohexyl]-4-methoxybenzamide Preparation 35 was prepared according to General Procedure A above from cis-O-benzoyl-N[4–2,4-bis{[tert-butyl(dimethyl)silyl]oxy}phenyl)cyclohexyl]hydroxylamine (0.075 g) and p-anisoyl chloride (0.046 g) to give the title compound (33 mg, 35%) as a colourless oil. $\delta_H$ (CDCl$_3$) 0.20 (6H, s), 0.26 (6H, s), 0.94 (9H, s), 1.00 (9H, s), 1.70–1.97 (8H, m), 2.98 (1H, m), 3.78 (3H, s), 4.68 (1H, s), 6.27 (1H, d), 6.33 (1H, dd), 6.83 (2H, d), 6.93 (1H, d), 7.44 (2H, t), 7.60 (1H, t), 7.68 (2H, m) and 7.97 (2H, m).

Preparation 36

(±)-Methyl[4-(2,4-bis{[tert-butyl(dimethyl) silyl]oxy}phenyl)cyclohexylidene] Acetate To a flask was charged sodium hydride (60% dispersion in mineral oil) (83 mg) and THF (75 ml) and the mixture cooled to 0° C. Trimethylphosphonoacetate (0.28 ml) was added and the reaction mixture stirred for 1 hr at room temperature before adding a solution of 4-(2,4-bis{[tert-butyl(dimethyl)silyl]oxy}phenyl)cyclohexanone (0.75 g) in THF (15 ml), and the mixture heated under reflux for 45 min. The reaction mixture was cooled to room temperature, poured into saturated ammonium chloride solution (100 ml) and extracted with ethyl acetate (3×100 ml). The combined organic extracts were washed with brine (50 ml), dried over magnesium sulfate, filtered and concentrated in vacuo. Purification via flash chromatography (SiO$_2$, petroleum ether) afforded the title compound (0.57 g, 67%) as a colourless solid. $\delta_H$ (CDCl$_3$) 0.22 (6H, s), 0.31 (6H, s), 1.03 (9H, s), 1.13 (9H, s), 1.49–1.66 (2H, m), 1.97–2.08 (4H, m), 2.33–2.51 (2H, m), 3.20 (1H, m), 3.73 (3H, s), 5.73 (1H, s), 6.38 (1H, d), 6.44 (1H, dd) and 7.03 (1H, d).

Example 1

4(1,4-Dioxaspiro[4.5]dec-8-yl)-1,3-benzenediol

A round bottomed flask was charged with 5-benzyloxy-21,4-dioxaspiro[4.5]dec-7-en-8-yl)phenol (6.90 g), ethanol (300 ml) and palladium (2.00 g, 10%,on activated carbon). The reaction vessel was then evacuated and placed under a hydrogen atmosphere. This process was repeated 15 times before stirring vigorously for 64 hr under a hydrogen atmosphere. The reaction mixture was filtered through a celite plug, washing with ethyl acetate. The filtrate was concentrated in vacuo, furnishing the title compound (5.10 g, 100%) as a solid. $\delta_H$(CD$_3$OD) 1.65–1.87 (8H, m), 2.86–2.90 (1H, m), 3.90–4.06 (4H, m), 6.27 (1H, dd), 6.29 (1H, d), 6.92 (1H, d); m/z (ES$^+$) 251 (M+H$^+$).

Example 2

(±)-{4-[2,4-Dihydroxyphenyl] cyclohexylidene}acetic Acid

A round bottomed flask was charged with (±)-{4-[2,4-bis (methoxymethoxy)phenyl]cyclohexylidene}acetic acid (25 mg), acidic Dowex resin (75 mg) and methanol (15 ml) then stirred at 60° C. for 3 hr. The reaction mixture was filtered through a celite plug, washing with methanol. The solvent was removed under reduced pressure to give an oil which was purified by preparative TLC (ethyl acetate/petroleum ether, 3:1, v/v), furnishing the title compound (6.5 mg, 35%) as an oil. $\delta_H$(CD$_3$OD) 1.22–1.40 (2H, m), 1.90–2.10 (4H, m), 2.36–2:40 (2H, m), 3.08 (1H, tt), 5.62 (1H, s), 6.20 (1H, dd), 6.25 (1H, d), 6.84 (1H, d); m/z (ES$^+$) 339 (M+H$^+$).

Example 3

(±)-[4-(2,4-Dihydroxyphenyl)cyclohexylidene] acetonitrile

To a round bottomed flask was added (±)-{4-[2,4-bis (methoxymethoxy)phenyl]cyclohexylidene}acetonitrile (141 mg) and methanol (5 ml). The reaction mixture was stirred, the solution was heated under reflux temperature and aqueous hydrochloric acid (5 ml, 1.0M) was added slowly. Heating was continued for 1 hr and the reaction mixture was allowed to cool to room temperature prior to the addition of saturated aqueous sodium bicarbonate solution (12 ml). The reaction mixture was partitioned between ethyl acetate (30 ml) and water (10 ml). The aqueous layer was extracted with ethyl acetate (3×15 ml) and the combined organic layers washed with brine (20 ml), dried over magnesium sulfate, filtered and concentrated in vacuo. The residue was purified via flash column chromatography (SiO$_2$, ethyl acetate/ petroleum ether, 1:1, v/v) to afford the title compound (90 mg, 88%) as a white solid. m/z (ES$^-$) 228 (M–H$^+$); $\delta_H$ (CD$_3$OD) 1.56–1.68 (2H, m), 2.02–2.14 (2H, m), 2.33–2.48 (2H, m), 2.57 (1H, m), 3.01 (1H, m), 3.14 (1H, m), 5.31 (1H, s), 6.27 (1H, dd), 6.32 (1H, d), 6.80 (1H, d).

Example 4 cis-N-[4-(2,4-Dihydroxyphenyl)cyclohexyl]-N-hydroxybenzamide

A round bottomed flask was charged with cis-O-benzoyl-N-[4–2,4-bis{[tert-butyl(dimethyl)silyl]oxy}phenyl) cyclohexyl]hydroxylamine, (0.04 g), dichloromethane (2 ml), triethylamine (0.05 ml) and benzoyl chloride (0.025 ml). After stirring for 0.5 hr, the mixture was diluted with dichloromethane (15 ml) and washed with 2M HCl (5 ml). The organic layer was separated, washed with saturated aqueous sodium hydrogen carbonate (5 ml), brine (5 ml), dried over magnesium sulfate, filtered and concentrated in vacuo affording a crystalline solid. This solid was dissolved in ethanol (2 ml) and sodium hydroxide (2M, 0.25 ml) added. After stirring overnight, the solution was concentrated in vacuo, diluted with water (2 ml) and extracted with ethyl acetate (5 ml). The aqueous layer was separated, acidified with 2M HCl and extracted with ethyl acetate (3×5 ml). The combined organic phases were washed with brine (5 ml), dried over magnesium sulfate, filtered and concentrated in vacuo. Purification via flash chromatography (SiO$_2$, ethyl acetate/petroleum ether, 2:1, v/v) afforded the title compound (0.013 g, 55%) as an off-white powder. $\delta_H$ (CD$_3$OD) 1.68–1.82 (4H, m), 2.03–2.18 (4H, m), 3.01 (1H, m), 4.40 (1H, m), 6.20–6.26 (2H, m), 7.02 (1H, d), 7.38–7.50 (3H, m) and 7.60 (2H, m); m/s(ES$^+$) 328.16 (M+H)$^+$.

Example 5 cis-N-[4(2,4-Dihydroxyphenyl)cyclohexyl] benzamide

A solution of cis-N-[4–2,4-bis{[tert-butyl(dimethyl)silyl] oxy}phenyl)cyclohexyl]benzamide (0.08 g) in methanol (2 ml) was stirred rapidly with Amberlyst A-26 (fluoride resin) (0.25 g) for 17 hr. The mixture was filtered through a pad of celite and concentrated in vacuo. Purification via flash chromatography (SiO$_2$, ethyl acetate/petroleum ether, 3:1, v/v) afforded the title compound (0.025 g, 54%) as a colourless solid. $\delta_H$ (CD$_3$OD) 1.70–1.91 (6H, m), 1.98–2.10 (2H, m), 2.88 (1H, m), 4.23 (1H, m), 6.21–6.30 (2H, m), 6.99 (1H, d), 7.40–7.57 (3H, m) and 7.81 (2H, d); m/s(ES$^+$) 312.13 (M+H)$^+$.

Example 6 trans-4-{4-[(Z)-benzylidene(oxido)amino] cyclohexyl}-1,3-benzenediol cis-O-Benzoyl-Nbenzyl-N-[4–2,4-bis{[tert-butyl (dimethyl)silyl]oxy}phenyl)cyclo hexyl] hydroxylamine (50 mg) was dissolved in a mixture of methanol (1 ml) and THF (2 ml) and sodium hydroxide (2M, 0.4 ml) was added with stirring. After 2 hr, the solution was acidified with 2M HCl and extracted with ethyl acetate (3×11 ml). The combined organic extracts were washed with saturated aqueous sodium hydrogen carbonate (5 ml), brine (5 ml), dried over magnesium sulfate, filtered and concentrated in vacuo. Purification via flash chromatography (SiO$_2$, ethyl acetate/petroleum ether, 3:1, v/v) afforded the title compound (2 mg, 8%) as colorless crystals. oil. $\delta_H$ (CD$_3$OD) 1.60–1.72 (2H, m), 2.00 (2H, m), 2.08–2.12 (4H, m), 2.88 (1H, m), 4.13 (1H, m), 6.23 (1H, dd), 6.26 (1H, d), 6.91 (1H, d), 7.47 (3H, m), 7.96 (1H, s) and 8.28 (2H, m); m/s(ES$^+$) 312.16 (M+H)$^+$.

Example 7 trans-N-[4-(2,4-Dihydroxyphenyl)cyclohexyl]-N-hydroxybenzamide

A round bottomed flask was charged with trans-benzoyl-N-[4–2,4-bis{[tert-butyl(dimethyl)silyl]oxy}phenyl) cyclohexyl]hydroxylamine (0.16 g), dichloromethane (3 ml), triethylamine (0.05 ml) and benzoyl chloride (0.05 ml). After stirring for 1 hr, the mixture was diluted with dichloromethane (15 ml) and washed with 2M HCl (5 ml). The organic layer was separated, washed with saturated aqueous sodium hydrogen carbonate (5 ml), brine (5 ml), dried over magnesium sulfate, filtered and concentrated in vacuo affording a crystalline solid. This solid was dissolved in methanol (2 ml) and stirred rapidly with Amberlyst A-26 (fluoride resin) (0.5 g) for 24 hr. The mixture was filtered through a pad of celite and concentrated in vacuo. This residue was dissolved in ethanol (2 ml) and sodium hydroxide (2M, 0.5 ml) added with stirring. After stirring for 10 min the solution was acidified with 2M HCl, diluted with water (2 ml) and extracted with ethyl acetate (3×10 ml). The combined organic extracts were washed with brine (5 ml), dried over magnesium sulfate, filtered and concentrated in vacuo. Purification via flash chromatography (SiO$_2$, ethyl acetate/petroleum ether, 3:1, v/v) afforded the title compound (0.025 g, 20%) as a yellow powder. $\delta_H$ d$_6$-DMSO (45° C.) 1.38–1.52 (2H, m), 1.76–1.89 (6H, m), 2.84 (1H, m), 4.22 (1H, m), 6.16 (1H, dd), 6.23 (1H, d), 6.81 (1H, d), 7.38 (3H, m), 7.59 (2H, m), 8.80 (1H, s), 8.90 (1H, s) and 9.38 (1H, s); m/s(ES$^+$) 328.60 (M+H)$^+$, 369.59 (MH+MeCN)$^+$.

Example 8 syn-8-(2,4-Dihydroxyphenyl)-1-oxaspiro[4.5]decan-2-one

A solution of syn-8-(2,4-bis{[tert-Butyl(dimethylsilyl)] oxy}phenyl-1-oxaspiro[4.5]decan-2-one (0.04 g) in metha-nol (4 ml) was stirred rapidly with Amberlyst A-26 (fluoride resin) (0.2 g) for 17 hr. Acetic acid (0.5 ml) was added and stirring continued for a further 1 hr. The mixture was then filtered through a pad of celite and concentrated in vacuo. Purification via flash chromatography (SiO$_2$, ethyl acetate/petroleum ether, 2:1, v/v) afforded the title compound (0.007 g, 33%) as a colourless oil. $\delta_H$ (CD$_3$OD) 1.53–1.68 (2H, m), 1.80–1.95 (6H, m), 2.23 (2H, t), 2.86 (2H, t), 2.84 (1H, m), 6.22 (1H, dd), 6.25 (1H, d) and 6.88 (1H, d); m/s(ES$^+$) 304.17 (MH+MeCN)$^+$.

Example 9 cis-N-[4-(2,4-Dihydroxyphenyl)cyclohexyl]-N'-phenylurea

A solution of phenylisocyanate (0.015 ml, 0.13 mmol), triethylamine (0.03 ml), 4-dimethylaminopyridine (catalytic) and cis-4-(2,4-bis{[tert-butyl(dimethyl)silyl] oxy}phenyl) cyclohexylamine (0.043 g) in dichloroethane (4 ml) was stirred at room temperature for 17 hr. The mixture was partitioned between saturated aqueous sodium hydrogen carbonate (5 ml) and dichloromethane (5 ml). The aqueous phase was extracted with dichloromethane (2×5 ml) and the combined organic extracts washed with brine (7 ml), dried over magnesium sulfate, filtered and concentrated in vacuo. The resulting oil was dissolved in dichloromethane (6 ml) and stirred rapidly with water (3 ml) and trifluoroacetic acid (3 ml) for 60 hr. Toluene (15 ml) was added and the solution concentrated in vacuo. Purification via flash chromatography (SiO$_2$, ethyl acetate/petroleum ether) afforded the title compound (0.013 g, 30%) as a colourless solid. $\delta_H$ (CD$_3$OD) 1.32–1.46 (2H, m), 1.53–1.69 (2H, m), 1.90 (2H, m), 2.17 (2H, m), 2.83 (1H, m), 3.65 (1H, m), 6.28 (2H, m), 6.94 (1H, d), 7.00 (1H, m), 7.27 (2H, m) and 7.38 (2H, m); m/s(ES$^+$) 327.20 (M+H)$^+$.

Example 10 trans-Phenyl-4-(2,4-dihydroxyphenyl) cyclohexylcarbamate

A solution of phenylchloroformate (0.045 ml, 0.36 mmol), triethylamine (0.085 ml), 4-dimethylaminopyridine (catalytic) and trans-4(2,4-bis{[tert-butyl(dimethyl)silyl] oxy}phenyl) cyclohexylamine (0.043 g) in dichloroethane (11 ml) was stirred at room temperature for 60 hr. The mixture was partitioned between saturated aqueous sodium carbonate (15 ml) and dichloromethane (15 ml). The aqueous phase was extracted with dichloromethane (2×15 ml) and the combined organic extracts washed with brine (20 ml), dried over magnesium sulfate, filtered and concentrated in vacuo. Purification via flash chromatography (SiO$_2$, ethyl acetate/petroleum ether) afforded a colourless gum. This was dissolved in dichloromethane (15 ml) and warmed with a mixture of water (7.5 ml) and trifluoroacetic acid (7.5 ml) at 80° C. for 17 hr. On cooling, toluene (25 ml) was added and the solution concentrated in vacuo. Methanol (25 ml) was added and the solution again concentrated in vacuo. Purification via flash chromatography (SiO$_2$, ethyl acetate/petroleum ether) afforded the title compound (0.013 g, 13%) as a colourless solid. $\delta_H$ (CD$_3$OD) 1.44–1.63 (4H, m), 1.96 (2H, m), 2.13 (2H, m), 2.86 (1H, m), 3.55 (1H, m), 6.30 (2H, m), 6.92 (1H, d), 7.12 (2H, m), 7.22 (1H, m) and 7.40 (2H, m); m/s(ES$^+$) 328.26 (M+H)$^+$.

Example 11 cis-N-Benzyl-N-[4-(2,4-dihydroxyphenyl) cyclohexyl]-N'-ethylurea

A solution of ethylisocyanate (0.038 ml, 0.48 mmol), triethylamine (0.065 ml) and cis-N-benzyl-N-[4-(2,4-bis{

[tert-butyl(dimethyl)silyl]oxy}phenyl)cyclohexyl]amine (0.122 g) in dichloroethane (10 ml) was stirred at room temperature for 60 hr. The reaction mixture was partitioned between water (10 ml) and dichloromethane (10 ml). The aqueous layer was separated and extracted with dichloromethane (2×10 ml) and the combined organic extracts washed with brine (10 ml), dried over magnesium sulfate, filtered and evaporated in vacuo. The resulting residue was dissolved in dichloromethane (15 ml) and warmed with a mixture of water (7.5 ml) and trifluoroacetic acid (7.5 ml) at 80° C. for 17 hr. Toluene (25 ml) was then added and the mixture concentrated in vacuo. Methanol (25 ml) was then added and the mixture again concentrated in vacuo. Purification via flash chromatography (SiO$_2$, ethyl acetate/petroleum ether) afforded the title compound (0.016 g, 19%) as a colourless solid. $\delta_H$ (CD$_3$OD) 1.08 (3H, t), 1.57–1.88 (6H, m), 2.12 (2H, m), 3.16 (1H, m), 3.24 (2H, m), 4.17 (1H, m), 4.52 (2H, s), 6.09 (1H, t), 6.24 (1H, dd), 6.29 (1H, d), 6.98 (1H, d) and 7.22–7.37 (5H, m). m/s(ES$^+$) 369.54 (M+H)$^+$.

Example 12 cis-N-Benzyl-N-[4-(2,4-dihydroxyphenyl)cyclohexyl]propanamide cis-N-Benzyl-N-[4-(2,4-bis{[tert-butyl(dimethyl)silyl]oxy}phenyl)cyclohexyl] amine (0.084 g) was dissolved in dichloroethane (7 ml), and triethylamine (0.045 ml) and 4-dimethylaminopyridine (catalytic) added. Propionyl chloride (0.028 ml) was then added, and the mixture stirred at room temperature for 60 hr. The reaction mixture was partitioned between dichloromethane (10 ml) and saturated aqueous sodium hydrogen carbonate (10 ml). The aqueous layer was extracted with dichloromethane (2×10 ml) and the combined organic extracts washed with brine (10 ml), dried over magnesium sulfate, filtered and concentrated in vacuo. The residue was dissolved with stirring in dichloroethane (16 ml) and heated with a mixture of water (10 ml), methanol (5 ml) and trifluoroacetic acid (10 ml) at 80° C. for 17 hr. Toluene (25 ml) was then added and the mixture concentrated in vacuo. Methanol (25 ml) was then added and the mixture again concentrated in vacuo. Purification via flash chromatography (SiO$_2$, ethyl acetate/petroleum ether) afforded the title compound (0.021 g, 37%) as a colourless solid. R$_f$ 0.20 (ethyl acetate/petroleum ether, 1:1, v/v); m/s(ES$^+$) 354.17 (M+H)$^+$.

Example 13 trans-4-(2,4-Dihydroxyphenyl)cyclohexyl phenylcarbamate trans-4-(2,4-Bis{[tert-butyl(dimethyl)silyl]oxy}phenyl)cyclohexylphenylcarbamate (55 mg) and fluoride resin (300 mg) were stirred in methanol (10 ml) at room temperature. After 16 hr, the reaction mixture was filtered through a pad of celite, which was washed with a copious volume of methanol. The filtrate was concentrated in vacuo and the residue was purified by flash column chromatography (SiO$_2$, ethyl acetate/petrol, 1:1 v/v) to give the title compound (17 mg, 60%) as an orange solid. $\delta_H$ (CD$_3$OD) 1.20–1.30 (1H, m), 1.40–1.60 (4H, m), 1.80–2.20 (3H, m), 2.75–2.90 (1H, m), 3.20–3.40 (1H, m), 4.60–4.80 (1H, m), 6.20–6.30 (2H, m), 6.90–7.00 (2H, m), 6.20–6.30 (2H, m), 7.30–7.40 (2H, m); m/z (ES$^+$) 328 (M+H$^+$).

Example 14 trans-Ethyl[({[4-(2,4-dihydroxyphenyl)cyclohexyl]oxy}carbonyl)amino]acetate

N,N-Diisopropylethylamine (398 μl) and ethylisocyanoacetate (154 μl) were added to a stirred solution of trans-4-(2,4-bis{[tert-butyl(dimethyl)silyl]oxy}phenyl)cyclohexanol (200 mg) in anhydrous dimethylformamide (1 ml). After 16 hr at 50° C., the reaction mixture was partitioned between ethyl acetate (50 ml) and water (50 ml) and stirred for 16 hr at room temperature. The aqueous layer was extracted with ethyl acetate (2×50 ml). The combined organic extracts were washed with brine (50 ml), dried over magnesium sulfate and evaporated in vacuo. The residue was purified using flash column chromatography (SiO$_2$, ethyl acetate/petrol, 1:1 v/v) to give the title compound (70 mg, 70%) as a pale yellow gum. $\delta_H$ (CD$_3$OD) 1.30–1.40 (3H, m), 1.50–1.70 (3H, m), 1.88–2.24 (4H, m), 2.76–2.90 (1H, m), 3.90 (2H, s), 4.10–4.30 (3H, m), 4.58–4.70 (1H, m), 6.26–6.32 (2H, m), 6.94 (1H, d); m/z (ES$^+$) 338 (M+H$^+$).

Example 15 trans-4-(2,4-Dihydroxyphenyl)cyclohexyl benzylcarbamate

N,N-Diisopropylethylamine (398 μl) and benzylisocyanate (154 μl) was added to a stirred solution of trans-4-(2,4-bis{[tert-butyl(dimethyl)silyl]oxy}phenyl)cyclohexanol (200 mg) in anhydrous dimethylformamide (1 ml). After 16 hr at 50° C., the reaction mixture was partitioned between ethyl acetate (50 ml) and water (50 ml) and stirred for 16 hr at room temperature. The aqueous layer was extracted with ethyl acetate (2×50 ml). The combined organic extracts were washed with brine (50 ml), dried over magnesium sulfate and evaporated in vacuo. The residue was purified using flash column chromatography (SiO$_2$, ethyl acetate/petrol, 1:1 v/v) to give the title compound (20 mg, 13%) as a pale yellow gum. $\delta_H$ (CD$_3$OD) 1.40–1.60 (4H, m), 1.80–1.90 (2H, m), 1.00–1.20 (2H, m), 2.70–2.82 (1H, m), 4.20–4.30 (2H, s), 4.55–4.65 (1H, m), 6.20–6.30 (2H, m), 6.86 (1H, d), 7.15–7.40 (5H, m); m/z (ES$^+$) 342 (M+H$^+$).

Example 16 trans-4-(2,4-Dihydroxyphenyl)cyclohexyl Ethyl Carbonate

Triethylamine (0.5 ml), ethylchloroformate (0.5 ml) and dimethylaminopyridine (cat.) were added to a stirred solution of trans-4-(2,4-bis{[tert-butyl(dimethyl)silyl]oxy}phenyl)cyclohexanol (250 mg) in anhydrous dichloromethane (5 ml). After 72 hr at room temperature, the reaction mixture was partitioned between-ethyl-acetate (50 ml) and water (50 ml). The aqueous layer was extracted with ethyl acetate (2×50 ml). The combined organic extracts were washed with brine (50 ml), dried over magnesium sulfate and evaporated in vacuo. The residue was dissolved in methanol (5 ml) and was stirred with fluoride resin (500 mg) for 16 h at room temperature. The resin was filtered through a pad of celite, which was washed well with methanol. The combined filtrates were concentrated in vacuo. The residue was purified using flash column chromatography (SiO$_2$, ethyl acetate/petrol, 1:2 v/v), and then preparative HPLC to give the title compound (4 mg, 3%) as a cream solid. $\delta_H$ (CD$_3$OD) 1.20–1.30 (3H, m), 1.40–1.60 (4H, m), 1.80–1.95 (2H, m), 2.00–2.20 (2H, m), 2.70–2.84 (1H, m), 4.06–4.20 (2H, m), 4.50–4.60 (1H, m), 6.20–6.30 (2H, m), 6.86 (1H, d); m/z (ES$^-$) 279 (M–H$^-$).

Example 17 trans-Methyl[({[4-(2,4-dihydroxyphenyl)cyclohexyl]oxy}carbonyl)amino]acetate

N,N-Diisopropylethylamine (6.0 ml) and ethylisocyanoacetate (3.6 ml) were added to a stirred solution of trans-4-(2,4-bis{[tert-butyl(dimethyl)silyl]oxy}phenyl) cyclohexanol (3.0 g) in anhydrous dimethylformamide (10 ml). After 16 hr at 50° C., the reaction mixture was partitioned between ethyl acetate (300 ml) and water (300 ml). The aqueous layer was extracted with ethyl acetate (2×300 ml). The combined organic extracts were washed with brine (100 ml), dried over magnesium sulfate and evaporated in vacuo. The residue was dissolved in methanol (100 ml) and was stirred with fluoride resin (2 g) for 16 hr at room temperature. The suspension was filtered through a pad of celite, which was washed well with methanol. The combined filtrates were concentrated in vacuo and the residue was purified using flash column chromatography (SiO$_2$, ethyl acetate/petrol, 1:3 v/v) to give the title compound (812 mg, 37%) as a pale yellow gum. $\delta_H$ (CD$_3$OD) 1.45–1.55 (4H, m), 1.80–1.90 (2H, m), 2.00–2.10 (2H, m), 2.70–2.80 (1H, m), 3.70 (3H, s), 3.80 (2H, s), 4.50–4.64 (1H, m), 6.00–6.25 (2H, m), 6.9 (1H, d); m/z (ES$^+$) 324 (M+H$^+$).

Example 18 trans-4-(2,4-Dihydroxyphenyl)cyclohexyl methyl Imidodicarbonate

N,N-Diisopropylethylamine (497 μl) and ethylisocyanatoformate (177 μl) were added to a stirred solution of trans-4-(2,4-bis{[tert-butyl(dimethyl)silyl]oxy}phenyl) cyclohexanol (250 mg) in anhydrous dimethylformamide (2 ml). After 120 hr at 50° C., the reaction mixture was partitioned between ethyl acetate (50 ml) and water (50 ml). The aqueous layer was extracted with ethyl acetate (2×50 ml). The combined organic extracts were washed with brine (50 ml), dried over magnesium sulfate and evaporated in vacuo. The residue was dissolved in methanol (10 ml) and was stirred with fluoride resin (300 mg) for 16 hr at room temperature. The suspension was filtered through a pad of celite, which was washed well with methanol. The combined filtrates were concentrated in vacuo and the residue was purified using flash column chromatography (SiO$_2$, ethyl acetate/petrol, 1:3 v/v) and then preparative HPLC to give the title compound (4 mg, 2%) as a pale yellow gum. $\delta_H$ (CD$_3$OD) 1.20–1.40 (4H, m), 1.55 (3H, t), 1.80–1.90 (2H, m), 2.00–2.18 (2H, m), 2.72–2.82 (1H, m), 4.20 (2H, q), 6.20–6.25 (2H, m), 6.84 (1H, d); m/z (ES$^-$) 322 (M–H$^-$).

Example 19 cis/trans-4-(1-Oxaspiro[2.5]oct-6-yl)-1,3-benzenediol

A stirred suspension of dimethylsulfoxide (17 ml) and sodium hydride (0.69 g, 60% dispersion in mineral oil) was heated to 70° C. under argon. After 1 hr, the solution was cooled to room temperature and was added to a solution of trimethylsulfonium iodide (1.5 g) in dimethylsulfoxide (8 ml) added at 0° C. A solution of 4-(2,4-dihydroxyphenyl) cyclohexanone (1.0 g) in anhydrous tetrahydrofuran (15 ml) was added over 0.1 hr. After stirring at room temperature for 16 hr, the reaction mixture was partitioned between saturated ammonium acetate solution (150 ml) and ethyl acetate (150 ml). The layers were separated and the aqueous layer was extracted with ethyl acetate (4×50 ml). The combined organic extracts were washed with brine (50 ml), dried over magnesium sulfate and concentrated in vacuo. The residue was purified by flash column chromatography to give the title as a white solid (316 mg, 30%). $\delta_H$ (CD$_3$OD) 1.20–1.40 (2H, m), 1.60–2.10 (6H, m), 2.66 (1.4H, s), 2.69 (0.6H, s), 2.75–2.95 (1H, m), 6.20–6.27 (2H, m), 6.90 (0.7H, d), 6.91 (0.3H, d); m/z (ES$^-$) 219 (M–H$^-$).

Example 20

4-(4-Methylenecyclohexyl)-1,3-benzenediol

To a round bottomed flask was added tert-butyl[5-{[tert-butyl(dimethyl)silyl]oxy}-2-(4-methylenecyclohexyl) phenoxy]dimethylsilane (40 mg), tetrahydrofuran (2 ml) and tetrabutylammonium fluoride (281 μl, 1.0M in tetrahydrofuran), and the mixture stirred at room temperature for 15 hr. The solvent was removed in vacuo and the residue partitioned between water (20 ml) and ethyl acetate (20 ml). The aqueous phase was extracted with ethyl acetate (2×20 ml), and the combined organic phases were washed with brine (20 ml), dried over magnesium sulfate, filtered and concentrated in vacuo. Purification via flash chromatography (SiO$_2$, ethyl acetate/petroleum ether 2:3 v/v) furnished the title compound (17 mg, 90%) as a white solid. $\delta_H$ (CD$_3$OD): 1.42–1.53 (2H, m), 1.90–1.99 (2H, m), 2.19–2.29 (2H, m), 2.39–2.47 (2H, m), 3.02 (1H, tt), 4.67 (2H, s), 6.28 (1H, dd), 6.31 (1H, d), 6.89 (1H, d); m/z (ES$^+$) 205 (M+H)$^+$.

Example 21

4-(3-Cyclohexen-1-yl)-1,3-benzenediol

To a round bottomed flask was added cis/trans-4-(2,4-bis{[tert-butyl(dimethyl)silyl]oxy}phenyl)cyclohexanol (208 mg) and dichloromethane (3 ml). The resulting solution was cooled to –78° C., and diethylaminosulfur trifluoride (69 μl) added in one portion. The reaction mixture was allowed to warm to room temperature and stirred for 15 hr. The reaction mixture was partitioned between water (10 ml) and dichloromethane (20 ml), the layers were separated and the aqueous phase was extracted with dichloromethane (3×20 ml). The combined organic phases were washed with brine (20 ml), dried over magnesium sulfate, filtered and concentrated in vacuo. The crude oil was dissolved in tetrahydrofuran (3 ml) and tetrabutylammonium fluoride (0.81 ml, 1.0M in tetrahydrofuran) and stirred at room temperature for 15 hr. The reaction mixture was partitioned between water (10 ml) and ethyl acetate (20 ml) and the layers were separated. The aqueous phase was extracted with ethyl acetate (3×20 ml) and the combined organic phases were washed with brine (10 ml), dried over magnesium sulfate, filtered and concentrated in vacuo. Purification via flash chromatography (SiO$_2$, ethyl acetate/petroleum ether, 3:7 v/v) furnished the title compound (34 mg, 38%) as an off-white solid. $\delta_H$ (CD$_3$OD): 1.69–1.86 (2H, m), 2.00–2.19 (4H, m), 3.09 (1H, tt), 5.67–5.80 (2H, m), 6.16 (1H, d), 6.20 (1H, dd), 6.91 (1H, d); m/z (ES$^-$) 189 (M–H)$^+$.

Example 22 trans-4-(2,4-Dihydroxyphenyl)cyclohexyl (2R)-2-amino-3-phenylpropanoate

To a round bottomed flask was added trans-4-(2,4-bis{[tert-butyl(dimethyl)silyl]oxy}phenyl) cyclohexyl (2R)-2-[(tert-butoxycarbonyl)amino]-3-phenyl propanoate (250 mg), dichloromethane (10 ml), trifluoroacetic acid (4 ml) and water (0.5 ml). After stirring at room temperature for 15 hr, saturated sodium hydrogen carbonate solution (5 ml) was added, followed by water (10 ml) and ethyl acetate (30 ml). The layers were separated and the aqueous layer was extracted with ethyl acetate (2×30 ml), and the combined organic phases were washed with brine (15 ml), dried over magnesium sulfate, filtered and concentrated in vacuo. Purification via flash chromatography (SiO$_2$, ethyl acetate/ammonia, 99:1 v/v) furnished the title compound (93 mg, 72%) as an off-white solid. $\delta_H$ (CD$_3$OD): 1.45–1.66 (4H, m), 1.85–2.15 (4H, m), 2.76–2.88 (1H, m), 3.23 (2H, d), 3.97 (1H, t), 4.84–5.00 (1H, m), 6.27 (1H, dd), 6.32 (1H, d), 6.92 (1H, d), 7.28–7.45 (5H, m); m/z (ES$^+$) 356 (M+H)$^+$.

Example 23

Benzyl [4-(2,4-dihydroxyphenyl)cyclohexylidene] acetate

To a round bottomed flask equipped with magnetic stirrer was added benzyl [4-(2,4-bis{[tert-butyl(dimethyl)silyl]

oxy}phenyl)cyclohexylidene]acetate (232 mg), tetrahydrofuran (5 ml), tetrabutylammonium fluoride hydrate (429 mg) and glacial acetic acid (94 µl). After stirring at room temperature for 0.5 hr, the solvent was removed in vacuo and the residue partitioned between ethyl acetate (100 ml) and water (20 ml). The layers were separated and the aqueous phase was extracted with ethyl acetate (50 ml). The combined organic phases were washed with water (50 ml), brine (20 ml), dried over magnesium sulfate, filtered and concentrated in vacuo. Purification via flash chromatography (SiO$_2$, ethyl acetate/petroleum ether, 1:3 v/v) furnished the title compound (100 mg, 72%) as a cream solid. $\delta_H$ (CD$_3$OD): 1.59–1.67 (2H, m), 1.98–2.13 (4H, m), 2.37–2.48 (2H, m), 3.14 (1H, ft), 5.16 (2H, s), 5.75 (1H, s), 6.26 (1H, dd), 6.30 (1H, d), 6.89 (1H, d), 7.30–7.44 (5H, m); m/z (ES$^+$) 337 (M–H)$^-$.

Example 24

4-(1,4-Dithiaspiro[4.5]dec-8-yl)-1,3-benzenediol

To a round bottomed flask equipped with magnetic stirrer was added 4-(2,4-dihydroxyphenyl)cyclohexanone (1 g) and toluene (40 ml). To the stirred solution was added ethane-1,2-dithiol (0.49 ml) and a few crystals of ptoluenesulfonic acid monohydrate and the reaction mixture was heated under reflux for 3.5 hr. The reaction mixture was cooled to room temperature, saturated sodium hydrogencarbonate solution (20 ml) was added, and the layers were separated. The aqueous layer was diluted with water (40 ml) and extracted into ethyl acetate (3×30 ml). The combined organic phases were washed with brine (30 ml), dried over magnesium sulfate, filtered and concentrated in vacuo. Purification via flash chromatography (SiO$_2$, ethyl acetate/petroleum ether 2:3 v/v) furnished the title compound (1.34 g, 98%) as a white solid. $\delta_H$ (CD$_3$OD): 1.59–1.73 (2H, m), 1.75–1.84 (2H, m), 1.98–2.08 (2H, m), 2.14–2.22 (2H, m), 2.77 (1H, tt), 3.22–3.32 (4H, m), 6.18–6.24 (2H, m), 6.85 (1H, d); m/z (ES$^+$) 283 (M+H)$^+$.

Example 25

N'-[4-(2,4-Dihydroxyphenyl)cyclohexylidene]-4-methylbenzenesulfonohydrazide To a round bottomed flask was added N'-[4-(2,4-bis{[tert-butyl(dimethyl)silyl]oxy}phenyl)cyclohexylidene-4-methylbenzenesulfonohydrazide (100 mg), tetrahydrofuran (5 ml), glacial acetic acid (3 drops) and tetrabutylammonium fluoride hydrate (174 mg), and the resulting solution was stirred at room temperature for 2 hr. Saturated sodium hydrogen carbonate solution (10 ml) was added and stirring was continued for 1 hr. The reaction mixture was partitioned between water (10 ml) and ethyl acetate (20 ml), the layers were separated, and the aqueous phase was extracted with ethyl acetate (2×20 ml). The combined organic phases were washed with brine (10 ml), dried over magnesium sulfate, filtered and concentrated in vacuo. Purification via flash chromatography (SiO$_2$, ethyl acetate/petroleum ether, 7:3 v/v) furnished the title compound (62 mg, 100%) as a cream solid. $\delta_H$ ((CD$_3$)$_2$CO): 1.44–1.63 (2H, m), 1.92–2.01 (3H, m), 2.22–2.32 (1H, m), 2.35–2.43 (2H, m), 2.97 (3H, s), 3.09 (1H, tt), 6.28 (H, dd), 6.37 (1H, d), 6.87(1H, d), 7.38 (2H, d), 7.79 (2H, d), 7.96 (1H, s), 8.13 (1H, s), 8.99 (1H, s); m/z (ES$^+$) 375 (M+H)$^+$.

Example 26 trans-N-[4(2,4-Dihydroxyphenyl)cyclohexyl]-3-nitrobenzamide

To a round bottomed flask was added trans-N-[4-(2,4-bis{[tert-butyl(dimethyl)silyl]oxy})cyclohexyl]-3-nitrobenzamide (52 mg), dichloroethane (9 ml), water (3 ml), and trifluoroacetic acid (3 ml). The reaction mixture was heated under reflux for 15 hr, cooled to room temperature, and toluene (15 ml) was added. The reaction mixture was concentrated in vacuo, methanol (15 ml) was added, and further concentrated to remove residual trifluoroacetic acid. Purification via flash chromatography (SiO$_2$, ethyl acetate/petroleum ether, gradient elution using 1:3, then 1:1, v/v) furnished the title compound (20 mg, 63%) as a white solid. $\delta_H$ ((CD$_3$)$_2$CO): 1.52–1.68 (4H, m), 1.87–1.95 (2H, m), 2.09–2.17 (2H, m), 2.87 (1H, tt), 3.97–4.08 (1H, m), 6.30 (1H, dd), 6.38 (1H, d), 6.99 (1H, d), 7.77 (1H, t), 7.90 (1H, s), 7.96 (1H, d), 8.05 (1H, s), 8.33 (1H, dd), 8.37 (1H, dd), 8.68 (1H, t); m/z (ES$^+$) 357 (M+H)$^+$.

Example 27 trans-N-[4-(2,4-dihydroxyphenyl)cyclohexyl]-N'-phenylurea

To a round bottomed flask was added trans-4-(2,4-bis{[tert-butyl(dimethyl)silyl]oxy}phenyl)cyclohexylamine (750 µl, 0.114M in dichloromethane) and dichloroethane (3.5 ml). To the stirred solution was added phenylisocyanate (15 µl), triethylamine (30 µl) and a few crystals of 4-dimethylaminopyridine, and the resulting solution was stirred at room temperature for 15 hr. The mixture was partitioned between water (5 ml) and dichloromethane (5 ml), the layers separated, and the aqueous phase extracted with dichloromethane (2×5 ml). The combined organic phases were washed with brine (7 ml), dried over magnesium sulfate, filtered and concentrated in vacuo to give a brown gum (57 mg). The residue was dissolved in dichloromethane (6 ml), methanol (3 ml), trifluoroacetic acid (3 ml) and water (3 ml), and the resulting solution was stirred at room temperature for 96 hr. Residual trifluoroacetic acid was removed by co-evaporation with toluene (15 ml), then methanol (15 ml), in vacuo. Purification via flash chromatography (SiO$_2$, ethyl acetate/petroleum ether, gradient elution using 1:4, 2:3, then 3:2 v/v) furnished the title compound (10 mg, 31%) as a white solid. $\delta_H$ (CD$_3$OD): 1.44–1.64 (4H, m), 1.88–1.96 (2H, m), 2.08–2.16 (2H, m), 2.86 (1H, tt), 3.47–3.58 (1H, m), 6.27 (1H, dd), 6.30 (1H, d), 6.93 (1H, d), 7.13 (2H, d), 7.23 (1H, t), 7.41 (2H, t); m/z (ES$^+$) 327 (M+H)$^+$.

Example 28 trans-N-[4-(dihydroxyphenyl)cyclohexyl]-2,2,2-trifluoroacetamide

To a round bottomed flask equipped was added trans-4-(2,4-bis{[tert-butyl(dimethyl)silyl]oxy}phenyl) cyclohexylamine (56 mg) and dichloroethane (5 ml). To the stirred solution were added trifluoroacetic anhydride (60 µl), triethylamine (40 µl) and a 4-dimethylaminopyridine (catalytic), and the resulting solution was heated to 50° C. for 15 hr. The reaction mixture was partitioned between aqueous sodium hydroxide (10 ml, 0.5M) and dichloromethane (10 ml), the layers separated, and the aqueous phase extracted with dichloromethane (2×10 ml). The combined organic phases were washed with brine (10 ml), dried over magnesium sulfate, filtered and concentrated in vacuo to give a gum. The residue was dissolved in dichloroethane (9 ml), trifluoroacetic acid (3 ml) and water (3 ml), and the resulting solution was heated under reflux for 15 hr. The reaction mixture was cooled to room temperature and the residual trifluoroacetic acid removed by co-evaporation with toluene (10 ml), then methanol (10 ml), in vacuo. Purification via flash chromatography (SiO$_2$, ethyl acetate/petroleum ether, gradient elution using 2:1 then 1:1 v/v) furnished the title compound (12 mg, 31%) as a white solid.

$\delta_H$ ((CD$_3$)$_2$CO): 1.49–1.66 (4H, m), 1.85–1.93 (2H, m), 1.98–2.07 (2H, m), 2.78–2.89 (1H, m), 3.78–3.90 (1H, m), 6.29 (1H, dd), 6.37 (1H, d), 6.95 (1H, d), 7.91 (1H, s), 8.06 (1H, s), 8.18 (1H, br s); m/z (ES$^-$) 302 (M–H)$^-$.

Example 29 cis-3-cyano-N-[4-(2,4-dihydroxyphenyl) cyclohexyl]-N-hydroxybenzamide

General Procedure B cis-N-Benzoyloxy-N-[2,4-bis{[tert-butyl(dimethyl)silyl]oxy}phenyl)cyclohexyl]-3-cyanobenzamide (20 mg) was dissolved in methanol (2 ml) and stirred rapidly with Amberlyst A-26 (fluoride resin) (0.1 g) for 24 hr. The mixture was filtered through a pad of celite and concentrated in vacuo. This residue was dissolved in ethanol (2 ml) and sodium hydroxide (2M, 0.2 ml) added with stirring. After stirring for 15 min, the solution was acidified with 2M HCl, diluted with water (2 ml) and extracted with ethyl acetate (3×5 ml). The combined organic extracts were washed with brine (5 ml), dried over magnesium sulfate, filtered and concentrated in vacuo. Purification via flash chromatography (SiO$_2$, ethyl acetate/petroleum ether, 2:1, v/v) afforded the title compound (0.004 g, 39%) as a colourless solid; $\delta_H$ (CD$_3$OH) 1.68–1.84 (4H, m), 2.03–2.17 (4H, m), 3.03 (1H, m), 4.52 (1H, m), 6.24 (2H, m), 7.03 (1H, d), 7.61 (1H, t), 7.80 (1H, m), 7.91 (1H, m) and 7.97 (1H, m). m/z (ES$^-$) 351 (M–H)$^-$, 397 ((M+HCO$_2$H)–1).

Example 30 cis-N-[4-(2,4-dihydroxyphenyl)cyclohexyl]-N-hydroxy-4-(trifluoromethyl)benzamide Example 30 was prepared according to General Procedure B above from cis-N-benzoyloxy-N-[2,4-bis{[tert-butyl(dimethyl)silyl]oxy}phenyl)cyclohexyl]-4(trifluoro methyl)benzamide (0.058 g) to give the title compound (0.017 g, 54%) as a colourless solid. $\delta_H$ (CD$_3$OH) 1.70–1.82 (4H, m), 2.01–2.18 (4H, m), 3.03 (1H, m), 4.47 (1H, m), 6.22 (2H, m), 7.02 (1H, d), and 7.71–7.80 (4H, m). m/z (ES$^+$) 396 (M+H)$^+$.

Example 31 cis-N-[4-(2,4-dihydroxyphenyl)cyclohexyl]-N-hydroxy-4-methoxybenzamide

Example 31 was prepared according to General Procedure B above from cis —N-benzoyloxy-N[2,4-bis{[tert-butyl(dimethyl)silyl]oxy}phenyl)cyclohexyl]methoxybenzamide (0.033 mg) to give the title compound (12 mg, 70%) as a colourless solid. $\delta_H$ (CD$_3$OH) 1.68–1.80 (4H, m), 2.00–2.19 (4H, m), 3.02 (1H, m), 3.83 (3H, s), 4.42 (1H, m), 6.25 (2H, m), 6.97 (2H, d), 7.03 (1H, d), and 7.62 (2H, d). m/z (ES$^+$) 358 (M+H)$^+$.

Example 32

(±)-Methyl[4-(2,4-dihydroxyphenyl) cyclohexylidene] acetate

To a stirred solution of methyl[4-(2,4-bis{[tert-butyl(dimethyl)silyl]oxy}phenyl) cyclohexylidene]acetate (0.035 g) in THF (10 ml) was added tetrabutylammonium fluoride (0.14 ml). After 45 min, the mixture was poured into saturated sodium carbonate solution (20 ml) and extracted with ethyl acetate (3×20 ml). The combined organic extracts were washed with brine (10 ml), dried over magnesium sulfate, filtered and concentrated in vacuo. Purification via flash chromatography (SiO$_2$, ethyl acetate/petroleum ether, 1:1, v/v) afforded the title compound (0.015 g, 80%) as a white solid. oil. $\delta_H$ (CD$_3$OH) 1.50–1.68 (2H, m), 1.98–2.13 (4H, m), 2.38–2.46 (2H, m), 3.14 (1H, m), 3.72 (3H, s), 5.72 (1H, s), 6.36 (1H, dd), 6.30 (1H, d) and 6.90 (1H, d). m/z (ES$^-$) 261 (M–H)$^-$.

Additional compounds (Examples 33–65) have also been prepared (Table 1, below). These compounds fall within the scope of the present invention, are useful in the pharmaceutical compositions and methods of the present invention, and can be prepared using the above-described synthetic processes in conjunction with standard techniques.

TABLE 1

| Example | Structure | Information |
|---|---|---|
| 33 | 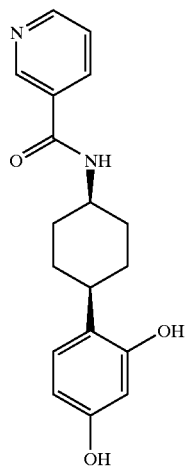 | m/z (ES+); 313 (M + H)$^+$<br>RT = 2.01 min. |

TABLE 1-continued

| Example | Structure | Information |
|---|---|---|
| 34 | 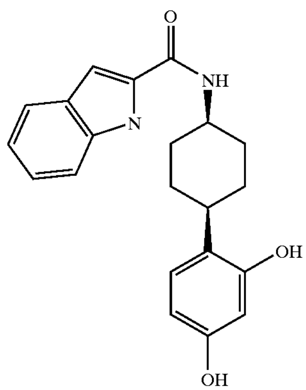 | m/z (ES−); 349 (M − H)−<br>RT = 2.72 min. |
| 35 | 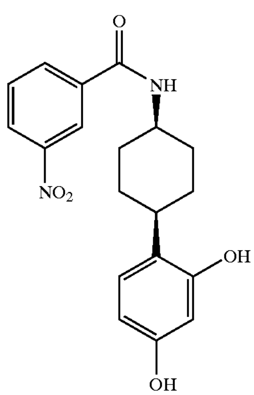 | m/z (ES+); 435 (M + H + DMSO)+<br>RT = 2.65 min. |
| 36 | 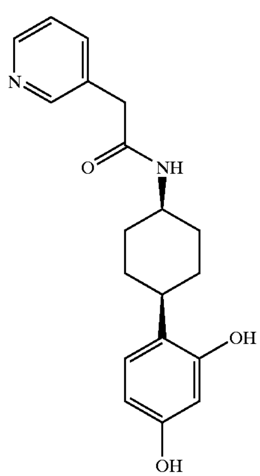 | m/z (ES+); 405 (M + H + DMSO)+<br>RT = 1.70 min. |

TABLE 1-continued

| Example | Structure | Information |
|---|---|---|
| 37 | 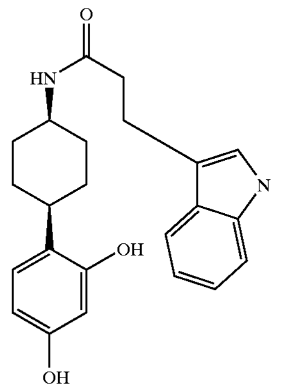 | m/z (ES+); 457 (M + H + DMSO)+<br>RT = 2.55 min. |
| 38 | 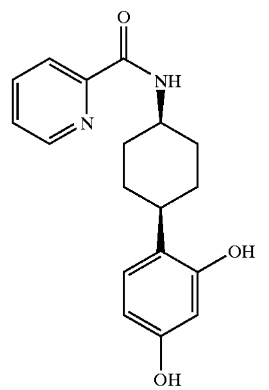 | m/z (ES+); 391 (M + H + DMSO)+<br>RT = 2.46 min. |
| 39 | 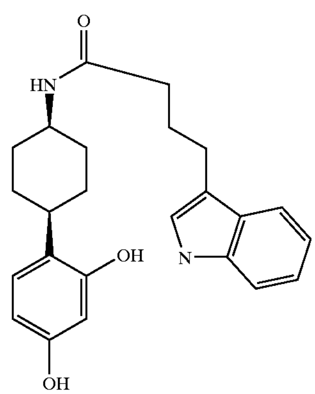 | m/z (ES+); 392 (M + H + DMSO)+<br>RT = 2.73 min. |
| 40 | 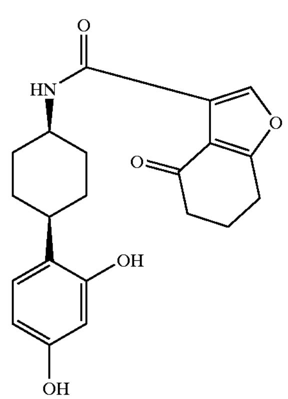 | m/z (ES+); 448 (M + H + DMSO)+<br>RT = 2.51 min. |

TABLE 1-continued
| Example | Structure | Information |
|---|---|---|
| 41 | 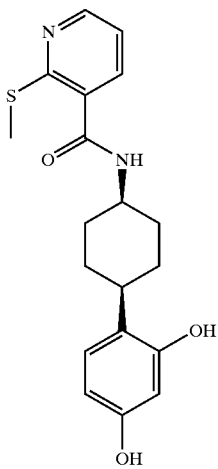 | m/z (ES+); 437 (M + H + DMSO)⁺<br>RT = 2.45 min. |
| 42 | 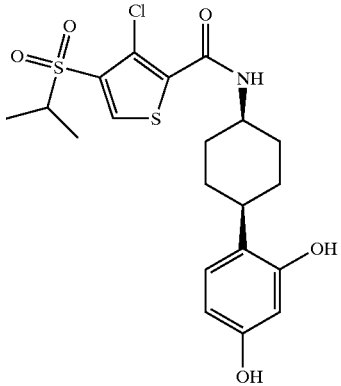 | m/z (ES−); 456(M − H)⁻<br>RT = 2.70 min. |
| 43 | 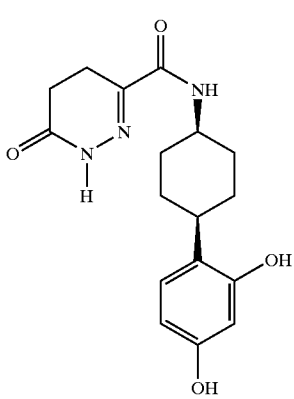 | m/z (ES−); 330 (M − H)⁻<br>RT = 2.15 min. |

TABLE 1-continued

| Example | Structure | Information |
|---|---|---|
| 44 | 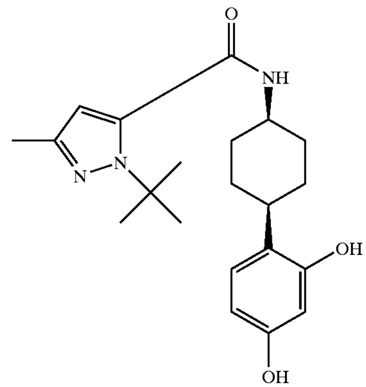 | m/z (ES−); 370 (M − H)−<br>RT = 2.60 min. |
| 45 | 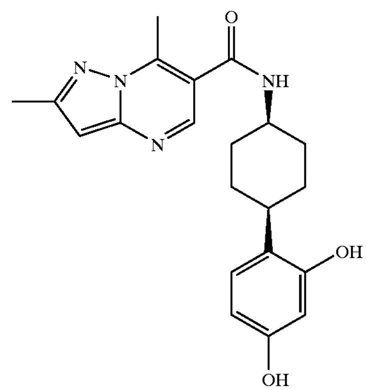 | m/z (ES−); 379 (M − H)−<br>RT = 2.37 min. |
| 46 | 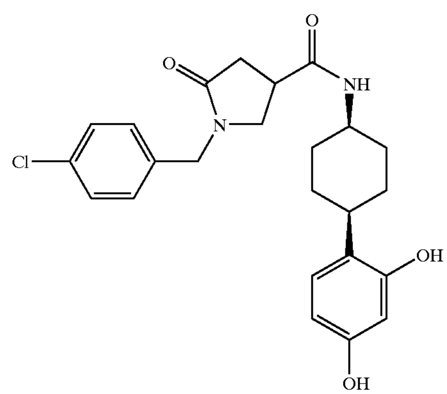 | m/z (ES−); 441 (M − H)−<br>RT = 2.61 min. |
| 47 | 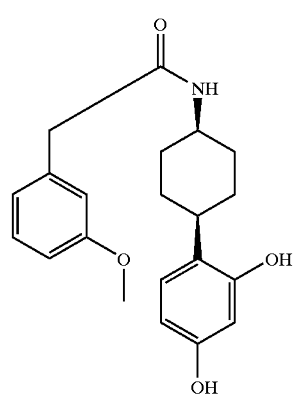 | m/z (ES+); 434 (M + H + DMSO)+<br>Rt = 2.45 min. |

TABLE 1-continued

| Example | Structure | Information |
|---|---|---|
| 48 | [structure: 2-(4-methoxyphenyl)-N-(trans-4-(2,4-dihydroxyphenyl)cyclohexyl)acetamide] | m/z (ES+); 434 (M + H + DMSO)+<br>RT = 2.43 min. |
| 49 | [structure: 2-cyclohexyl-N-(trans-4-(2,4-dihydroxyphenyl)cyclohexyl)acetamide] | m/z (ES+); 410 (M + H + DMSO)+<br>RT = 2.63 min. |
| 50 | [structure: 2-(2-methylphenyl)-N-(trans-4-(2,4-dihydroxyphenyl)cyclohexyl)acetamide] | m/z (ES+); 418 (M + H + DMSO)+<br>RT = 2.54 min. |

TABLE 1-continued

| Example | Structure | Information |
|---|---|---|
| 51 | (2-methylbenzamide of trans-4-(2,4-dihydroxyphenyl)cyclohexylamine) | m/z (ES+); 404 (M + H + DMSO)+<br>RT = 2.55 min. |
| 52 | (4-bromobenzamide of trans-4-(2,4-dihydroxyphenyl)cyclohexylamine) | m/z (ES−); 388 (M − H)−;<br>390 (M − H)−<br>RT = 2.77 min. |
| 53 | (tetrahydrofuran-2-carboxamide of trans-4-(2,4-dihydroxyphenyl)cyclohexylamine) | m/z (ES−); 392 (M − H)−<br>RT = 2.98 min. |
| 54 | (adamantane-1-carboxamide of trans-4-(2,4-dihydroxyphenyl)cyclohexylamine) | m/z (ES−); 368 (M − H)−<br>RT = 2.90 min. |

TABLE 1-continued

| Example | Structure | Information |
|---|---|---|
| 55 | [structure: 4-bromo-3-methyl-1-ethyl-pyrazole-5-carboxamide linked via NH to trans-cyclohexyl-(2,4-dihydroxyphenyl)] | m/z (ES+); 500 (M + H + DMSO)+; 502 (M + H + DMSO)+ RT = 2.66 min. |
| 56 | [structure: 4-nitrobenzamide linked via NH to trans-cyclohexyl-(2,4-dihydroxyphenyl)] | m/z (ES−); 355 (M − H)− RT = 2.62 min. |
| 57 | [structure: cyclohex-1-ene-1-carboxamide linked via NH to trans-cyclohexyl-(2,4-dihydroxyphenyl)] | m/z (ES+); 394 (M + H + DMSO)+ RT = 2.57 min. |

TABLE 1-continued
| Example | Structure | Information |
|---------|-----------|-------------|
| 58 | 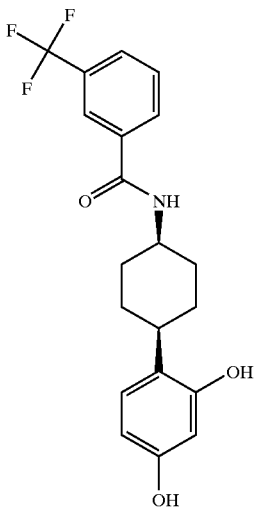 | m/z (ES−); 378 (M − H)⁻<br>RT = 2.81 min. |
| 59 | 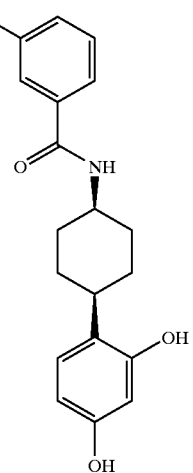 | m/z (ES−); 381 (M + HCO$_2$)⁻<br>RT = 2.52 min. |
| 60 | 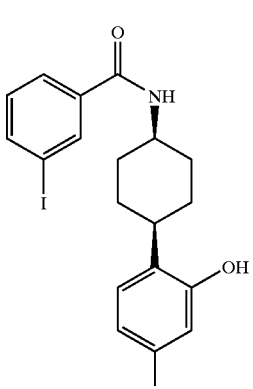 | m/z (ES−); 436 (M − H)⁻<br>RT = 2.80 min. |

TABLE 1-continued

| Example | Structure | Information |
|---|---|---|
| 61 | (2-bromobenzamide of trans-4-(2,4-dihydroxyphenyl)cyclohexylamine) | m/z (ES+); 468 (M + H + DMSO)+; 470 (M + H + DMSO)+ <br> RT = 2.54 min. |
| 62 | (3-bromobenzamide of trans-4-(2,4-dihydroxyphenyl)cyclohexylamine) | m/z (ES+); 468 (M + H + DMSO)+; 470 (M + H + DMSO)+ <br> RT = 2.75 min. |
| 63 | (4-bromo-2-chlorobenzamide of trans-4-(2,4-dihydroxyphenyl)cyclohexylamine) | m/z (ES−); 422 (M − H); 424 (M − H)− <br> RT = 2.77 min. |
| 64 | (N-Boc-prolinamide of trans-4-(2,4-dihydroxyphenyl)cyclohexylamine) | m/z (ES+); 405 (M + H)+ <br> RT = 2.51 min. |

TABLE 1-continued

| Example | Structure | Information |
|---|---|---|
| 65 | 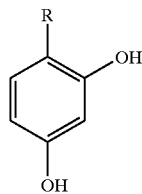 | m/z (ES−); 454 (M − H)−<br>RT = 2.61 min. |

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

What is claimed is:

1. A cosmetic composition comprising a cosmetically acceptable topical carrier in combination with an effective amount of a compound of formula I

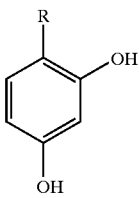

or a pharmaceutically acceptable salt thereof, wherein:
R is a $(C_3-C_8)$cycloalkyl or $(C_5-C_8)$cycloalkenyl ring substituted by —N($R^1$)CONR$^2R^3$ wherein $R^1$ and $R^2$ are independently selected from hydrogen, $(C_1-C_6)$ alkyl, and aryl$(C_1-C_6)$alkyl, and $R^3$ is hydrogen, $(C_1-C_6)$alkyl-, aryl$(C_1-C_6)$alkyl, or aryl; —N($R^4$) COR$^5$ wherein $R^4$ is hydrogen, $(C_1-C_6)$alkyl, aryl $(C_1-C_6)$alkyl-, or OH and $R^5$ is $(C_7-C_{10})$alkyl, aryl, aryl$(C_1-C_6)$alkyl-, —Oaryl, $CF_3$, heterocycloalkyl, —$(C_1-C_6)$alkylheterocycloalkyl, —$(C_2-C_7)$ alkenylheterocycloalkyl, heteroaryl, —$(C_1-C_6)$ alkylheteroaryl, —$(C_2-C_7)$alkenylheteroaryl, —$(C_2-C_7)$alkenlaryl, —$(C_2-C_7)$alkenylCOaryl, —$(C_1-C_6)$alkylN($R^4$)CO-aryl, —$(C_1-C_6)$alkylCO-aryl, —$(C_1-C_6)$alkylhydroxyaryl, —$(C_1-C_6)$alkyl-X-aryl, $(C_2-C_7)$alkenyl, benzyhydryl, 5-hydroxyoxoindanyl, or tetrahydronaphthanenyl, wherein X is O, S, SO, $SO_2$ or NR$^1$; —N($R^1$) OCOaryl; =CHCO$_2R^1$; =CHCONR$^1R^2$; =CHCN; =NNHSO$_2R^6$ wherein $R^6$ is aryl; —N(O)=CHR$^6$; —OC(O)NR$^1R^7$ wherein $R^7$ is aryl, aryl$(C_1-C_6)$alkyl-, —$(C_1-C_6)$alkylCO$_2(C_1-C_6)$alkyl, —CO$_2(C_1-C_6)$ alkyl, —CO$_2$aryl, or —CO$_2(C_1-C_6)$alkylaryl; amino $(C_1-C_6)$alkylarylCO$_2$—; or —OC(O)OR$^8$ wherein $R^8$ is $(C_1-C_6)$alkyl, aryl$(C_1-C_6)$alkyl, or aryl;

with the proviso that the cycloalkenyl ring is not aromatic.

2. A method for inhibiting tyrosinase in a human comprising administering to said human an effective amount of compound of formula I.

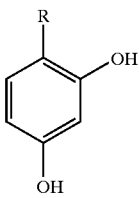

or a pharmaceutically acceptable salt thereof, wherein:
R is a $(C_3-C_8)$cycloalkyl or $(C_5-C_8)$cycloalkenyl ring substituted by —N($R^1$)CONR$^2R^3$ wherein $R^1$ and $R^2$ are independently selected from hydrogen, $(C_1-C_6)$ alkyl, and aryl$(C_1-C_6)$alkyl, and $R^3$ is hydrogen, $(C_1-C_6)$alkyl-, aryl$(C_1-C_6)$alkyl, or aryl; —N($R^4$) COR$^5$ wherein $R^4$ is hydrogen, $(C_1-C_6)$alkyl, aryl $(C_1-C_6)$alkyl-, or OH and $R^5$ is $(C_7-C_{10})$alkyl, aryl, aryl$(C_1-C_6)$alkyl-, —Oaryl, $CF_3$, heterocycloalkyl, —$(C_1-C_6)$alkylheterocycloalkyl, —$(C_2-C_7)$ alkenylheterocycloalkyl, heteroaryl, —$(C_1-C_6)$ alkylheteroaryl, —$(C_2-C_7)$alkenylheteroaryl, —$(C_2-C_7)$alkenlaryl, —$(C_2-C_7)$alkenylCOaryl, —$(C_1-C_6)$alkylN($R^4$)CO-aryl, —$(C_1-C_6)$alkylCO-aryl, —$(C_1-C_6)$alkylhydroxyaryl, —$(C_1-C_6)$alkyl-X-aryl, $(C_2-C_7)$alkenyl, benzyhydryl, 5-hydroxyoxoindanyl, or tetrahydronaphthanenyl, wherein X is O, S, SO, $SO_2$ or NR$^1$; —N($R^1$) OCOaryl; =CHCO$_2R^1$; =CHCONR$^1R^2$; =CHCN; =NNHSO$_2R^6$ wherein $R^6$ is aryl; —N(O)=CHR$^6$; —OC(O)NR$^1R^7$ wherein $R^7$ is aryl, aryl$(C_1-C_6)$alkyl-, —$(C_1-C_6)$alkylCO$_2(C_1-6)$alkyl, —$C_2(C_1-C_6)$alkyl, —COO$_2$aryl, or —CO$_2(C_1-C_6)$alkylaryl; amino $(C_1-C_6)$alkylarylCO$_2$—; or —OC(O)OR$^8$ wherein $R^8$ is $(C_1-C_6)$alkyl, aryl$(C_1-C_6)$alkyl, or aryl;

with the proviso that the cycloalkenyl ring is not aromatic.

3. A method for treating a human afflicted with an inflammatory disorder selected from the group consisting of psoriasis, dermatitis, acne and dandruff comprising topically administering to said human a compound of formula I

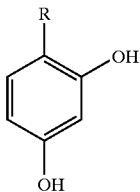

or a pharmaceutically acceptable salt thereof, wherein:

R is a ($C_3$–$C_8$)cycloalkyl or ($C_5$–$C_8$)cycloalkenyl ring substituted by —N($R^1$)CONR$^2$R$^3$ wherein $R^1$ and $R^2$ are independently selected from hydrogen, ($C_1$–$C_6$) alkyl, and aryl($C_1$–$C_6$)alkyl, and $R_3$ is hydrogen, ($C_1$–$C_6$)alkyl-, aryl($C_1$–$C_6$)alkyl, or aryl; —N($R^4$) COR$^5$ wherein $R^4$ is hydrogen, ($C_1$–$C_6$)alkyl, aryl ($C_1$–$C_6$)alkyl-, or OH and $R^5$ is ($C_7$–$C_{10}$)alkyl, aryl, aryl($C_1$–$C_6$)alkyl-, —Oaryl, $CF_3$, heterocycloalkyl, —($C_1$–$C_6$)alkylheterocycloalkyl, —($C_2$–$C_7$) alkenylheterocycloalkyl, heteroaryl, —($C_1$–$C_6$) alkylheteroaryl, —($C_2$–$C_7$)alkenylheteroaryl, —($C_2$–$C_7$)alkenlaryl, —($C_2$–$C_7$)alkenylCOaryl, —($C_1$–$C_6$)alkylN($R^4$)CO-aryl, —($C_1$–$C_6$)alkylCO-aryl, —($C_1$–$C_6$)alkylhydroxyaryl, —($C_1$–$C_6$)alkyl-X-aryl, ($C_2$–$C_7$)alkenyl, benzyhydryl, 5-hydroxyoxoindanyl, or tetrahydronaphthanenyl, wherein X is O, S, SO, $SO_2$ or NR$^1$; —N($R^1$) OCOaryl; =CHCO$_2$R$^1$; CHCONR$^1$R$^2$; =CHCN; =NNHSO$_2$R$^6$ wherein R$^6$ is aryl; —N(O)=CHR$^6$; —OC(O)NR$^1$R$^7$ wherein R$^7$ is aryl, aryl($C_1$–$C_6$)alkyl-, —($C_1$–$C_6$) alkylCO$_2$($C_1$–$C_6$)alkyl, —CO$_2$($C_1$–$C_6$)alkyl, —CO$_2$aryl, or —CO$_2$($C_1$–$C_6$)alkylaryl; amino($C_1$–$C_6$) alkylarylCO$_2$—; or —OC(O)R$^8$ wherein R$^8$ is ($C_1$–$C_6$) alkyl, aryl($C_1$–$C_6$)alkyl, or aryl;

with the proviso that the cycloalkenyl ring is not aromatic.

4. A method for the treatment of disorders of human pigmentation comprising topically administering to said human an effective amount of a compound of formula I.

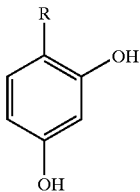

or a pharmaceutically acceptable salt thereof, wherein:

R is a ($C_3$–$C_8$)cycloalkyl or ($C_5$–$C_8$)cycloalkenyl ring substituted by —N($R^1$)CONR$^2$R$^3$ wherein $R^1$ and $R^2$ are independently selected from hydrogen, ($C_1$–$C_6$) alkyl, and aryl($C_1$–$C_6$)alkyl, and $R^3$ is hydrogen, ($C_1$–$C_6$)alkyl-, aryl($C_1$–$C_6$)alkyl, or aryl; —N($R^4$) COR$^5$ wherein $R^4$ is hydrogen, ($C_1$–$C_6$)alkyl, aryl ($C_1$–$C_6$)alkyl-, or OH and $R^5$ is ($C_7$–$C_{10}$)alkyl, aryl, aryl($C_1$–$C_6$)alkyl-, —Oaryl, $CF_3$, heterocycloalkyl, —($C_1$–$C_6$)alkylheterocycloalkyl, —($C_2$–$C_7$) alkenylheterocycloalkyl, heteroaryl, —($C_1$–$C_6$) alkylheteroaryl, —($C_2$–$C_7$)alkenylheteroaryl, —($C_2$–$C_7$)alkenlaryl, —($C_2$–$C_7$)alkenylCOaryl, —($C_1$–$C_6$)alkylN($R^4$)CO-aryl, —($C_1$–$C_6$)alkylCO-aryl, —($C_1$–$C_6$)alkylhydroxyaryl, —($C_1$–$C_6$)alkyl-X-aryl, ($C_2$–$C_7$)alkenyl, benzyhydryl, 5-hydroxyoxoindanyl, or tetrahydronaphthanenyl, wherein X is O, S, SO, $SO_2$ or NR$^1$; —N($R^1$) OCOaryl; =CHCO$_2$R$^1$; =CHCONR$^1$R$^2$; =CHCN; =NNHSO$_2$R$^6$ wherein R$^6$ is aryl; —N(O)=CHR$^6$; —OC(O)NR$^1$R$^7$ wherein R$^7$ is aryl, aryl($C_1$–$C_6$)alkyl-, —($C_1$–$C_6$)alkylCO$_2$($C_1$–$C_6$)alkyl, —CO$_2$($C_1$–$C_6$) alkyl, —CO$_2$aryl, or —CO$_2$($C_1$–$C_6$)alkylaryl; amino ($C_1$–$C_6$)alkylarylCO$_2$—; or —OC(O)OR$^8$ wherein R$^8$ is ($C_1$–$C_6$)alkyl, aryl($C_1$–$C_6$)alkyl, or aryl;

with the proviso that the cycloalkenyl ring is not aromatic.

5. A method according to claim 4 in which said disorder is selected from the group consisting of solar lentigines and simple lentigines.

6. A method for cosmetically lightening skin comprising topically administering to a human in need of such an effect a cosmetically effective amount of a compound according to formula I

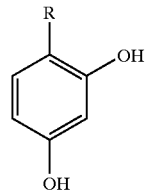

or a pharmaceutically acceptable salt thereof, wherein:

R is a ($C_3$–$C_8$)cycloalkyl or ($C_5$–$C_8$)cycloalkenyl ring substituted by —N($R^1$)CONR$^2$R$^3$ wherein $R^1$ and $R^2$ are independently selected from hydrogen, ($C_1$–$C_6$) alkyl, and aryl($C_1$–$C_6$)alkyl, and $R^3$ is hydrogen, ($C_1$–$C_6$)alkyl-, aryl($C_1$–$C_6$)alkyl, or aryl; —N($R^4$) COR$^5$ wherein $R^4$ is hydrogen, ($C_1$–$C_6$)alkyl, aryl ($C_1$–$C_6$)alkyl-, or OH and $R_5$ is ($C_7$–$C_{10}$)alkyl, aryl, aryl($C_1$–$C_6$)alkyl-, —Oaryl, $CF_3$, heterocycloalkyl, —($C_1$–$C_6$)alkylheterocycloalkyl, —($C_2$–$C_7$) alkenylheterocycloalkyl, heteroaryl, —($C_1$–$C_6$) alkylheteroaryl, —($C_2$–$C_7$)alkenylheteroaryl, —($C_2$–$C_7$)alkenlaryl, —($C_2$–$C_7$)alkenylCOaryl, —($C_1$–$C_6$)alkylN($R^4$)CO-aryl, —($C_1$–$C_6$)alkylCO-aryl, —($C_1$–$C_6$)alkylhydroxyaryl, —($C_1$–$C_6$)alkyl-X-aryl, ($C_2$–$C_7$)alkenyl, benzyhydryl, 5-hydroxyoxoindanyl, or tetrahydronaphthanenyl, wherein X is O, S, SO, $SO_2$ or NR$^1$; —N($R^1$) OCOaryl; =CHCO$_2$R$^1$; =CHCONR$^1$R$^2$; =CHCN; =NNHSO$_2$R$_6$ wherein R$_6$ is aryl; —N(O)=CHR$^6$; —OC(O)NR$^1$R$^7$ wherein R$^7$ is aryl, aryl($C_1$–$C_6$)alkyl-, —($C_1$–$C_6$)alkylCO$_2$($C_1$–$C_6$)alkyl, —CO$_2$($C_1$–$C_6$) alkyl, -CO$_2$aryl, or —C$_2$($C_1$–$C_6$)alkylaryl; amino ($C_1$–$C_6$)alkylarylCO$_2$—; or —OC(O)OR$^8$ wherein R$^8$ is ($C_1$–$C_6$)alkyl, aryl($C_1$–$C_6$)alkyl, or aryl;

with the proviso that the cycloalkenyl ring is not aromatic.

* * * * *